United States Patent
Olsen et al.

(10) Patent No.: US 10,919,949 B2
(45) Date of Patent: Feb. 16, 2021

(54) ACYLATED INSULIN ANALOGUES AND USES THEREOF

(71) Applicant: Novo Nordisk A/S, Bagsvaerd (DK)

(72) Inventors: Grith Skytte Olsen, Vaerloese (DK); Bo Falck Hansen, Virum (DK); Lauge Schaeffer, Lyngby (DK); Ingrid Pettersson, Frederiksberg (DK); Rita Slaaby, Lyngby (DK); Jakob Brandt, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 40 days.

(21) Appl. No.: 15/998,755

(22) Filed: Aug. 16, 2018

(65) Prior Publication Data

US 2019/0194285 A1 Jun. 27, 2019

(30) Foreign Application Priority Data

Aug. 17, 2017 (EP) ..................................... 17186612
Dec. 1, 2017 (EP) ..................................... 17204872

(51) Int. Cl.
| | | |
|---|---|---|
| A61K 38/28 | (2006.01) | |
| C07K 14/62 | (2006.01) | |
| A61P 9/00 | (2006.01) | |
| A61P 3/04 | (2006.01) | |
| A61P 3/10 | (2006.01) | |
| A61P 35/00 | (2006.01) | |
| G01N 33/50 | (2006.01) | |
| A61K 38/00 | (2006.01) | |

(52) U.S. Cl.
CPC ............... *C07K 14/62* (2013.01); *A61P 3/04* (2018.01); *A61P 3/10* (2018.01); *A61P 9/00* (2018.01); *A61P 35/00* (2018.01); *G01N 33/50* (2013.01); *A61K 38/00* (2013.01); *C07K 2319/90* (2013.01); *G01N 2440/14* (2013.01)

(58) Field of Classification Search
CPC .................................. A61K 38/28; C07K 14/62
See application file for complete search history.

(56) References Cited

U.S. PATENT DOCUMENTS

| | | | |
|---|---|---|---|
| 5,618,913 A | 4/1997 | Brange et al. | |
| 8,691,759 B2 * | 4/2014 | Madsen ................ | C07K 14/62 514/5.9 |
| 10,040,839 B2 * | 8/2018 | Madsen ................ | A61K 38/28 |
| 2012/0241356 A1 | 9/2012 | Pfenninger et al. | |

FOREIGN PATENT DOCUMENTS

| | | |
|---|---|---|
| WO | 9007511 A1 | 7/1990 |
| WO | 92/00321 A1 | 1/1992 |
| WO | 92/012999 A1 | 8/1992 |
| WO | 9215611 A1 | 9/1992 |
| WO | 9615804 A1 | 5/1996 |
| WO | 97/31022 A1 | 8/1997 |
| WO | 00/43034 A2 | 7/2000 |
| WO | 00/69901 A2 | 11/2000 |
| WO | 2005/054291 A1 | 6/2005 |
| WO | 2006/008238 A1 | 1/2006 |
| WO | 06/082204 A1 | 8/2006 |
| WO | 07/096431 A1 | 8/2007 |
| WO | 08/034881 A1 | 3/2008 |
| WO | 09/022005 A1 | 2/2009 |
| WO | 2009/112583 A2 | 9/2009 |
| WO | 2009/115469 A1 | 9/2009 |
| WO | 2010/080609 A1 | 7/2010 |
| WO | 2010080606 A1 | 7/2010 |
| WO | 2010080607 A1 | 7/2010 |
| WO | 2011159882 A2 | 12/2011 |
| WO | 2011159895 A2 | 12/2011 |
| WO | 2011161124 A1 | 12/2011 |
| WO | 2011163460 A1 | 12/2011 |
| WO | 2011163462 A2 | 12/2011 |
| WO | 2012/015692 A2 | 2/2012 |
| WO | 2012049307 A2 | 4/2012 |
| WO | 2013022721 A1 | 2/2013 |
| WO | 2013/093009 A1 | 6/2013 |
| WO | 2013096386 A1 | 6/2013 |
| WO | 2014052451 A2 | 4/2014 |
| WO | 2014088836 A1 | 6/2014 |
| WO | 2014099577 A1 | 6/2014 |
| WO | 2014158900 A1 | 10/2014 |
| WO | 2015010927 A1 | 1/2015 |
| WO | 2015051052 A2 | 4/2015 |
| WO | 2016049174 A1 | 3/2016 |
| WO | 2016049190 A1 | 3/2016 |
| WO | 2016081670 A2 | 5/2016 |
| WO | 2016119854 A1 | 8/2016 |
| WO | 2016144658 A1 | 9/2016 |

(Continued)

OTHER PUBLICATIONS

Bas ter Braak et al., "Mammary Gland Tumor Promotion by Chronic Administration of IGF1 and the Insulin Analogue AspB10 in the p53R270H/+WAPCre Mouse Model," Breast Cancer Research, Current Medicine Group Ltd., GB, 2015, vol. 17, No. 1, pp. 1-13.
B. ter Braak et al., "Classifying the Adverse Mitogenic Mode of Action of Insulin Analogues Using a Novel Mechanism-Based Genetically Engineered Human Breast Cancel Cell Panel," Archives of Technology, 2014, vol. 88, No. 4, pp. 953-966.
Hua et al., "A Conserved Histidine in Insulin is Required for the Foldability of Human Proinsulin," Journal of Biological Chemistry, 2006, vol. 281, No. 34, pp. 24889-24899.
Kosinova et al., "Insight into the Structural and Biological Relevance of the T/R Transition of the N-Terminus of the B? Chain in Human Insulin," Biochemistry, 2014, vol. 53, pp. 3392-3402.

(Continued)

*Primary Examiner* — Gyan Chandra
(74) *Attorney, Agent, or Firm* — Jianjie Hu

(57) ABSTRACT

The present invention relates to novel insulin analogues and derivatives thereof, such as acylated insulin analogues, and their pharmaceutical use, in particular in the treatment or prevention of medical conditions relating to diabetes, obesity and cardiovascular diseases.

18 Claims, 10 Drawing Sheets

Specification includes a Sequence Listing.

(56) References Cited

FOREIGN PATENT DOCUMENTS

| WO | 2016164288 A1 | 10/2016 |
| WO | 2016172269 A2 | 10/2016 |
| WO | 2017032798 A1 | 3/2017 |
| WO | 2017040363 A1 | 3/2017 |

OTHER PUBLICATIONS

Tang et al., "Structural Consequences of the B5 Histidine->Tyrosine Mutation in Human Insulin Characterized by X-Ray Crystallography and Conformational Analysis," Biochemistry, 1999, vol. 38, No. 37, pp. 12041-12051.

Torosantucci et al., "Chemical Modifications in Aggregates of Recombinant Human Insulin Induced by Metal-Catalyzed Oxidation: Covalent Cross-Linking via Michael Addition to Tyrosine Oxidation Products," Pharm Res, 2012, vol. 29, pp. 2276-2293.

* cited by examiner

SEQUENCE LISTING

```
<160> NUMBER OF SEQ ID NOS: 15

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Gly Ile Val Glu Gln Cys Cys Thr Ser Ile Cys Ser Leu Glu Gln Leu
1               5                   10                  15

Glu Asn Tyr Cys Asn
            20
```

```
<210> SEQ ID NO 4
<211> LENGTH: 28
<212> TYPE: PRT
<213> ORGANISM: Artificial Sequence
<220> FEATURE:
<223> OTHER INFORMATION: Synthetic

<400> SEQUENCE: 4

Phe Val Asn Gln Tyr Leu Cys Gly Ser His Leu Val Glu Ala Leu Tyr
1               5                   10                  15

Leu Val Cys Gly Glu Arg Gly Phe Phe Ala Thr Lys
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic

<400> SEQUENCE: 5

Phe Val Asn Gln Tyr Leu Cys Gly Ser His Leu Val Glu Ala Leu Tyr
1               5                   10                  15

Leu Val Cys Gly Glu Arg Gly Phe Phe Gly Thr Lys
            20                  25

<210> SEQ ID NO 6
<211> LENGTH: 28
<212> TYPE: PRT
<213> ORGANISM: Artificial Sequence
<220> FEATURE:
<223> OTHER INFORMATION: Synthetic

<400> SEQUENCE: 6

Phe Val Asn Gln Phe Leu Cys Gly Ser His Leu Val Glu Ala Leu Tyr
1               5                   10                  15

Leu Val Cys Gly Glu Arg Gly Phe Phe Ala Thr Lys
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic

<400> SEQUENCE: 7

Phe Val Asn Gln Tyr Leu Cys Gly Ser His Leu Val Glu Ala Leu Tyr
1               5                   10                  15

Leu Val Cys Gly Glu Arg Gly Phe Phe Ala Thr Lys
            20                  25

<210> SEQ ID NO 8
<211> LENGTH: 28
<212> TYPE: PRT
<213> ORGANISM: Artificial Sequence
<220> FEATURE:
<223> OTHER INFORMATION: synthetic

<400> SEQUENCE: 8

Phe Val Asn Gln Tyr Leu Cys Gly Ser His Leu Val Glu Ala Leu Tyr
1               5                   10                  15

Leu Val Cys Gly Glu Arg Gly Phe Phe Gly Thr Lys
            20                  25
```

<210> SEQ ID NO 9
<211> LENGTH: 28
<212> TYPE: PRT
<213> ORGANISM: Artificial Sequence
<220> FEATURE:
<223> OTHER INFORMATION: Synthetic

<400> SEQUENCE: 9

Phe Val Asn Gln Tyr Leu Cys Gly Ser His Leu Val Glu Ala Leu Tyr
1               5                   10                  15

Leu Val Cys Gly Glu Arg Gly Phe Phe Tyr Thr Lys
            20                  25

<210> SEQ ID NO 10
<211> LENGTH: 28
<212> TYPE: PRT
<213> ORGANISM: Artificial Sequence
<220> FEATURE:
<223> OTHER INFORMATION: Synthetic

<400> SEQUENCE: 10

Phe Val Asn Gln Phe Leu Cys Gly Ser His Leu Val Glu Ala Leu Tyr
1               5                   10                  15

Leu Val Cys Gly Glu Arg Gly Phe Phe Gly Thr Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: Synthetic

<400> SEQUENCE: 11

Phe Val Asn Gln Phe Leu Cys Gly Ser His Leu Val Glu Ala Leu Tyr
1               5                   10                  15

Leu Val Cys Gly Glu Arg Gly Phe Phe Tyr Thr Lys
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthethic sequence

<400> SEQUENCE: 12

Phe Val Asn Gln Tyr Leu Cys Gly Ser His Leu Val Glu Ala Leu Tyr
1               5                   10                  15

Leu Val Cys Gly Glu Arg Gly Phe Phe Lys
            20                  25

```
<210> SEQ ID NO 13
<211> LENGTH: 29
<212> TYPE: PRT
<213> ORGANISM: Artificial Sequence
<220> FEATURE:
<223> OTHER INFORMATION: Synthethic

<400> SEQUENCE: 13

Phe Val Asn Gln Tyr Leu Cys Gly Ser His Leu Val Glu Ala Leu Tyr
1               5                  10                  15

Leu Val Cys Gly Glu Arg Gly Phe Phe Tyr Thr Pro Lys
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthethic

<400> SEQUENCE: 14

Phe Val Asn Gln Tyr Leu Cys Gly Ser His Leu Val Glu Ala Leu Tyr
1               5                  10                  15

Leu Val Cys Gly Glu Arg Gly Phe Phe Gly Thr Pro Lys
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthethic

<400> SEQUENCE: 15

Phe Val Asn Gln Tyr Leu Cys Gly Ser His Leu Val Glu Ala Leu Tyr
1               5                  10                  15

Leu Val Cys Gly Glu Arg Gly Phe Phe Ala Thr Pro Lys
            20                  25
```

ACYLATED INSULIN ANALOGUES AND USES THEREOF

CROSS-REFERENCE TO RELATED APPLICATIONS

This application claims priority to European Patent Application 17186612.2, filed Aug. 17, 2017 and European Patent Application 17204872.0, filed Dec. 1, 2017; the contents of which are incorporated herein by reference.

TECHNICAL FIELD

The present invention relates to novel insulin analogues and derivatives thereof, such as acylated insulin analogues, and their pharmaceutical use, in particular in the treatment or prevention of medical conditions relating to diabetes, obesity and cardiovascular diseases.

INCORPORATION-BY-REFERENCE OF THE SEQUENCE LISTING

The instant application contains a Sequence Listing which has been submitted in ASCII format and is hereby incorporated by reference in its entirety. Said ASCII copy, created on Aug. 2, 2018, is named 170001US01_SeqList.txt and is 6 kilobytes in size.

BACKGROUND

Diabetes mellitus is a metabolic disorder, in which the ability to utilise glucose is partly or completely lost. More than 5% of the global population live with diabetes, with millions more at risk of developing the disease.

With current therapies, still about 50% of people with diabetes die of cardiovascular disease and because people with diabetes also are at risk of developing microvascular complications (like nephropathy, retinopathy and neuropathy), there is a continuous need for developing new drugs for improved treatment. Especially in the case of Type 2 diabetes mellitus, since these patients, in addition to hyperglycemia, often suffer from various metabolic dysfunctions, such as e.g. dyslipidemia, obesity and cardiovascular complications for which current insulin therapy only have limited beneficial effect.

In the liver, insulin suppresses gluconeogenesis and glycogenolysis, and increases glycogen synthesis, resulting in decreased glucose output from the liver. These processes are markedly impaired by hepatocyte insulin resistance, and this is the major cause of fasting hyperglycemia in the metabolic syndrome. In addition to the effects on glucose metabolism, insulin also increases the synthesis of fatty acids and triglycerides in the liver through activation of the transcription factor SREBP-1c, which in turn increases transcription of genes for lipogenic enzymes, including acetyl-coenzyme A carboxylase and fatty acid synthase (FAS). However, in contrast to the effects on glycogen synthesis and glucose production, insulin-induced increase in lipid synthesis is not affected at all, or at least less impaired in insulin resistant rodent models of type II diabetes as well as in humans suffering from diabetes caused by lipodystrophy or mutations affecting specific nodes in the intracellular insulin signalling pathways. Accordingly, the hyperinsulinemia associated with metabolic syndrome can directly cause increases in hepatic lipid synthesis and thereby exacerbate the increases in circulating levels of triglycerides. This is a very likely reason why several studies indicate that hepatic insulin resistance contributes to human dyslipidaemia, hepatic steatosis, cardiovascular vascular dysfunction, and even reduced kidney function observed in people with Type 2 diabetes. In line with this, treatment of insulin resistant subjects with a high concentration of insulin in order to lower blood glucose levels may result in over-stimulation of the non-resistant pathways involved in e.g. de novo lipogenesis. In order to lower blood glucose levels without over-stimulating non-resistant pathways (e.g. the lipogenic pathways), it would be desirable to have access to insulin analogues, which selectively activate the glucose lowering pathways. Such functionally selective insulin analogues would, beyond lowering blood glucose levels, exhibit improved effects on dyslipidaemia, hepatic steatosis, atherosclerosis and cardiovascular diseases (CVD).

WO 2005 054291 allegedly describes single chain insulins with B28K acylation. WO 2009 112583 allegedly describes protease stabilised insulin analogues comprising B28K. WO90/07511, WO96/15804, WO200043034, US2012241356, WO2012015692 and WO9731022 allegedly disclose insulin analogues comprising B28K, some of which allegedly also discloses acylation at the same position.

A great variety of insulin analogues and derivatives have been reported. However they all activate the insulin receptor in quite the same manner, i.e. the downstream effects of the insulin receptor activation are rather similar, regardless of whether the activation results from binding a high-affinity analogue or a low-affinity analogue—only the potency differs.

Thus, there is still a need for insulin analogues and derivatives having functionally selective properties on the resistant and non-resistant pathways, e.g. gluconeogenesis and lipid metabolism pathways.

SUMMARY

In a first aspect, the present invention relates to an insulin derivative, wherein said insulin derivative comprises B5Y and a substituent comprising an acyl group.

In a second aspect, the present invention relates to an insulin derivative, wherein said insulin derivative comprises B5F and a substituent comprising an acyl group.

In another aspect, the present invention relates to an insulin derivative, wherein said insulin derivative comprises B5Y and B26G or B26A and a substituent comprising an acyl group attached to B28K, B26K or B29K.

In another aspect, the present invention relates to an insulin derivative, wherein said insulin derivative comprises B5F and B26G or B26A and a substituent comprising an acyl group attached to B28K, B26K or B29K.

In another aspect, the invention provides pharmaceutical compositions comprising the insulin derivative of the invention, and one or more pharmaceutically acceptable carriers or diluents.

In further aspects, the invention relates to the use of the insulin derivatives according to the invention for the manufacture of a medicament for the treatment or prevention of diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, stroke, inflammatory bowel syndrome, dyspepsia, hypotension or gastric ulcers.

Also, or alternatively in a second aspect, the invention provides insulin derivatives with improved effects on processes related to obesity, dyslipidemia or cardiovascular complications, such as a lower weight gain, lower increase in body fat mass, lower increase in liver triglycerides or improved endothelial function.

In one aspect, the insulin derivatives of the present invention are capable of lowering blood glucose without negatively impacting lipid metabolism.

In another aspect, the insulin derivatives of the present invention induce a submaximal insulin receptor phosphorylation, and induce selective signalling, and thus selective cellular response, i.e. give a lower maximal response on lipid metabolism pathways than on glucose lowering pathway, when compared to human insulin.

In yet another aspect, the insulin derivatives of the present invention, besides the glucose lowering, also have lower weight gain, in particular by a lower increase in fat mass.

In one aspect the invention provides insulin derivatives with improved effects on processes related to hepatic dyslipidaemia, hepatic steatosis or non-alcoholic fatty liver disease (NAFLD), in particular by increased lowering of liver triglycerides compared to human insulin.

In another aspect, the invention provides insulin derivatives with improved effects on processes related to cardiovascular disorders such as improved endothelial function compared to human insulin.

In yet another aspect, the insulin derivatives of the present invention provide lower incidence of adverse cardiovascular events in patients with diabetes.

In one aspect the invention provides insulin derivatives with improved stability in formulation.

The invention may also solve further problems that will be apparent from the disclosure of the exemplary embodiments.

DESCRIPTION

Figure 1:
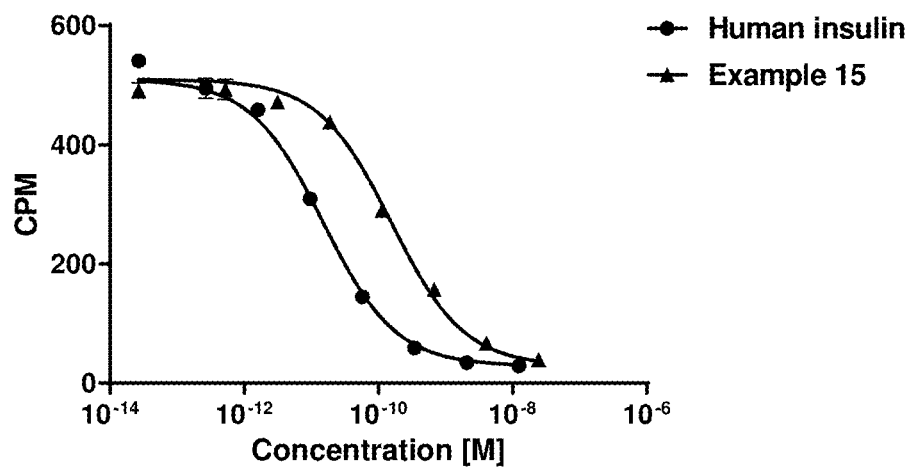
FIG. 1 shows representative receptor binding curves for human insulin (●) and compound of example 15 (▲) from a competition binding assay with solubilised IR-A (CPM=counts per minute)

The present invention provides novel analogues of human insulin, which are acylated and show functionally selective properties on the pathways involved in gluconeogenesis and lipid metabolism.

The present invention relates broadly to insulin derivatives comprising B5Y or B5F and a substituent comprising an acyl group.

In one embodiment, the insulin derivatives of the present invention induce a submaximal phosphorylation of insulin receptor of about or below 65%, when compared to human insulin.

In one embodiment, the insulin derivative comprises a substituent comprising an acyl group.

In one embodiment, the substituent is attached to B28K, B26K or B29K.

In one embodiment, the substituent is attached to B28K.
In one embodiment, the substituent is attached to B26K.
In one embodiment, the substituent is attached to B29K.
In another embodiment, the insulin derivative comprises B26G or B26A.
In another embodiment, the insulin derivative comprises A14E.
In another embodiment, the insulin derivative comprises desB30, desB29-30 or desB27-30.

In another embodiment, the insulin derivative comprises desB30.
In another embodiment, the insulin derivative comprises desB29-30.
In another embodiment, the insulin derivative comprises desB27-30.
In another embodiment the insulin derivative of the invention is selected from the group consisting of the compounds of examples 1-46:

| Ex | Name | Mutations | Linker | Acyl group | Acylation site |
|---|---|---|---|---|---|
| 1 | N{Epsilon-B28}-15-carboxypentadecanoyl-[TyrB5,LysB28],des-(B29-B30)-Insulin | B5Y, B28K, desB29-B30 | none | C16 diacid | B28K |
| 2 | N{Epsilon-B28}-[(4S)-4-carboxy-4-(15-carboxypentadecanoylamino)butanoyl]-[TyrB5,LysB28],des-(B29-B30)-Insulin | B5Y, B28K, desB29-B30 | gGlu | C16 diacid | B28K |
| 3 | N{Epsilon-B28}-17-carboxyheptadecanoyl-[TyrB5,LysB28],des-(B29-B30)-Insulin | B5Y, B28K, desB29-B30 | none | C18 diacid | B28K |
| 4 | N{Epsilon-B28}-[(4S)-4-carboxy-4-(17-carboxyheptadecanoylamino)butanoyl]-[TyrB5,LysB28],des-(B29-B30)-Insulin | B5Y, B28K, desB29-B30 | gGlu | C18 diacid | B28K |
| 5 | N{Epsilon-B28}-[2-[2-[2-(17-carboxyheptadecanoylamino)ethoxy]ethoxy]acetyl]-[TyrB5,LysB28],des-(B29-B30)-Insulin | B5Y, B28K, desB29-B30 | OEG | C18 diacid | B28K |
| 6 | N{Epsilon-B28}-[(4S)-4-carboxy-4-[[(4S)-4-carboxy-4-(17-carboxyheptadecanoylamino)butanoyl]amino]butanoyl]-[TyrB5,LysB28],des-(B29-B30)-Insulin | B5Y, B28K, desB29-B30 | 2xgGlu | C18 diacid | B28K |
| 7 | N{Epsilon-B28}-[2-[2-[2-[[(4S)-4-carboxy-4-(17-carboxyheptadecanoylamino)butanoyl]amino]ethoxy]ethoxy]acetyl]-[TyrB5,LysB28],des-(B29-B30)-Insulin | B5Y, B28K, desB29-B30 | gGlu-OEG | C18 diacid | B28K |
| 8 | N{Epsilon-B28}-[(4S)-4-carboxy-4-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]butanoyl]-[TyrB5,LysB28],des-(B29-B30)-Insulin | B5Y, B28K, desB29-B30 | gGlu | Litocholic acid | B28K |
| 9 | N{Epsilon-B28}-[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]-[TyrB5,LysB28],des-(B29-B30)-Insulin | B5Y, B28K, desB29-B30 | none | Litocholic acid | B28K |
| 10 | N{Epsilon-B28}-15-carboxypentadecanoyl-[TyrB5,GlyB26,LysB28],des-(B29-B30)-Insulin | B5Y, B26G, B28K, desB29-B30 | none | C16 diacid | B28K |
| 11 | N{Epsilon-B28}-17-carboxyheptadecanoyl-[TyrB5,GlyB26,LysB28],des-(B29-B30)-Insulin | B5Y, B26G, B28K, desB29-B30 | none | C18 diacid | B28K |
| 12 | N{Epsilon-B28}-17-carboxyheptadecanoyl-[GluA14,TyrB5,GlyB26,LysB28],des-(B29-B30)-Insulin | A14E, B5Y, B26G, B28K, desB29-B30 | none | C18 diacid | B28K |
| 13 | N{Epsilon-B28}-[(4S)-4-carboxy-4-(17-carboxyheptadecanoylamino)butanoyl]-[GluA14,TyrB5,GlyB26,LysB28],des-(B29-B30)-Insulin | A14E, B5Y, B26G, B28K, desB29-B30 | gGlu | C18 diacid | B28K |

| Ex | Name | Mutations | Linker | Acyl group | Acylation site |
|---|---|---|---|---|---|
| 14 | N{Epsilon-B28}-[(4S)-4-carboxy-4-[[(4S)-4-carboxy-4-(17-carboxyheptadecanoylamino)butanoyl]amino]butanoyl]-[GluA14,TyrB5,GlyB26,LysB28],des-(B29-B30)-Insulin | A14E, B5Y, B26G, B28K, desB29-B30 | 2xgGlu | C18 diacid | B28K |
| 15 | N{Epsilon-B28}-[2-[2-[2-[[(4S)-4-carboxy-4-(17-carboxyheptadecanoylamino)butanoyl]amino]ethoxy]ethoxy]acetyl]-[GluA14,TyrB5,GlyB26,LysB28],des-(B29-B30)-Insulin | A14E, B5Y, B26G, B28K, desB29-B30 | gGlu-OEG | C18 diacid | B28K |
| 16 | N{Epsilon-B28}-[2-[2-[2-[[(4S)-4-carboxy-4-(19-carboxynonadecanoylamino)butanoyl]amino]ethoxy]ethoxy]acetyl]-[GluA14,TyrB5,GlyB26,LysB28],des-(B29-B30)-Insulin | A14E, B5Y, B26G, B28K, desB29-B30 | gGlu-OEG | C20 diacid | B28K |
| 17 | N{Epsilon-B28}-[2-[2-[2-[[2-[2-[[(4S)-4-carboxy-4-(19-carboxynonadecanoylamino)butanoyl]amino]ethoxy]ethoxy]acetyl]amino]ethoxy]ethoxy]acetyl]-[GluA14,TyrB5,GlyB26,LysB28],des-(B29-B30)-Insulin | A14E, B5Y, B26G, B28K, desB29-B30 | gGlu-2xOEG | C20 diacid | B28K |
| 18 | N{Epsilon-B28}-[(4S)-4-carboxy-4-(19-carboxynonadecanoylamino)butanoyl]-[GluA14,TyrB5,GlyB26,LysB28],des-(B29-B30)-Insulin | A14E, B5Y, B26G, B28K, desB29-B30 | gGlu | C20 diacid | B28K |
| 19 | N{Epsilon-B28}-19-carboxynonadecanoyl-[GluA14,TyrB5,GlyB26,LysB28],des-(B29-B30)-Insulin | A14E, B5Y, B26G, B28K, desB29-B30 | none | C20 diacid | B28K |
| 20 | N{Epsilon-B28}-15-(1H-tetrazol-5-yl)pentadecanoyl-[GluA14,TyrB5,GlyB26,LysB28],des-(B29-B30)-Insulin | A14E, B5Y, B26G, B28K, desB29-B30 | none | Tetrazole-C16 | B28K |
| 21 | N{Epsilon-B28}-17-(1H-tetrazol-5-yl)heptadecanoyl-[GluA14,TyrB5,GlyB26,LysB28],des-(B29-B30)-Insulin | A14E, B5Y, B26G, B28K, desB29-B30 | none | Tetrazole-C18 | B28K |
| 22 | N{Epsilon-B28}-16-(1H-tetrazol-5-yl)hexadecanoyl-[GluA14,TyrB5,GlyB26,LysB28],des-(B29-B30)-Insulin | A14E, B5Y, B26G, B28K, desB29-B30 | none | Tetrazole-C17 | B28K |
| 23 | N{Epsilon-B28}-4-[16-(1H-tetrazol-5-yl)hexadecanoylsulfamoyl]butanoyl-[GluA14,TyrB5,GlyB26,LysB28],des-(B29-B30)-Insulin | A14E, B5Y, B26G, B28K, desB29-B30 | sulfonimide-C4 | Tetrazole-C17 | B28K |
| 24 | N{Epsilon-B28}-4-[4-[15-(1H-tetrazol-5-yl)pentadecanoylsulfamoyl]butanoylsulfamoyl]butanoyl-[GluA14,TyrB5,GlyB26,LysB28],des-(B29-B30)-Insulin | A14E, B5Y, B26G, B28K, desB29-B30 | 2xsulfonimide-C4 | Tetrazole-C16 | B28K |
| 25 | N{Epsilon-B28}-4-[17-(1H-tetrazol-5-yl)heptadecanoylsulfamoyl]butanoyl-[GluA14,TyrB5,GlyB26,LysB28],des-(B29-B30)-Insulin | A14E, B5Y, B26G, B28K, desB29-B30 | sulfonimide-C4 | Tetrazole-C18 | B28K |
| 26 | N{Epsilon-B28}-[2-[2-[2-[[2-[2-[[(4S)-4-carboxy-4-[15-(1H-tetrazol-5-yl)pentadecanoylamino]butanoyl]amino]ethoxy]ethoxy]acetyl]amino]ethoxy]ethoxy]acetyl]-[GluA14,TyrB5,GlyB26,LysB28],des-(B29-B30)-Insulin | A14E, B5Y, B26G, B28K, desB29-B30 | gGlu-2xOEG | Tetrazole-C16 | B28K |
| 27 | N{Epsilon-B28}-4-[4-[17-(1H-tetrazol-5-yl)heptadecanoylsulfamoyl]butanoylsulfamoyl]butanoyl-[GluA14,TyrB5,GlyB26,LysB28],des-(B29-B30)-Insulin | A14E, B5Y, B26G, B28K, desB29-B30 | 2xsulfonimide-C4 | Tetrazole-C18 | B28K |
| 28 | N{Epsilon-B28}-4-(17-carboxyheptadecanoylsulfamoyl)butanoyl-[GluA14,TyrB5,GlyB26,LysB28],des-(B29-B30)-Insulin | A14E, B5Y, B26G, B28K, desB29-B30 | sulfonimide-C4 | C18 diacid | B28K |
| 29 | N{Epsilon-B28}-[2-[2-[2-[[(4S)-4-carboxy-4-[15-(1H-tetrazol-5-yl)pentadecanoylamino]butanoyl]amino]ethoxy]ethoxy]acetyl]-[GluA14,TyrB5,GlyB26,LysB28],des-(B29-B30)-Insulin | A14E, B5Y, B26G-B28K desB29-B30 | gGlu-OEG | Tetrazole-C16 | B28K |

-continued

| Ex | Name | Mutations | Linker | Acyl group | Acylation site |
|----|------|-----------|--------|------------|----------------|
| 30 | N{Epsilon-B28}-[(4R)-4-carboxy-4-(17-carboxyheptadecanoylamino)butanoyl]-[GluA14,TyrB5,GlyB26,LysB28],des-(B29-B30)-Insulin | A14E, B5Y, B26G, B28K, desB29-B30 | DgGlu | C18 diacid | B28K |
| 31 | N{Epsilon-B28}-[2-[2-[2-[[(4S)-4-carboxy-4-(17-carboxyheptadecanoylamino)butanoyl]amino]ethoxy]ethoxy]acetyl]-[TyrB5,GlyB26,LysB28],des-(B29-B30)-Insulin | B5Y, B26G, B28K, desB29-B30 | gGlu-OEG | C18 diacid | B28K |
| 32 | N{Epsilon-B28}-[2-[2-[2-[[(4S)-4-carboxy-4-(17-carboxyheptadecanoylamino)butanoyl]amino]ethoxy]ethoxy]acetyl]-[GluA14,TyrB5,AlaB26,LysB28],des-(B29-B30)-Insulin | A14E, B5Y, B26A, B28K, desB29-B30 | gGlu-OEG | C18 diacid | B28K |
| 33 | N{Epsilon-B28}-[2-[2-[2-[[(4S)-4-carboxy-4-(17-carboxyheptadecanoylamino)butanoyl]amino]ethoxy]ethoxy]acetyl]-[TyrB5,AlaB26,LysB28],des-(B29-B30)-Insulin | B5Y, B26A, B28K, desB29-B30 | gGlu-OEG | C18 diacid | B28K |
| 34 | N{Epsilon-B28}-[(4S)-4-carboxy-4-(17-carboxyheptadecanoylamino)butanoyl]-[GluA14,TyrB5,AlaB26,LysB28],des-(B29-B30)-Insulin | A14E, B5Y, B26A. B28K, desB29-B30 | gGlu | C18 diacid | B28K |
| 35 | N{Epsilon-B28}-17-carboxyheptadecanoyl-[PheB5,LysB28],des-(B29-B30)-Insulin | B5F, B28K, desB29-B30 | none | C18 diacid | B28K |
| 36 | N{Epsilon-B28}-17-carboxyheptadecanoyl-[GluA14,PheB5,GlyB26,LysB28],des-(B29-B30)-Insulin | A14E, B5F, B26G, B28K, desB29-B30 | none | C18 diacid | B28K |
| 37 | N{Epsilon-B26}-17-carboxyheptadecanoyl-[TyrB5,LysB26],des-(B27-B30)-Insulin | B5Y, B26K, desB27-B30 | none | C18 diacid | B26K |
| 38 | N{Epsilon-B26}-[(4S)-4-carboxy-4-(17-carboxyheptadecanoylamino)butanoyl]-[TyrB5,LysB26],des-(B27-B30)-Insulin | B5Y, B26K, desB27-B30 | gGlu | C18 diacid | B26K |
| 39 | N{Epsilon-B26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[TyrB5,LysB26],des-(B27-B30)-Insulin | B5Y, B26K, desB27-B30 | gGlu-2xOEG | C18 diacid | B26K |
| 40 | N{Epsilon-B29}-[(4S)-4-carboxy-4-(15-carboxypentadecanoylamino)butanoyl]-[TyrB5],des-ThrB30-Insulin | B5Y, desB30 | gGlu | C16 diacid | B29K |
| 41 | N{Epsilon-B29}-tetradecanoyl-[TyrB5],des-ThrB30-Insulin | B5Y, desB30 | none | C14 | B29K |
| 42 | N{Epsilon-B29}-[(4S)-4-carboxy-4-(15-carboxypentadecanoylamino)butanoyl]-[TyrB5,GlyB26],des-ThrB30-Insulin | B5Y, B26G, desB30 | gGlu | C16 diacid | B29K |
| 43 | N{Epsilon-B29}-[(4S)-4-carboxy-4-(15-carboxypentadecanoylamino)butanoyl]-[TyrB5,AlaB26],des-ThrB30-Insulin | B5Y, B26A, desB30 | gGlu | C16 diacid | B29K |
| 44 | N{Epsilon-B29}-[(4S)-4-carboxy-4-(17-carboxyheptadecanoylamino)butanoyl]-[TyrB5,GlyB26],des-ThrB30-Insulin | B5Y, B26G, desB30 | gGlu | C18 diacid | B29K |
| 45 | N{Epsilon-B29}-[(4S)-4-carboxy-4-(17-carboxyheptadecanoylamino)butanoyl]-[TyrB5,AlaB26],des-ThrB30-Insulin | B5Y, B26A, desB30 | gGlu | C18 diacid | B29K |

-continued

| Ex | Name | Mutations | Linker | Acyl group | Acylation site |
|---|---|---|---|---|---|
| 46 | N{Epsilon-B26}-[2-[2-[2-[[(4S)-4-carboxy-4-(17-carboxyheptadecanoylamino)butanoyl]amino]ethoxy]ethoxy]acetyl]-[TyrB5,LysB26],des-(B27-B30)-Insulin | B5Y, B26K, desB27-B30 | gGlu-OEG | C18 diacid | B26K |

Ex: example nr.

The present invention relates to the use of the insulin derivatives according to the invention for the manufacture of a medicament for the treatment or prevention of diabetes.

In animal models it has surprisingly been found, that insulin derivatives of the present invention are capable of lowering blood glucose with less negative impact on lipid metabolism or endothelial dysfunction. This is believed to lead to a lower incidence of adverse cardiovascular events, and these animal experiments also show that the glucose lowering is accompanied by a lower weight gain, and in particular by a lower increase in fat mass, when compared to conventional insulin treatment.

This is likely to lead to beneficial effects on liver disease development or progression as the animal experiments also show that the glucose lowering is accompanied by an increased lowering in liver triglycerides when compared to conventional insulin treatment.

Furthermore, when examining the down-stream signalling in vitro, the insulin derivatives of the present invention have shown to induce a submaximal insulin receptor phosphorylation, and to induce selective signalling, and thus selective cellular response, i.e. to give a lower maximal response on lipid metabolism pathways than on glucose lowering pathway, when compared to human insulin.

Finally, the insulin derivatives of the present invention also have a desired selective signalling and improved stability in formulation.

Insulin

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

The human insulin A-chain has the following sequence: GIVEQCCTSICSLYQLENYCN (SEQ ID NO: 1), while the B-chain has the following sequence: FVNQHLCGSHLVEALYLVCGERGFFYTPKT (SEQ ID NO: 2).

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" according to the invention is herein to be understood as human insulin or an insulin from another species, such as porcine or bovine insulin.

The term "insulin peptide" as used herein means a peptide which is either human insulin or an analogue or a derivative thereof with insulin activity.

Insulin Analogue

The term "insulin analogue" as used herein means a single modified human insulin molecule wherein one or more amino acid residues of the insulin have been substituted by other amino acid residues and/or wherein one or more amino acid residues have been deleted from the insulin and/or wherein one or more amino acid residues have been added and/or inserted to the insulin.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modification relative to human insulin.

Modifications in the insulin molecule are denoted stating the chain (A or B), the position, and the one or three letter code for the amino acid residue substituting the native amino acid residue.

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. The connecting peptide includes two terminal dibasic amino acid sequence, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., B5Y, B28K, desB29-desB30 human insulin is an analogue of human insulin where the amino acid in position 5 in the B chain is substituted with tyrosine (Tyr or Y), the amino acid in position 28 in the B chain is substituted with lysine (Lys or K), and the amino acids in positions 29 and 30 in the B chain are deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end).

Herein, the term "amino acid residue" is an amino acid from which, formally, a hydroxy group has been removed from a carboxy group and/or from which, formally, a hydrogen atom has been removed from an amino group.

In one embodiment, the insulin analogue of the present invention is an analogue of human insulin comprising 2-10 mutations.

In one embodiment, the insulin analogue of the present invention is an analogue of human insulin comprising 2-6 mutations.

In one embodiment, the insulin analogue of the present invention is an analogue of human insulin comprising 2-3 mutations.

In one embodiment, the insulin analogue of the present invention is an analogue of human insulin comprising two mutations.

In one embodiment, the insulin analogue of the present invention is an analogue of human insulin comprising three mutations.

In one embodiment, the insulin analogue of the present invention is an analogue of human insulin comprising four mutations.

In one embodiment, the insulin analogue of the present invention is an analogue of human insulin comprising five mutations.

In one embodiment, the insulin analogue of the present invention is an analogue of human insulin comprising six mutations.

In one embodiment, the insulin analogue of the present invention is an analogue of human insulin comprising seven mutations.

In one embodiment, the insulin analogue of the present invention is an analogue of human insulin comprising eight mutations.

In one embodiment, the insulin analogue of the present invention is an analogue of human insulin comprising nine mutations.

In one embodiment, the insulin analogue of the present invention is an analogue of human insulin comprising 10 mutations.

In one embodiment, the insulin analogue of the present invention is an analogue of human insulin comprising less than 10 mutations.

In one embodiment, the insulin analogue of the present invention is an analogue of human insulin comprising less than 7 mutations.

In one embodiment, the insulin analogue of the present invention is an analogue of human insulin comprising less than 5 mutations.

In one embodiment, the insulin analogue of the present invention is an analogue of human insulin comprising less than 4 mutations.

In one embodiment, the insulin analogue of the present invention is an analogue of human insulin comprising less than 3 mutations.

In one embodiment the insulin analogue comprises B5Y.

In one embodiment the insulin analogue comprises B5F.

In one embodiment the insulin analogue comprises B26A or B26G.

In one embodiment, the insulin analogue comprises B26A.

In one embodiment, the insulin analogue comprises B26G.

In another embodiment, the insulin analogue comprises A14E.

In one embodiment, the insulin analogue comprises B5Y and B26A.

In one embodiment, the insulin analogue comprises B5Y and B26G.

In one embodiment, the insulin analogue comprises B5F and B26A.

In one embodiment, the insulin analogue comprises B5F and B26G.

In one embodiment, the insulin analogue comprises B28K, B26K or B29K.

In one embodiment, the insulin analogue comprises B28K.

In one embodiment, the insulin analogue comprises B26K.

In one embodiment, the insulin analogue comprises B29K.

In another embodiment, the insulin analogue comprises B26G or B26A.

In another embodiment, the insulin analogue comprises desB30, desB29-30 or desB27-30.

In another embodiment, the insulin analogue comprises desB30.

In another embodiment, the insulin analogue comprises desB29-30.

In another embodiment, the insulin analogue comprises desB27-30.

In one embodiment, the insulin analogue may further comprise up to 10 substitutions in addition to B5Y.

In one embodiment, the insulin analogue further comprises up to 5 substitutions in addition to B5Y.

In one embodiment, the insulin analogue further comprises two substitutions in addition to B5Y.

In one embodiment, the insulin analogue further comprises three substitutions in addition to B5Y.

In one embodiment, the insulin analogue further comprises four substitutions in addition to B5Y.

In one embodiment, the insulin analogue further comprises five substitutions in addition to B5Y.

In one embodiment, the insulin analogue further comprises six substitutions in addition to B5Y.

In one embodiment, the insulin analogue further comprises seven substitutions in addition to B5Y.

In one embodiment, the insulin analogue further comprises eight substitutions in addition to B5Y.

In one embodiment, the insulin analogue further comprises nine substitutions in addition to B5Y.

In one embodiment, the insulin analogue may further comprise up to 10 substitutions in addition to B5F.

In one embodiment, the insulin analogue further comprises up to 5 substitutions in addition to B5F.

In one embodiment, the insulin analogue further comprises two substitutions in addition to B5F.

In one embodiment, the insulin analogue further comprises three substitutions in addition to B5F.

In one embodiment, the insulin analogue further comprises four substitutions in addition to B5F.

In one embodiment, the insulin analogue further comprises five substitutions in addition to B5F.

In one embodiment, the insulin analogue further comprises six substitutions in addition to B5F.

In one embodiment, the insulin analogue further comprises seven substitutions in addition to B5F.

In one embodiment, the insulin analogue further comprises eight substitutions in addition to B5F.

In one embodiment, the insulin analogue further comprises nine substitutions in addition to B5F.

Non-limiting examples of insulin analogues of the present invention include:

A14E, B5Y, B26A, B28K, desB29-30 (SEQ ID NO: 3 and 4)
A14E, B5Y, B26G, B28K, desB29-30 (SEQ ID NO: 3 and 5)
B5Y, B26A, B28K, desB29-30 (SEQ ID NO: 1 and 7)
B5Y, B26G, B28K, desB29-30 (SEQ ID NO: 1 and 8)
B5Y, B28K, desB29-30 (SEQ ID NO: 1 and 9)
A14E, B5F, B26G, B28K, desB29-30 (SEQ ID NO: 3 and 10)
B5F, B28K, desB29-30 (SEQ ID NO: 1 and 11)
B5Y, B26K, desB27-desB30 (SEQ ID 1 and 12)
B5Y, desB30 (SEQ ID 1 and 13)
B5Y, B26G, desB30 (SEQ ID 1 and 14)
B5Y, B26A, desB30 (SEQ ID 1 and 15)

In one embodiment, the insulin analogues of the present invention comprise:
A14E, B5Y, B26A, B28K, desB29-30 (SEQ ID NO: 3 and 4)
A14E, B5Y, B26G, B28K, desB29-30 (SEQ ID NO: 3 and 5)
B5Y, B26A, B28K, desB29-30 (SEQ ID NO: 1 and 7)
B5Y, B26G, B28K, desB29-30 (SEQ ID NO: 1 and 8)
B5Y, B28K, desB29-30 (SEQ ID NO: 1 and 9)
A14E, B5F, B26G, B28K, desB29-30 (SEQ ID NO: 3 and 10)
B5F, B28K, desB29-30 (SEQ ID NO: 1 and 11)
B5Y, B26K, desB27-desB30 (SEQ ID 1 and 12)
B5Y, desB30 (SEQ ID 1 and 13)
B5Y, B26G, desB30 (SEQ ID 1 and 14)
B5Y, B26A, desB30 (SEQ ID 1 and 15)
B5F, B26A, B28K, desB29-30 (SEQ ID 1 and 6)
B5Y, B26A, B28K, desB29-30 (SEQ ID NO: 1 and 4)
B5Y, B26G, B28K, desB29-30 (SEQ ID NO: 1 and 5)
B5F, B26G, B28K, desB29-30 (SEQ ID NO: 1 and 10)
A14E, B5F, B26A, B28K, desB29-30 (SEQ ID 3 and 6)
A14E, B5Y, B26A, B28K, desB29-30 (SEQ ID NO: 3 and 7)
A14E, B5Y, B26G, B28K, desB29-30 (SEQ ID NO: 3 and 8)
A14E, B5Y, B28K, desB29-30 (SEQ ID NO: 3 and 9)
A14E, B5F, B28K, desB29-30 (SEQ ID NO: 3 and 11)
A14E, B5Y, B26K, desB27-desB30 (SEQ ID 3 and 12)
A14E, B5Y, desB30 (SEQ ID 3 and 13)
A14E, B5Y, B26G, desB30 (SEQ ID 3 and 14) and
A14E, B5Y, B26A, desB30 (SEQ ID 3 and 15).

Insulin Derivative

The term "insulin derivative" as used herein means a chemically modified parent insulin or analogue thereof, in which one or more side chains have been covalently attached to the peptide. The term "side chain" as used herein may also be referred to as a "substituent" or "albumin binding moiety". Non-limiting examples of side chains are amides, carbohydrates, alkyl groups, acyl groups, esters, PEGylations, and the like, which may further comprise a linker.

The term "albumin binding moiety" as used herein refers to any chemical group capable of non-covalent binding to albumin, i.e. has albumin binding affinity. In some embodiments the albumin binding moiety comprises an acyl group.

In another particular embodiment the side chain comprises a portion which is particularly relevant for the albumin binding and thereby the protraction, which portion may accordingly be referred to as a "protracting moiety" or "protractor" or "acyl group". The protracting moiety may be near, and preferably at the terminal (or distal, or free) end of the albumin binding moiety, relative to its point of attachment to the peptide.

The "substituent", "side chain" or "albumin binding moiety" according to the present invention has the following formula (I):

Acy-L1-L2-L3 wherein:

Acy is an acyl group and is represented by lithocholic acid, by a functional group of the formulae:

—CO—(CH$_2$)$_x$—COOH; or     Chem. 1

—CO—(CH$_2$)$_x$-tetrazolyl;     Chem. 2 wherein x represents an integer in the range of from 12 to 20; and the tetrazolyl group is 1H-tetrazol-5-yl or by a fatty acid of formula:

—CO—(CH$_2$)$_x$—CH$_3$     Chem. 3 wherein x represents an integer in the range from 8 to 16

L1 is absent or represents OEG, gGlu, DgGlu or sulfonimide C-4

L2 is absent or represents OEG, gGlu, DgGlu or sulfonimide C-4

L3 is absent or represents OEG, gGlu, DgGlu or sulfonimide C-4 wherein:

OEG represents [2-(2-aminoethoxy)ethoxy]acetyl or amino acid residue 8-amino-3,6-dioxaoctanoic acid —NH(CH$_2$)$_2$O(CH$_2$)$_2$OCH$_2$CO— and is represented by the following structure:

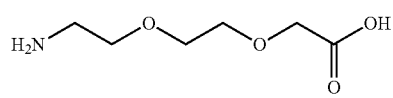 [SMILES: NCCOCCOCC(=O)O]

gGlu represents a gamma glutamic acid residue represented by the following structure:

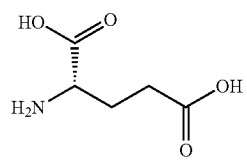

wherein the carboxyl group on the right of the structure drawing is the gamma-carboxy group which forms the bond to the neighbouring amino group DgGlu represents a gamma glutamic acid residue represented by the following structure:

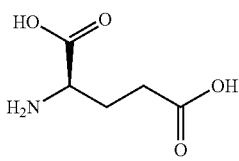

wherein the carboxyl group on the right of the structure drawing is the gamma-carboxy group which forms the bond to the neighbouring amino group and sulfonimide C-4 is represented by the following structure:

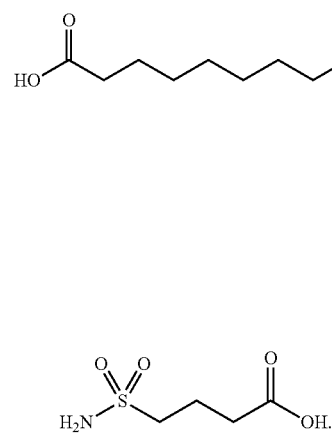

In one embodiment, L1-L2-L3 of formula (I) is represented independently by:
- none
- gGlu
- OEG
- 2xgGlu
- gGlu-OEG
- gGlu-2xOEG
- sulfonimide-C4
- 2xsulfonimide-C4
- DgGlu In one embodiment, the substituent has formula (I) Acy-L1-L2-L3 and is represented independently by:
- Lithocholic acid
- Lithocholic acid-gGlu
- C14
- C16 diacid
- C16 diacid-gGlu
- C18 diacid
- C18 diacid-gGlu
- C18 diacid-2xgGlu
- C18 diacid-DgGlu
- C18 diacid-gGlu-OEG
- C18 diacid-gGlu-2xOEG
- C18 diacid-OEG
- C18 diacid-sulfonimide-C4
- C20 diacid
- C20 diacid-gGlu
- C20 diacid-gGlu-OEG
- C20 diacid-gGlu-2xOEG
- Tetrazole-C16
- Tetrazole-C16-gGlu-OEG
- Tetrazole-C16-gGlu-2xOEG
- Tetrazole-C16-2xsulfonimide-C4
- Tetrazole-C17
- Tetrazole-C17-sulfonimide-C4
- Tetrazole-C18;
- Tetrazole-C18-sulfonimide-C4
- Tetrazole-C18-2xsulfonimide-C4

In one embodiment, the substituent is the substituent of compound of example 15, wherein Acy-L1-L2-L3 is represented by C18diacid-gGlu-OEG and by the structure:

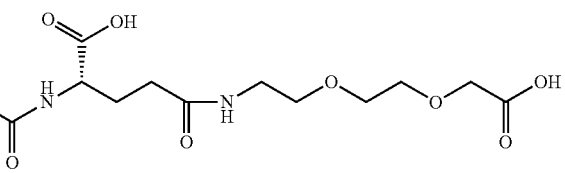

In one embodiment, the insulin derivatives of the invention are selected from the group consisting of the compounds of Examples 1-46.

In yet another embodiment, the insulin derivatives of the invention are selected from the group consisting of the compounds of Examples 1-36.

In yet another embodiment the insulin derivative of the invention is selected from the group consisting of the compounds of Examples 10-34.

In yet another embodiment the insulin derivative of the invention is selected from the group consisting of the compounds of Examples 3, 4, 12-16, 18-20, 22, 23, 25, 26, 28-30.

In yet another embodiment the insulin derivative of the invention is selected from the group consisting of the compounds of Examples 14-16, 18, 20 and 26.

In yet another embodiment, the insulin derivatives of the invention are selected from the group consisting of the compounds of Examples 37-39 or 46.

In yet another embodiment, the insulin derivatives of the invention are selected from the group consisting of the compounds of Examples 40-45.

In one embodiment the insulin derivative of the invention is the compound of Example 15: N{Epsilon-B28}-[2-[2-[2-[[(4S)-4-carboxy-4-(17-carboxyheptadecanoylamino)butanoyl]amino]ethoxy]ethoxy]acetyl]-[GluA14,TyrB5,GlyB26,LysB28],des-(B29-B30)-Insulin

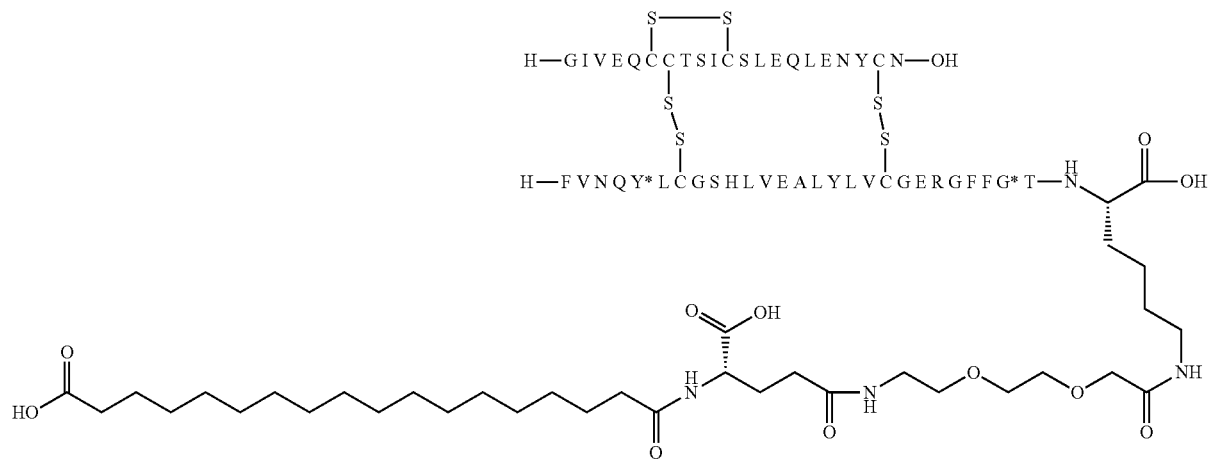

Acyl Group

In one embodiment, the insulin derivatives of the invention comprise an acyl group. The insulin derivatives comprising an acyl group can therefore be referred to as "acylated insulin analogues".

In a preferred embodiment, the insulin derivatives of the invention comprise an acyl group (Acy) wherein the acyl group represents lithocholic acid, or a functional group of formulae:

—CO—(CH$_2$)$_x$—COOH; or     Chem. 1

—CO—(CH$_2$)$_x$-tetrazolyl-     Chem. 2 wherein x represents an integer in the range of from 12 to 20; and the tetrazolyl group is 1H-tetrazol-5-yl
or a fatty acid of formula:

—CO—(CH$_2$)$_x$—CH$_3$     Chem. 3 wherein x represents an integer in the range from 8 to 16.

In one embodiment, Acy is selected from the group consisting of: lithocholic acid, 1,16-hexadecanedioic acid, 1,18-octadecanedioic acid, 1,20-eicosanedioic acid, tetrazole-C16, tetrazole-C17, tetrazole C18 and tetradecanoic acid.

In one embodiment, the insulin derivative comprises an acyl group, which comprises a dicarboxylic acid.

In one embodiment, the insulin derivative comprises an acyl group of the formula of Chem 1, wherein x represents an integer in the range of from 12 to 20.

In one embodiment, the insulin derivative comprises an acyl group of the formula of the formula of Chem 1, wherein x represents an integer in the range of from 12 to 18.

In one embodiment, the insulin derivative comprises an acyl group of the formula of the formula of Chem 1, wherein x represents an integer in the range of from 12 to 16.

In one embodiment, the insulin derivative comprises an acyl group of the formula of the formula of Chem 1, wherein x represents an integer in the range of from 12 to 14.

In one embodiment, the insulin derivative comprises an acyl group of the formula of the formula of Chem 1; wherein x represents integer 14, 16 or 18, i.e., the fatty diacid group 1,16-hexadecanedioic acid, 1,18-octadecanedioic acid, and 1,20-eicosanedioic acid, respectively.

In one embodiment, the insulin derivative comprises an acyl group of the formula —CO—(CH$_2$)$_{12}$—COOH and is represented by the following structure:

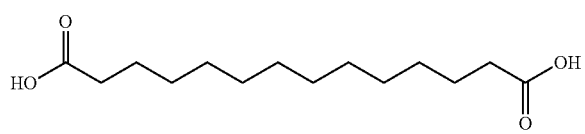 [SMILES: O=C(O)CCCCCCCCCCCCC(=O)O]

In one embodiment, the insulin derivative comprises an acyl group of the formula —CO—(CH$_2$)$_{14}$—COOH also named 1,16-hexadecanedioic acid and is represented by the following structure:

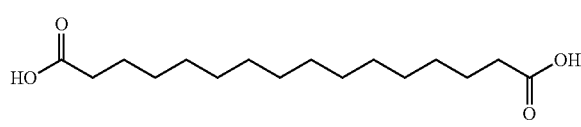 [SMILES: O=C(O)CCCCCCCCCCCCCCC(=O)O]

In one embodiment, the insulin derivative comprises an acyl group of the formula —CO—(CH$_2$)$_{16}$—COOH, also referred to as 1,18-octadecanedioic acid and is represented by the following structure:

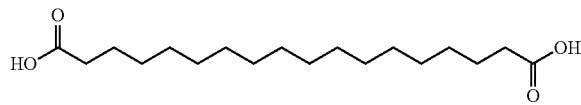 [SMILES: O=C(O)CCCCCCCCCCCCCCCCC(=O)O]

In one embodiment, the insulin derivative comprises an acyl group of the formula —CO—(CH$_2$)$_{18}$—COOH also referred to as 1,20-eicosanedioic acid and is represented by the following structure:

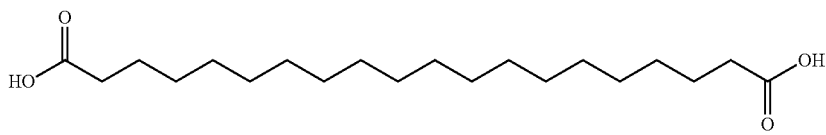 [SMILES: O=C(O)CCCCCCCCCCCCCCCCCCC(=O)O]

In one embodiment, the insulin derivative comprises an acyl group of the formula —CO—(CH$_2$)$_{20}$—COOH and is represented by the following structure:

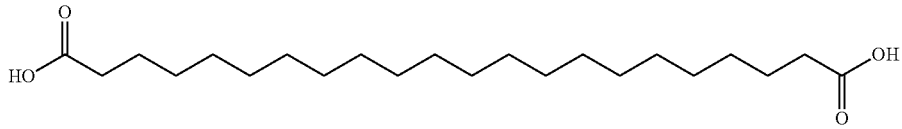 [SMILES: O=C(O)CCCCCCCCCCCCCCCCCCCCC(=O)O]

In one embodiment, the insulin derivative comprises an acyl group comprising lithocholic acid and is represented by the following structure:

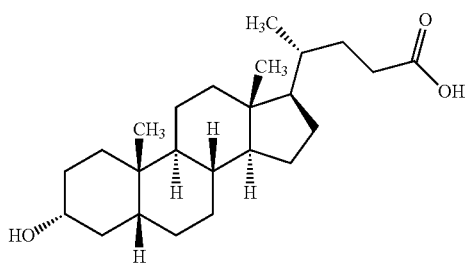

In one embodiment, the insulin derivative comprises an acyl group comprising a fatty acid of the formula —CO—(CH$_2$)$_{12}$—CH$_3$ and is represented by the following structure:

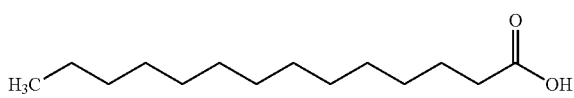 [SMILES: CCCCCCCCCCCCCC(=O)O]

In another embodiment, the insulin derivative comprises an acyl group comprising at least one functional group.

In one embodiment, the insulin derivative comprises an acyl group comprising a functional group selected from the group consisting of a carboxylic acid and a tetrazole moiety.

In one embodiment, the insulin derivative comprises an acyl group comprising a functional group selected from formulae:

—CO—(CH$_2$)$_x$—COOH; or  Chem. 1

—CO—(CH$_2$)$_x$-tetrazolyl-  Chem. 2 wherein x represents an integer in the range of from 12 to 20; and the tetrazolyl group is 1H-tetrazol-5-yl.

In one embodiment, the insulin derivative comprises a functional group comprising a tetrazole moiety which is selected from the group consisting of tetrazole-C16, tetrazole-C17 and tetrazole C18.

In one embodiment, the insulin derivative comprises a functional group which is tetrazole-C16 represented by the following structure:

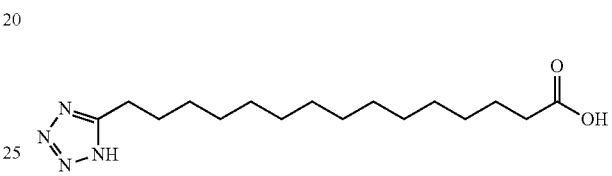

In one embodiment, the insulin derivative comprises a functional group which is tetrazole-C17 represented by the following structure:

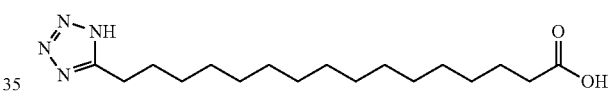

In one embodiment, the insulin derivative comprises a functional group which is tetrazole-C18 represented by the following structure:

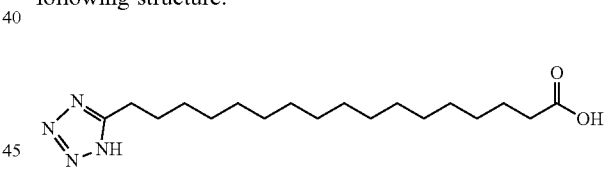

In one embodiment, the insulin derivative comprises a fatty acid.

In one embodiment, the insulin derivative comprises a fatty acid of formula:

—CO—(CH$_2$)$_x$—CH$_3$  Chem. 3 wherein x represents an integer in the range from 8 to 16.

Linker

The term "linker" as used herein includes suitable side chains that can join a moiety, such as a acyl group, to the insulin or insulin analogue. Thus, the linker and the acyl group become a side chain together. The moiety joined to the linker may be any suitable moiety. Examples include an albumin binding moiety.

The linker can contribute to and/or enhance the binding effect of the moiety (for example the albumin binding moiety), e.g. a linker comprising gGlu can enhance the albumin binding effect of insulin or the insulin analogue.

In one embodiment the side chain comprises a portion between the acyl group and the point of attachment to the insulin or insulin analogue, which portion may be referred to as a "linker", "linker moiety", "linker group", "linking group", "spacer", or the like. The linker may be optional, and hence in that case the side chain may be identical to the acyl group.

The acyl group or the linker may be covalently attached to a lysine residue of the insulin peptide by acylation, i.e. via an amide bond formed between a carboxylic acid group thereof (of the acyl group, the albumin binding moiety, the protracting moiety, or the linker) and an amino group of the lysine residue or amino acid residue in the N-terminal. Additional or alternative conjugation chemistry include alkylation, ester formation, amide formation, or coupling to a cysteine residue, such as by maleimide or haloacetamide (such as bromo-/chloro-/iodo-) coupling.

In a preferred embodiment, an active ester of the acyl group, preferably comprising a protracting moiety and a linker, is covalently linked to an amino group of a lysine residue, preferably the epsilon amino group thereof, under formation of an amide bond, as explained above.

In another embodiment, the linker group is absent and represents a covalent bond.

In one embodiment, the insulin derivatives of the invention comprise a linker group of formula -L1-L2-L3, wherein:
L1 is absent or represents OEG, gGlu, DgGlu or sulfonimide C-4
L2 is absent or represents OEG, gGlu, DgGlu or sulfonimide C-4
L3 is absent or represents OEG, gGlu, DgGlu or sulfonimide C-4
wherein
gGlu represents a gamma glutamic acid residue represented by the following structure:

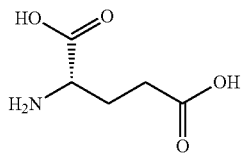

wherein the carboxyl group on the right of the structure drawing is the gamma-carboxy group which forms the bond to the neighbouring amino group
DgGlu represents a gamma glutamic acid residue represented by the following structure:

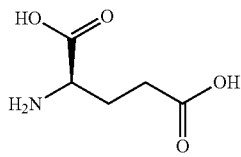

wherein the carboxyl group on the right of the structure drawing is the gamma-carboxy group which forms the bond to the neighbouring amino group
OEG represents [2-(2-aminoethoxy)ethoxy]acetyl and is represented by the following structure:

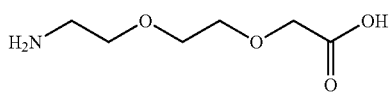

sulfonimide C-4 is represented by the following structure:

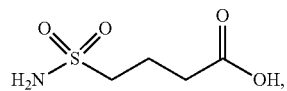

and
2×sulfonimide-C4 or sulfonimide-C4-sulfonimide-C4, is represented by the following structure:

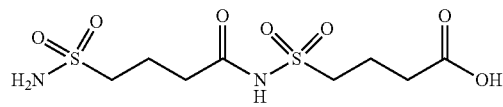

In one embodiment, the insulin peptides of the invention comprise a linker group which represents a divalent linking group selected from DgGlu, gGlu, gGlu-gGlu, gGlu-OEG, gGlu-OEG-OEG, OEG, sulfonimide-C4, and 2× sulfonimide-C4, wherein
gGlu represents a gamma glutamic acid residue; and
OEG represents the amino acid with the formula $NH_2$—$(CH_2)_2$—O—$(CH_2)_2$—O—$CH_2$—COOH, corresponding to the group or residue —NH—$(CH_2)_2$—O—$(CH_2)_2$—O—$CH_2$—CO—, also designated [2-(2-aminoethoxy)ethoxy]acetyl.
sulfonimide-C4, which is represented by the following structure:

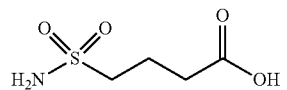

2×sulfonimide-C4 or sulfonimide-C4-sulfonimide-C4, which is represented by the following structure:

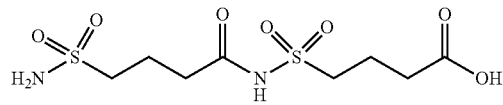

Non-limiting examples of linkers are selected from the list consisting of: DgGlu, gGlu, gGlu-gGlu, gGlu-OEG, gGlu-OEG-OEG, OEG, sulfonimide-C4, 2× sulfonimide-C4.
In one embodiment, the linking group is absent.
In one embodiment, the linking group is DgGlu.
In one embodiment, the linking group is gGlu.
In one embodiment, the linking group is gGlu-gGlu.
In one embodiment, the linking group is gGlu-OEG.
In one embodiment, the linking group is gGlu-OEG-OEG.
In one embodiment, the linking group is OEG.
In one embodiment, the linking group is sulfonimide-C4.
In one embodiment, the linking group is sulfonimide-C4-sulfonimide-C4 or 2×sulfonimide C-4.

Intermediate Products

The invention furthermore relates to an intermediate product in the form of a novel backbone, which when attached to the substituents of the invention, leads to the insulin derivative peptides of the invention.

The invention also relates to an intermediate product in the form of the novel backbone of the insulin peptides of the invention, selected from the group consisting of:

i. A14E, B5Y, B26A, B28K, desB29-30 (SEQ ID NO: 3 and 4)
ii. A14E, B5Y, B26G, B28K, desB29-30 (SEQ ID NO: 3 and 5)
iii. B5Y, B26A, B28K, desB29-30 (SEQ ID NO: 1 and 7)
iv. B5Y, B26G, B28K, desB29-30 (SEQ ID NO: 1 and 8)
v. B5Y, B28K, desB29-30 (SEQ ID NO: 1 and 9)
vi. A14E, B5F, B26G, B28K, desB29-30 (SEQ ID NO: 3 and 10)
vii. B5F, B28K, desB29-30 (SEQ ID NO: 1 and 11)
viii. B5Y, B26K, desB27-desB30 (SEQ ID 1 and 12)
ix. B5Y, desB30 (SEQ ID 1 and 13)
x. B5Y, B26G, desB30 (SEQ ID 1 and 14)
xi. B5Y, B26A, desB30 (SEQ ID 1 and 15)
xii. B5F, B26A, B28K, desB29-30 (SEQ ID 1 and 6)
xiii. B5Y, B26A, B28K, desB29-30 (SEQ ID NO: 1 and 4)
xiv. B5Y, B26G, B28K, desB29-30 (SEQ ID NO: 1 and 5)
xv. B5F, B26G, B28K, desB29-30 (SEQ ID NO: 1 and 10)
xvi. A14E, B5F, B26A, desB29-30 (SEQ ID 3 and 6)
xvii. A14E, B5Y, B26A, B28K, desB29-30 (SEQ ID NO: 3 and 7)
xviii. A14E, B5Y, B26G, B28K, desB29-30 (SEQ ID NO: 3 and 8)
xix. A14E, B5Y, B28K, desB29-30 (SEQ ID NO: 3 and 9)
xx. A14E, B5F, B28K, desB29-30 (SEQ ID NO: 3 and 11)
xxi. A14E, B5Y, B26K, desB27-desB30 (SEQ ID 3 and 12)
xxii. A14E, B5Y, desB30 (SEQ ID 3 and 13)
xxiii. A14E, B5Y, B26G, desB30 (SEQ ID 3 and 14)
xxiv. A14E, B5Y, B26A, desB30 (SEQ ID 3 and 15)

or a pharmaceutically acceptable salt, amide or ester thereof.

Pharmaceutically Acceptable Salt, Amide, or Ester

The intermediate products, analogues and derivatives of the invention may be in the form of a pharmaceutically acceptable salt, amide, or ester.

Salts are e.g. formed by a chemical reaction between a base and an acid, e.g.: 2 $NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group.

The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Stability

Stability of an insulin derivative is defined as the ability to maintain a three dimensional structure (physical stability) as well as the ability to withstand covalent changes in the structure (chemical stability). A favourable stability may be due to inherent properties of the insulin derivative alone or a result of favourable interactions between the insulin derivative and one or more ingredients contained in the vehicle.

Satisfactory stability of an insulin derivative is defined as stability comparable to or better than insulin aspart.

In one aspect the invention provides insulin derivatives with satisfactory stability in formulation.

In one aspect the invention provides insulin derivatives with improved stability in formulation.

The inventors have found that the insulin derivatives according to the invention have satisfactory stability in formulation. The inventors have surprisingly found that the human insulin derivatives according to the invention have both satisfactory stability and retain the partial activation of the insulin receptor.

Stability may be determined by conventional methods and various standard methods known to the person skilled in the art.

Insulin derivatives can for example be screened for stability in formulations including zinc and phenol. In one embodiment the aim is to obtain a formulation including a single insulin self-association state (e.g. a hexameric state) which is not changed during storage or at increased temperature.

An example of a method to measure stability is Differential Scanning calorimetry (DSC), which is a common method to evaluate protein stability, typically by evaluation of onset temperature ($T_{onset}$) of unfolding or, more frequently, by the midpoint of the thermal unfolding ($T_m$) at insulin derivative self-association. It has been described in the literature (Huus et al, Biochemistry (2005) 44, 11171-11177) how the thermal unfolding (by DSC) of insulin correlates to the stability of the zinc-hexamer and with that also with the formulation stability of insulin (Huus et al, Pharm Res (2006) 23(11), 2611-20). A low onset temperature might be seen as insulin dissociation whereas a higher onset temperature indicates a stable insulin derivative complex until unfolding temperature. A satisfactory stability is obtained at $T_{onset}$ and $T_m$ about or above $T_{onset}$ and $T_m$ for insulin aspart (B28D human insulin) at conditions resembling a pharmaceutical formulation.

Another example of such a method is evaluation of insulin self-association by size exclusion chromatography (SEC) using an eluent resembling formulation condition adding phenol and keeping ion strength low. Broad and tailing peaks are sign of several self-association states changing during the chromatography whereas a single sharp peak indicates a stable self-association state.

In one embodiment, an insulin derivative according to the invention has satisfactory chemical and/or physical stability relative to insulin aspart.

In another embodiment, an insulin derivative according to the invention has satisfactory chemical and/or physical stability relative to the corresponding insulin derivative without the B5Y or B5F mutation.

Unless otherwise indicated in the specification, terms presented in singular form also include the plural situation.

In Vitro Biology

Insulin Binding and Receptor Activation/Phosphorylation

Activation of the insulin receptor by insulin leads to activation of the receptor, i.e. phosphorylation of several residues on the receptor, which activation results in a cascade of cellular responses, including cellular processes that contribute to lowering the plasma glucose concentration, cellular processes that regulate lipid metabolism, and cellular processes that promote cell growth and proliferation.

Although the insulin derivatives of the invention are fully capable of displacing human insulin from the insulin receptor, they in fact induce submaximal phosphorylation of the insulin receptor. The insulin derivatives of the present invention therefore may be considered partial agonists with respect to insulin receptor phosphorylation, and they may be referred to as "partial insulin derivatives".

In the context of this invention "partial insulin derivatives" are defined as insulin analogues, which induce insulin receptor phosphorylation, but the maximum response obtained, i.e. the maximum insulin receptor phosphorylation level, is less than the maximum response induced by human insulin, and i.e. is less than 65% of the maximum response induced by human insulin.

A submaximal response or submaximal effect may be defined as a maximum response induced by a partial insulin derivative of the invention that is lower than the maximum response induced by human insulin. To determine if an insulin derivative has a submaximal effect, the maximal response of said derivative has to be determined in an assay and compared to the maximal response of human insulin. The maximum response of an insulin derivative may be determined by measuring the response in the presence of increasing amounts of the insulin derivative, in order to obtain a dose-response curve. The maximum response (Top) can be calculated from the dose-response curve and compared with the maximum response induced by human insulin.

Insulin binding and receptor phosphorylation may be determined by conventional methods, and various standard assays are known to the person skilled in the art. Such standard assays for in vitro determination include i.a. insulin radio-receptor assays, in which the relative affinity of an insulin derivative is defined as the ratio of insulin to insulin derivative required to displace 50% of labelled $^{125}$I-insulin specifically bound to insulin receptors, e.g. on whole cells, on cell membrane fractions, or on purified receptors, as well as insulin receptor phosphorylation assays, in which the ability of the insulin derivative to activate the insulin receptor is determined, e.g. by measuring the phosphorylation of tyrosine residues on the insulin receptor, using e.g. enzyme-linked immunosorbent assay (ELISA) or Western blot techniques.

In one embodiment, the insulin derivatives of the present invention induce a submaximal phosphorylation of insulin receptor of about or below 65%, when compared to human insulin.

In one embodiment, the insulin derivatives of the present invention induce a submaximal phosphorylation of insulin receptor of about or below 60%, when compared to human insulin.

In one embodiment, the insulin derivatives of the present invention induce a submaximal phosphorylation of insulin receptor of about or below 50%, when compared to human insulin.

In one embodiment, the insulin derivatives of the present invention induce a submaximal phosphorylation of insulin receptor of about or below 40%, when compared to human insulin.

In one embodiment, the insulin derivatives of the present invention induce a submaximal phosphorylation of insulin receptor of about or below 30%, when compared to human insulin.

In one embodiment, the insulin derivatives of the present invention induce a submaximal phosphorylation of insulin receptor of about or below 20%, when compared to human insulin.

In one embodiment, the insulin derivatives of the present invention induce a submaximal phosphorylation of insulin receptor of about or below 15%, when compared to human insulin.

In one embodiment, the insulin derivatives of the present invention induce a submaximal phosphorylation of insulin receptor of about or below 12%, when compared to human insulin.

In one embodiment, the insulin derivatives of the present invention induce a phosphorylation of the insulin receptor of about or above 1%, when compared to human insulin.

In one embodiment, the insulin derivatives of the present invention are capable of inducing phosphorylation of the insulin receptor.

Insulin Receptor Signalling

Activation of the insulin receptor initiates a cascade of intracellular responses, such as phosphorylation of residues on, and activation of, various intracellular proteins, including the Extracellular regulated kinase (ERK), also known as MAP kinases (MAPK), and AKT, also known as Protein Kinase B (PKB). Activation of AKT is important for inducing the cellular processes that contributes to lowering the blood glucose concentration, whereas activation of ERK is important for inducing the cellular processes that contributes to promoting cell growth and proliferation in growing cells.

The AKT signalling pathway is an example of a signal transduction pathway that is important for the glucose lowering pathways, wherein AKT is a key protein. In people with Type 2 diabetes, activation of the AKT signalling pathway is greatly impaired, which leads to e.g. a decrease in glucose uptake in to skeletal muscle and adipose tissue. However, the ERK signalling pathway remains responsive to insulin and is an example of a non-resistant pathway that can be over-stimulated during treatment. The activation of the ERK pathway by insulin also encourages the migration and proliferation of VSMCs and collagen synthesis, which are critical steps for the progression of atherosclerotic lesions. In a preferred embodiment the insulin derivatives of the invention induce a submaximal effect on the ERK signalling pathway.

Assays for measuring insulin activated signalling, e.g. the ability to phosphorylate signalling molecules such as ERK and AKT in vitro, are known to the person skilled in the art, and include i.a. Western blot techniques, Surefire and/or ELISA techniques.

The insulin derivatives of the present invention have a lower submaximal effect on ERK activation (phosphorylation) than on AKT activation (phosphorylation), when compared to the effect of human insulin.

Surprisingly we have found that there is a correlation between the maximum insulin receptor phosphorylation (i.e. degree of insulin receptor partiality) that a test compound is able to induce and its ability to activate the glucose lowering pathways without over-stimulating non-resistant pathways. For example, the compounds of the present invention have a lower submaximal effect on ERK activation (phosphorylation) than on AKT activation (phosphorylation), when compared to human insulin and they are capable of reducing blood glucose levels, but have improved effects on processes related to e.g. lipid metabolism, such as less weight gain, less increase in body fat mass and increased lowering of liver TG, and/or improved endothelial function.

Partiality is defined as having the maximal insulin receptor phosphorylation of test compound/maximal insulin receptor phosphorylation of human insulin ratio less than 1.

In one embodiment, the present invention relates to a method for measuring insulin receptor partiality, comprising the following steps:
a) measuring the maximal insulin receptor phosphorylation induced by a test compound
b) measuring the maximal insulin receptor phosphorylation induced by human insulin wherein the ratio of a)/b) is less than 1.

In one embodiment said insulin receptor partiality is less than 0.65.

In one embodiment said insulin receptor partiality is less than 0.6.

In one embodiment said insulin receptor partiality is less than 0.5.

In one embodiment said insulin receptor partiality is less than 0.4.

In one embodiment said insulin receptor partiality is less than 0.3.

In one embodiment said insulin receptor partiality is less than 0.2.

In one embodiment said insulin receptor partiality is less than 0.15.

In one embodiment said insulin receptor partiality is less than 0.12.

Selectivity is defined as the ability of a test compound to activate the glucose lowering pathways without over-stimulating non-resistant pathways, wherein the ratio is less than 1.

In one embodiment, the present invention relates to a method for measuring selectivity, comprising measuring independently the maximal phosphorylation of glucose lowering pathways and non-resistant pathways compared to human insulin and determining if the ratio between glucose lowering pathways/non-resistant pathways is less than 1.

In one embodiment, the present invention relates to a method for measuring selectivity, comprising measuring independently the maximal phosphorylation of ERK and AKT compared to human insulin and determining if the ratio between ERK/AKT is less than 1.

In one embodiment said ratio is less than 0.8.
In one embodiment said ratio is less than 0.7.
In one embodiment said ratio is less than 0.6.
In one embodiment said ratio is less than 0.5.
In one embodiment said ratio is less than 0.4.

Lipid Metabolism/Non-Resistant Pathways

The insulin derivatives of the present invention, when compared to human insulin are able to lower blood glucose levels without over-stimulating non-resistant pathways, e.g. exhibit submaximal effects on lipid metabolism pathways.

As described above, the signalling cascades initiated by insulin through the insulin receptor lead to a wide range of cellular effects, including effects on lipid metabolism pathways. As defined herein the term "lipid metabolism pathways" covers biological actions induced or inhibited by insulin, which actions affect e.g. the synthesis of triglycerides in the liver. An example of a non-resistant pathway is the ERK signalling pathway.

In a preferred embodiment the insulin derivatives of the invention induce a submaximal effect on metabolic pathways related to de novo lipid synthesis (DNL) in primary hepatocytes, as compared to the effect of human insulin. Standard assays for measuring the effect on fatty acid synthesis in liver are known to the skilled person and include i.a. determining the effect on the de novo lipogenesis by measuring the conversion of $^{14}$C-labelled acetate into organic-extractable material (i.e. lipids) in primary hepatocytes.

The signalling cascades initiated by insulin through the insulin receptor leads to induction of the enzymes necessary for regulating lipid metabolism. Example of such enzyme is Fatty Acid Synthase (FAS). FAS is a key enzyme in the cellular processes that serve to regulate lipid synthesis.

The insulin derivatives of the invention also have a submaximal effect on mRNA encoding factors involved in lipid synthesis, e.g. FAS that are only submaximally induced by the insulin derivatives of the present invention in primary hepatocytes, when compared to human insulin.

Standard assays for measuring the ability of insulin and its analogues and derivatives to induce or inhibit mRNA expression of genes involved in lipid metabolism pathways, are known to the person skilled in the art, and include i.a measuring mRNA expression using quantitative real-time polymerase chain reaction (RT-PCR).

Glucose Lowering Pathways

While the insulin derivatives of the invention exhibit a lower submaximal effect on the pathways relating to non-resistant pathways such as lipid metabolism, they are capable of inducing the same maximal response on the glucose lowering pathways as human insulin.

In the context of this invention the term "glucose lowering pathways" cover biological actions induced by insulin that cause lowering of the plasma glucose concentration, such as promoting the storage of glucose in the liver, where insulin activates enzymes that promote glycolysis and glycogenesis, and suppresses those involved in gluconeogenesis, such as promoting incorporation of glucose into lipids in adipocytes, and increasing the uptake of glucose in e.g. muscle.

As described above, the signalling cascades initiated by insulin through the insulin receptor leads to a wide range of cellular effects, including effects on glucose lowering pathways. Examples of insulin stimulated cellular processes that serve to lower plasma glucose concentration are facilitating entry of glucose into muscle, adipose and several other tissues, and stimulating the liver to store glucose in the form of glycogen. The AKT signalling pathway is an example of a signal transduction pathway that is important for the glucose lowering pathways, wherein AKT is a key protein.

In vitro assays for measuring the effect of human insulin, or analogues and derivatives hereof, on glucose lowering pathways are known to the skilled person, and include i.a. assays with isolated rat hepatocytes, where glycogen synthesis can be determined by measuring glycogen accumulation, and lipogenesis assays, performed, e.g., with rat adipocytes wherein the amount of [3-$^3$H] glucose converted into organic-extractable material (i.e. lipids) is measured.

The signalling cascades initiated by insulin through the insulin receptor also lead to activation and/or induction of enzymes and transcription factors necessary for regulating the glucose lowering pathways. An example of such an enzyme is Glucose-6-phosphatase (G6Pc). G6Pc is a rate limiting enzyme in gluconeogenesis that results in the generation of glucose from non-carbohydrate carbon substrates, such as pyruvate, lactate, glycerol, glucogenic amino acids, and odd-chain fatty acids.

The insulin derivatives of the invention exhibit the same maximal effect on stimulating storage of glucose in the form of glycogen in hepatocytes and/or muscles.

The insulin derivatives of the invention have the same maximal effect as human insulin on mRNA encoding factors involved in gluconeogenesis in primary rat hepatocytes.

Standard assays for measuring the ability of human insulin or its analogues and derivatives to induce or inhibit mRNA expression of genes involved in glucose lowering pathways assays are also known to the person skilled in the art, and include i.e. measuring mRNA expression using quantitative RT-PCR.

The insulin derivatives of the invention exhibit full (maximal) effect on the glucose lowering pathways, such as expression of mRNA encoding enzymes involved in gluconeogenesis, stimulation of glycogen synthesis, incorporation of glucose into lipids, in primary cells, e.g. muscle, hepatocytes and/or adipocytes, when comparing to the effects of human insulin.

The insulin derivatives exhibit the same maximal response on stimulating incorporation of glucose into lipid in primary rat adipocytes as human insulin.

In Vivo Biology

In another particular embodiment the insulin derivatives of the invention are capable of reducing blood glucose levels in vivo, and have improved effects on processes related to lipid metabolism, such as less weight gain, less increase in body fat mass, increased lowering of liver triglycerides, or improved endothelial function compared to human insulin, which may be determined as is known in the art in any suitable animal model, as well as in clinical trials.

The C57BL/6J-Diet-Induced Obese (D10) mouse is one example of a suitable animal model, and the blood glucose and/or effects on processes related to lipid metabolism, such as less weight gain, less increase in body fat mass or increased or lowering of liver triglycerides, may be determined in such mice, e.g. as described in Assay (II).

The structural and functional integrity of the endothelium is crucial to maintain vascular homeostasis and prevent atherosclerosis. Endothelial dysfunction comprises a number of functional alterations in the vascular endothelium and impairment of arterial endothelial function is an early event in atherosclerosis and correlates with the major risk factors for cardiovascular disease. Thus, it would be a major advantage to have insulin derivatives which prevents or reduce endothelial dysfunction as these would have a beneficial effect on atherosclerosis and/or CVD.

In one embodiment, the present invention provides insulin derivatives, which are cable of reducing blood glucose levels and have improved effects on endothelial function compared to conventional insulin therapy e.g. prevent or reduce endothelial dysfunction.

In another embodiment the present invention provides insulin derivatives that prevent or reduce a cardiovascular disease in a diabetic subject and/or prevent or reduce development of atherosclerosis.

Arterial endothelial function can be measured by methods known to a person skilled in the art such as measurement of the effect on acetyl-choline induced vasorelaxation in mesenteric arteries e.g. as described in Assay (II).

Hepatic liver metabolism is severely dysregulated in diabetes. Normally, less than 5% of the liver volume is fat, but in patients with non-alcoholic steatohepatitis (NASH) or non alcoholic fatty liver diseases (NAFLD), up to 50%-80% of liver weight may be made up of fat, mostly in the form of triglycerides, see e.g.: Sanyal, A. J. in "AGA technical review on non-alcoholic fatty liver disease", Gastroenterology 2002; 123, 1705-1725.

In a preferred embodiment, the present invention provides insulin derivatives, which are cable of reducing blood glucose levels, but results in lower liver triglyceride content compared to conventional insulin therapy.

Liver triglyceride content can be measured by methods known to a person skilled in the art e.g. as described in (Assay II).

Production of Insulin Peptides

The production of polypeptides, e.g., insulins, is well known in the art. The insulin may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999. The insulin may also be produced by a method which comprises culturing a host cell containing a DNA sequence encoding the analogue and capable of expressing the insulin analogue in a suitable nutrient medium under conditions permitting the expression of the insulin peptide. Several recombinant methods may be used in the production of human insulin and human insulin analogues. Examples of methods which may be used in the production of insulin in microorganisms such as, e.g., *Escherichia coli* and *Saccharomyces cerevisiae* are, e.g., disclosed in WO2008034881.

Typically, the insulin analogue is produced by expressing a DNA sequence encoding the insulin analogue in question or a precursor thereof in a suitable host cell by well-known technique as disclosed in e.g. EP1246845 or WO2008034881.

The insulin analogue may be expressed with an N-terminal extension as disclosed in EP 1,246,845. After secretion to the culture medium and recovery, the insulin precursor will be subjected to various in vitro procedures to remove the possible N-terminal extension sequence and connecting peptide to give the insulin analogue. Such methods include enzymatic conversion by means of trypsin or an *Achromobacter lyticus* protease in the presence of an L-threonine ester followed by conversion of the threonine ester of the insulin analogue into the insulin analogue by basic or acid hydrolysis as described in U.S. Pat. No. 4,343,898 or 4,916,212

Examples of N-terminal extensions of the type suitable in the present invention are disclosed in U.S. Pat. No. 5,395, 922 and EP765395.

For insulin analogues comprising non-natural amino acid residues, the recombinant cell should be modified such that the non-natural amino acids are incorporated into the analogue, for instance by use of tRNA mutants. Hence, briefly, the insulin peptides according to the invention are prepared analogously to the preparation of known insulin analogues.

Protein Purification

The insulin analogues used for making the insulin derivatives of the invention are recovered from the cell culture medium. The insulin analogue used for making insulin derivatives of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-"[an insulin/insulin analogue/insulin derivative]" antibody column. Additional purification may be achieved by conventional chemical purification means, such as high performance liquid chromatography. Other methods of purification, including barium citrate precipitation, are known in the art, and may be applied to the purification of the novel "[an insulin/insulin analogue/insulin derivative]" described herein (see, for example, Scopes, R., Protein Purification, Springer-Verlag, N.Y., 1982).

Pharmaceutical Formulations

Injectable compositions containing an insulin derivative of this invention can be prepared using the conventional techniques of the pharmaceutical industry which involve dissolving and mixing the ingredients as appropriate to give the desired end product. Thus, according to one procedure, an insulin derivative of the invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

Optionally, an insulin preparation of this invention, for example a solution or suspension, may be prepared by dissolving an insulin derivative of the invention in an aqueous medium, for example, in a concentration in the range from about 240 to about 6000 nmol/ml. The aqueous medium is made isotonic, for example, with sodium chloride, propylenglycol or glycerol. Furthermore, the aqueous medium may contain buffers such as acetate or citrate, preservatives such as m-cresol or phenol and zinc ions, for example, in a concentration of up to about 12 Zn/6 ins. The pH value of the solution is adjusted towards neutrality without getting too close to the isoelectric point of the compound of this invention in order to avoid potential precipitation. The pH value of the final insulin preparation depends upon which compound of this invention is used, the concentration of zinc ions and the concentration of the compound of this invention. The insulin preparation is made sterile, for example, by sterile filtration.

EMBODIMENTS

The invention is further described by the following non-limiting embodiments:

1. An insulin derivative, wherein said insulin derivative comprises B5Y or B5F and a substituent comprising an acyl group, or a pharmaceutically acceptable salt, amide or ester thereof.
2. The insulin analogue according to any of the previous embodiments, wherein said insulin derivative further comprises one or more amino acid substitutions and/or deletions.
3. The insulin derivative according to any of the previous embodiments, wherein said insulin derivative further comprises up to 5 additional substitutions and/or deletions.
4. The insulin derivative according to any of the previous embodiments, wherein said insulin derivative further comprises 2, 3 or 4 amino acid substitutions.
5. The insulin derivative according to any of embodiments 1-4, wherein said insulin derivative further comprises B26G or B26A.
6. The insulin derivative according to embodiment 5, wherein said insulin derivative further comprises B26G.
7. The insulin derivative according to embodiment 5, wherein said insulin derivative further comprises B26A.
8. The insulin derivative according to any one of embodiments 1-7, wherein said substituent has the following formula (I):

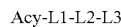

Acy-L1-L2-L3 wherein:
Acy is an acyl group and is represented by lithocholic acid, or by a functional group of the formulae:

—CO—(CH$_2$)$_x$—COOH; or     Chem. 1

—CO—(CH$_2$)$_x$-tetrazolyl;     Chem. 2 wherein x represents an integer in the range of from 12 to 20; and the tetrazolyl group is 1H-tetrazol-5-yl
or a fatty acid of formula:

—CO—(CH$_2$)$_x$—CH$_3$     Chem. 3 wherein x represents an integer in the range from 8 to 16
L1 is absent and represents a covalent bond or represents OEG, gGlu, DgGlu or sulfonimide C-4
L2 is absent and represents a covalent bond or represents OEG, gGlu, DgGlu or sulfonimide C-4
L3 is absent and represents a covalent bond or represents OEG, gGlu, DgGlu or sulfonimide C-4
wherein gGlu represents a gamma glutamic acid residue and OEG represents [2-(2-aminoethoxy)ethoxy]acetyl.
9. The insulin derivative according to any of the previous embodiments, wherein said insulin derivative further comprises A14E.
10. The insulin derivative according to any of the previous embodiments, wherein said insulin derivative further comprises B28K, B26K or B29K.
11. The insulin derivative according to embodiment 10, wherein said insulin derivative further comprises B28K.
12. The insulin derivative according to embodiment 10, wherein said insulin derivative further comprises B26K.
13. The insulin derivative according to embodiment 10, wherein said insulin derivative further comprises B29K.
14. The insulin derivative according to any one of embodiments 1-13, wherein said substituent is attached to the epsilon amino group of the lysine of B26K, B28K or B29K.
15. The insulin derivative according to any one of the previous embodiments, wherein said insulin derivative further comprises desB30, desB29-30 or desB27-30.
16. The insulin derivative according to embodiment 15, wherein said insulin derivative further comprises desB30.
17. The insulin derivative according to embodiment 15, wherein said insulin derivative further comprises desB29-30.
18. The insulin derivative according to embodiment 15, wherein said insulin derivative further comprises desB27-30.

19. The insulin derivative according to any of the previous embodiments, wherein said substitutions are selected from the group consisting of:
   i. A14E, B5Y, B26A, B28K, desB29-30 (SEQ ID NO: 3 and 4)
   ii. A14E, B5Y, B26G, B28K, desB29-30 (SEQ ID NO: 3 and 5)
   iii. B5Y, B26A, B28K, desB29-30 (SEQ ID NO: 1 and 7)
   iv. B5Y, B26G, B28K, desB29-30 (SEQ ID NO: 1 and 8)
   v. B5Y, B28K, desB29-30 (SEQ ID NO: 1 and 9)
   vi. A14E, B5F, B26G, B28K, desB29-30 (SEQ ID NO: 3 and 10)
   vii. B5F, B28K, desB29-30 (SEQ ID NO: 1 and 11)
   viii. B5Y, B26K, desB27-desB30 (SEQ ID 1 and 12)
   ix. B5Y, desB30 (SEQ ID 1 and 13)
   x. B5Y, B26G, desB30 (SEQ ID 1 and 14)
   xi. B5Y, B26A, desB30 (SEQ ID 1 and 15)
   xii. B5F, B26A, B28K, desB29-30 (SEQ ID 1 and 6)
   xiii. B5Y, B26A, B28K, desB29-30 (SEQ ID NO: 1 and 4)
   xiv. B5Y, B26G, B28K, desB29-30 (SEQ ID NO: 1 and 5)
   xv. B5F, B26G, B28K, desB29-30 (SEQ ID NO: 1 and 10)
   xvi. A14E, B5F, B26A, B28K, desB29-30 (SEQ ID 3 and 6)
   xvii. A14E, B5Y, B26A, B28K, desB29-30 (SEQ ID NO: 3 and 7)
   xviii. A14E, B5Y, B26G, B28K, desB29-30 (SEQ ID NO: 3 and 8)
   xix. A14E, B5Y, B28K, desB29-30 (SEQ ID NO: 3 and 9)
   xx. A14E, B5F, B28K, desB29-30 (SEQ ID NO: 3 and 11)
   xxi. A14E, B5Y, B26K, desB27-desB30 (SEQ ID 3 and 12)
   xxii. A14E, B5Y, desB30 (SEQ ID 3 and 13)
   xxiii. A14E, B5Y, B26G, desB30 (SEQ ID 3 and 14)
   A14E, B5Y, B26A, desB30 (SEQ ID 3 and 15)
20. The insulin derivative according to any of the previous embodiments, wherein said acyl group is lithocholic acid, or comprises a functional group of the formulae:

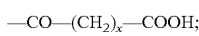  Chem. 1

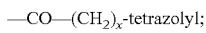  Chem. 2 wherein x represents an integer in the range of from 12 to 20; and the tetrazolyl group is 1H-tetrazol-5-yl.
or is a fatty acid of formula:

  Chem. 3 wherein x represents an integer in the range from 8 to 16.
21. The insulin derivative according to embodiment 20, wherein Acy is selected from the group consisting of: lithocholic acid, 1,16-hexadecanedioic acid, 1,18-octadecanedioic acid, 1,20-eicosanedioic acid, tetrazole-C16, tetrazole-C17, tetrazole C18 and tetradecanoic acid.
22. The insulin derivative according to embodiment 21, wherein said substituent comprises lithocholic acid.
23. The insulin derivative according to embodiment 21, wherein said acyl group comprises a fatty diacid group selected from 1,16-hexadecanedioic acid, 1,18-octadecanedioic acid, and 1,20-eicosanedioic acid.
24. The insulin derivative according to embodiment 23, wherein the at least one substituent comprise a fatty diacid group 1,16-hexadecanedioic acid.
25. The insulin derivative according to embodiment 23, wherein the at least one substituent comprise a fatty diacid group 1,18-octadecanedioic acid.
26. The insulin derivative according to embodiment 23, wherein the at least one substituent comprise a fatty diacid group 1,20-eicosanedioic acid.
27. The insulin derivative according to embodiment 21, wherein said tetrazole moiety is selected from the group consisting of tetrazole-C16, tetrazole-C17 and tetrazole C18.
28. The insulin derivative according to embodiment 27, wherein said tetrazole moiety is tetrazole-C16.
29. The insulin derivative according to embodiment 27, wherein said tetrazole moiety is tetrazole-C17.
30. The insulin derivative according to embodiment 27, wherein said tetrazole moiety is tetrazole C18.
31. The insulin derivative according to embodiment 20, wherein said fatty acid is tetradecanoic acid or C14.
32. The insulin derivative according to any of the previous embodiments, wherein said substituent comprises a linker group.
33. The insulin derivative according to embodiments 1-31, wherein the linker group is absent is represented by a covalent bond.
34. The insulin derivative according to any one of embodiments 1-32, wherein -L1-L2-L3 represents a divalent linker group selected from DgGlu, gGlu, gGlu-gGlu, gGlu-OEG, gGlu-OEG-OEG, OEG, sulfonimide-C4 and sulfonimide-C4-sulfonimide-C4, wherein, gGlu represents a gamma glutamic acid residue; and OEG represents [2-(2-aminoethoxy)ethoxy]acetyl.
35. The insulin derivative according to embodiment 34, wherein said divalent linking group is DgGlu.
36. The insulin derivative according to embodiment 34, wherein said divalent linking group is gGlu.
37. The insulin derivative according to embodiment 34, wherein said divalent linking group is gGlu-gGlu.
38. The insulin derivative according to embodiment 34, wherein said divalent linking group is gGlu-OEG.
39. The insulin derivative according to embodiment 34, wherein said divalent linking group is gGlu-OEG-OEG.
40. The insulin derivative according to embodiment 34, wherein said divalent linking group is OEG.
41. The insulin derivative according to embodiment 34, wherein said divalent linking group is sulfonimide-C4.
42. The insulin derivative according to embodiment 34, wherein said divalent linking group is sulfonimide-C4-sulfonimide-C4.
43. The insulin derivative according to any one of the preceding embodiments, wherein said substituent is the substituent of the compounds of examples 1-46, represented independently by:
Lithocholic acid
Lithocholic acid-gGlu
C14
C16 diacid
C16 diacid-gGlu
C18 diacid
C18 diacid-gGlu
C18 diacid-2×gGlu
C18 diacid-DgGlu
C18 diacid-gGlu-OEG
C18 diacid-gGlu-2×OEG
C18 diacid-OEG
C18 diacid-sulfonimide-C4
C20 diacid
C20 diacid-gGlu
C20 diacid-gGlu-OEG
C20 diacid-gGlu-2×OEG
Tetrazole-C16

Tetrazole-C16-gGlu-OEG
Tetrazole-C16-gGlu-2×OEG
Tetrazole-C16-2×sulfonimide-C4
Tetrazole-C17
Tetrazole-C17-sulfonimide-C4
Tetrazole-C18
Tetrazole-C18-sulfonimide-C4
Tetrazole-C18-2×sulfonimide-C4

44. The insulin derivative according to any one of the previous embodiments, selected from the group consisting of the compounds of Examples 1-46.
45. The insulin derivative according to any one of the previous embodiments, selected from the group consisting of the compounds of Examples 1-36.
46. The insulin derivative according to any one of the previous embodiments, selected from the group consisting of the compounds of Examples 10-34.
47. The insulin derivative according to any one of the previous embodiments, selected from the group consisting of the compounds of Examples 3, 4, 12-16, 18-20, 22, 23, 25, 26, 28-30.
48. The insulin derivative according to any one of the previous embodiments, selected from the group consisting of the compounds of Examples 14-16, 18, 20 and 26.
49. The insulin derivative according to any one of the previous embodiments, selected from the group consisting of the compounds of Examples 37-39 and 46.
50. The insulin derivative according to any one of the previous embodiments, selected from the group consisting of the compounds of Examples 40-45.
51. The insulin derivative according to any one of the previous embodiments, represented by compound of Example 15: N{Epsilon-B28}-[2-[2-[2-[[(4S)-4-carboxy-4-(17-carboxyheptadecanoylamino)butanoyl]amino]ethoxy]ethoxy]acetyl]-[GluA14,TyrB5,GlyB26,LysB28], des-(B29-B30)-Insulin
52. The insulin derivative according to any one of the previous embodiments, wherein said insulin derivative induces a submaximal phosphorylation of insulin receptor of about or below 65%, when compared to human insulin.
53. The insulin derivative according to any one of the previous embodiments, wherein said insulin derivative induces a submaximal phosphorylation of insulin receptor of about or below 60%, when compared to human insulin.
54. The insulin derivative according to any one of the previous embodiments, wherein said insulin derivative induces a submaximal phosphorylation of insulin receptor of about or below 50%, when compared to human insulin.
55. The insulin derivative according to any one of the previous embodiments, wherein said insulin derivative induces a submaximal phosphorylation of insulin receptor of about or below 40%, when compared to human insulin.
56. The insulin derivative according to any one of the previous embodiments, wherein said insulin derivative induces a submaximal phosphorylation of insulin receptor of about or below 30%, when compared to human insulin.
57. The insulin derivative according to any one of the previous embodiments, wherein said insulin derivative induces a submaximal phosphorylation of insulin receptor of about or below 20%, when compared to human insulin.
58. The insulin derivative according to any one of the previous embodiments, wherein said insulin derivative induces a submaximal phosphorylation of insulin receptor of about or below 12%, when compared to human insulin.
59. The insulin derivative according to any of the previous embodiments, for use as a medicament.
60. The insulin derivative according to any of embodiments 1-58, for use in a method of treatment.
61. The insulin derivative according to any of the previous embodiments 1-58, for use in the prevention or treatment of a cardiovascular disease.
62. The insulin derivative according to any of the previous embodiments 1-58, for use in the prevention or treatment of atherosclerosis.
63. The insulin derivative according to any of the previous embodiments 1-58, for use in preventing or reducing of endothelial dysfunction.
64. The insulin derivative according to any of the previous embodiments 1-58, for use in improving lipid parameters.
65. The insulin derivative according to any of the previous embodiments 1-58, for use in preventing or reducing liver triglyceride content.
66. The insulin derivative according to any of the previous embodiments 1-58, for use in for preventing or reducing body weight gain.

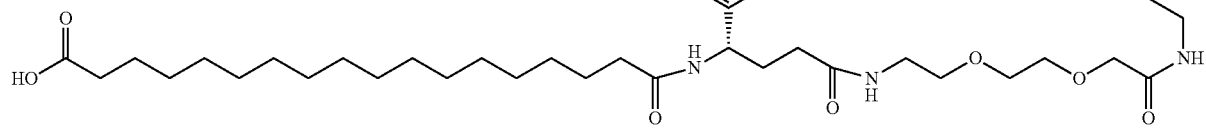

55

67. The insulin derivative according to any of the previous embodiments 1-58, for use in treatment of:
    improving lipid parameters, such as prevention and/or treatment of dyslipidemia, lowering total serum lipids, increasing HDL-C, lowering LDL-C, lowering small, dense LDL-C, lowering VLDL-C, lowering triglycerides, lowering cholesterol, lowering plasma levels of lipoprotein a (Lp(a)) or inhibiting generation of apolipoprotein A (apo(A));
    prevention and/or treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; the treatment of cardiovascular disease.

68. A pharmaceutical composition comprising an insulin derivative according to any of the previous embodiments 1-58, and a pharmaceutically acceptable excipient.

69. The pharmaceutical composition according to embodiment 68, for subcutaneous administration.

70. A pharmaceutical composition for the treatment of diabetes in a patient in need of such treatment, comprising a therapeutically effective amount of an insulin derivative according to any one of embodiments 1-58, together with a pharmaceutically acceptable carrier.

71. The pharmaceutical compositions of embodiments 68-70, for use as a medicament.

72. The pharmaceutical compositions of embodiments 68-70, for use in the treatment of patients with diabetes and high risk of cardiovascular disease.

73. The pharmaceutical compositions of embodiments 68-70 and/or prevent or reduce development of atherosclerosis.

74. Use of an insulin derivative according to any one of embodiments 1-58, for the manufacture of a medicament for the treatment or prevention of diabetes, diabetes of Type 1, diabetes of Type 2, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, stroke, inflammatory bowel syndrome, dyspepsia, hypotension or gastric ulcers.

75. A method for improving lipid parameters comprising a step of administering a pharmaceutically active amount of an insulin derivative according to any of the previous embodiments 1-58.

76. A method for improving lipid parameters comprising a step of administering a pharmaceutically active amount of an insulin derivative according to any of the previous embodiments 1-58, wherein improving lipid parameters, is such as prevention and/or treatment of dyslipidemia, lowering total serum lipids; increasing HDL; lowering LDL-C; lowering small, dense LDL-C; lowering VLDL-C; non_HDL-C; lowering triglycerides; lowering cholesterol; lowering plasma levels of lipoprotein a (Lp(a)); inhibiting generation of apolipoprotein A (apo(A)).

77. A method for prevention and/or treatment of a cardiovascular disease comprising a step of administering a pharmaceutically active amount of an insulin derivative according to any of the previous embodiments 1-58.

78. A method for the treatment or prevention of diabetes, diabetes of Type 1, diabetes of Type 2, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, stroke, inflammatory bowel syndrome, dyspepsia, or gastric ulcers, which method comprises administration to a subject in need thereof a therapeutically effective amount of a derivative of human insulin according to any one of embodiments 1-58.

79. An intermediate product comprising a backbone selected from the group consisting of:
   i. A14E, B5Y, B26A, B28K, desB29-30 (SEQ ID NO: 3 and 4)
   ii. A14E, B5Y, B26G, B28K, desB29-30 (SEQ ID NO: 3 and 5)
   iii. B5Y, B26A, B28K, desB29-30 (SEQ ID NO: 1 and 7)
   iv. B5Y, B26G, B28K, desB29-30 (SEQ ID NO: 1 and 8)
   v. B5Y, B28K, desB29-30 (SEQ ID NO: 1 and 9)
   vi. A14E, B5F, B26G, B28K, desB29-30 (SEQ ID NO: 3 and 10)
   vii. B5F, B28K, desB29-30 (SEQ ID NO: 1 and 11)
   viii. B5Y, B26K, desB27-desB30 (SEQ ID 1 and 12)
   ix. B5Y, desB30 (SEQ ID 1 and 13)
   x. B5Y, B26G, desB30 (SEQ ID 1 and 14)
   xi. B5Y, B26A, desB30 (SEQ ID 1 and 15)
   xii. B5F, B26A, B28K, desB29-30 (SEQ ID 1 and 6)
   xiii. B5Y, B26A, B28K, desB29-30 (SEQ ID NO: 1 and 4)
   xiv. B5Y, B26G, B28K, desB29-30 (SEQ ID NO: 1 and 5)
   xv. B5F, B26G, B28K, desB29-30 (SEQ ID NO: 1 and 10)
   xvi. A14E, B5F, B26A, B28K, desB29-30 (SEQ ID 3 and 6)
   xvii. A14E, B5Y, B26A, B28K, desB29-30 (SEQ ID NO: 3 and 7)
   xviii. A14E, B5Y, B26G, B28K, desB29-30 (SEQ ID NO: 3 and 8)
   xix. A14E, B5Y, B28K, desB29-30 (SEQ ID NO: 3 and 9)
   xx. A14E, B5F, B28K, desB29-30 (SEQ ID NO: 3 and 11)
   xxi. A14E, B5Y, B26K, desB27-desB30 (SEQ ID 3 and 12)
   xxii. A14E, B5Y, desB30 (SEQ ID 3 and 13)
   xxiii. A14E, B5Y, B26G, desB30 (SEQ ID 3 and 14)
   xxiv. A14E, B5Y, B26A, desB30 (SEQ ID 3 and 15) or a pharmaceutically acceptable salt, amide or ester thereof.

80. A method for determining selectivity of a compound comprising the following steps:
   measuring the maximal AKT phosphorylation induced by said compound relative to human insulin
   measuring the maximal ERK activation induced by compound A relative to human insulin,
   wherein the ERK/AKT ratio is less than 1.

81. The method of embodiment 80, wherein said compound is an insulin compound.

82. The method of embodiment 81, wherein said insulin compound is a compound of embodiments 1-58.

EXAMPLES

Pharmacological Methods
Assay (I) In Vitro Biology
Insulin Receptor Binding

The relative binding affinity of the insulin derivatives of the invention for the human insulin receptor (IR) was determined by competition binding in a scintillation proximity assay (SPA) (according to Glendorf T et al; Biochemistry 2008 47 4743-4751).

In brief, dilution series of a human insulin standard and an insulin derivative were performed in 96-well plates followed by the addition of SPA beads (Anti-Mouse polyvinyltoluene SPA Beads, GE Healthcare), anti-IR mouse antibody 83-7 (can be purchased from e.g. Thermo Fisher Scientific), solubilised human IR-A (purified from Baby Hamster Kidney (BHK) cells overexpressing IR-A), and [$^{125}$I-TyrA14]-human insulin in binding buffer. After incubation, plates were centrifuged and counted on a TopCount NXT (Perkin-Elmer Life Sciences).

Data from the SPA were analysed according to the four-parameter logistic model (Vølund A; Biometrics 1978 34 357-365), and the binding affinities of the analogues were calculated relative to that of the human insulin standard measured within the same plate.

The relative binding affinities of insulin derivatives representative for the invention are listed in Table 1, below. FIG. 1 shows representative receptor binding curves for human insulin and Compound of example 15 from a competition binding assay with solubilised IR-A.

Insulin Receptor Phosphorylation (IRpY1158)

The effect of the insulin derivatives of this invention on activation of the insulin receptor (IR) was assessed by the ability of the insulin derivatives to phosphorylate the tyrosine residue in position 1158 of the insulin receptor, as described by Hansen B F et al; PLOS One May 2012 7 e34274.

In brief, CHO-hIR cells (Chinese hamster ovarian cells overexpressing the insulin receptor-A) were stimulated with increasing concentrations of insulin analogues for 30 min, washed in ice-cold phosphate buffered saline (PBS), snap-frozen and lysed in lysis buffer. Equal amounts of protein were loaded into Phospho-IR-ELISA wells (IRpY1158), and phosphorylation measured according to the manufacturer's protocol (Invitrogen).

The maximum response of an insulin derivative of the invention on insulin receptor phosphorylation level was determined by measuring the insulin receptor phosphorylation level in the presence of increasing amounts of said insulin derivative to obtain a dose-response curve. A standard dose-response curve was defined by four parameters: the baseline response (Bottom), the maximum response (Top), the slope, and the drug concentration that provokes a response halfway between baseline and maximum (EC50).

Insulin receptor phosphorylation data dose-response curves was fitted by non-linear regression (four-parameter model (Y=Bottom+(Top-Bottom)/(1+10^((Log EC50-X)*HillSlope))) using GraphPad Prism 7 from GraphPad Software Inc. The estimated parameters estimated was used to calculate the % max value for each ligand as (Top(analogue)−Bottom(analogue))*100/(Top(insulin)−Bottom(insulin)).

Figure 2:
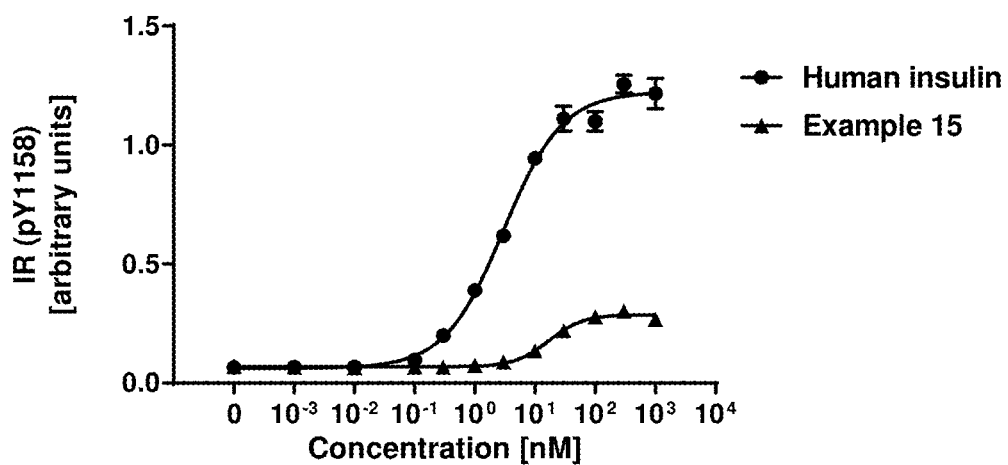
FIG. 2 shows representative dose-response curves for human insulin (●) and compound of example 15 (▲) from an IRpY1158 phosphorylation assay in CHO-hIR cells overexpressing the IR-A.

Calculated % max values of insulin derivatives representative for the invention are listed in Table 1, below. FIG. 2 shows examples of such dose-response curves for human insulin and compound of example 15 from an IRpY1158 phosphorylation assay in CHO-hIR cells overexpressing the IR-A.

Thus from FIGS. 1 and 2 it can be seen how a compound representative of the invention, i.e. compound of example 15, was fully capable of displacing human insulin from the insulin receptor (FIG. 1), but only induces submaximal phosphorylation of the insulin receptor (FIG. 2.).

Insulin Receptor Signalling

Insulin receptor (IR) signalling of the analogues of this invention via AKT and ERK pathways was assessed either by traditional Western blotting technique or by the use of Surefire, alphascreen technique.

Western Blotting

In brief, CHO-hIR cells were stimulated for 10 min with increasing concentrations of the insulin analogue, washed in ice-cold PBS, snap-frozen and lysed in lysis buffer (Bio-source). Equal amounts of proteins were loaded on gels and blotted to nitrocellulose membranes. Phosphorylated AKT and ERK were visualised with Phospho-AKT (Ser473) (Cell signalling #9271) and pMAPK 44/42 ERK1/2 rabbit (Cell Signalling #4376) antibodies, respectively. Band intensities were evaluated using a LAS3000 (Fuji).

Surefire

Cells were plated in 96 well tissue culture plate, and the day after stimulated with insulin or insulin derivatives for 10 min at 37° C. and analyses according to manufactures protocol (AKT1/2/3 (p-Ser473) cat #TGRA4S10K and ERK1/2 p-T202/Y204 Cat #TGRESB10K)

The responsiveness value (Span) for each analogue was calculated using non-linear regression in GraphPad Prism 7 from GraphPad Software Inc and expresses as percent of the responsiveness of insulin (% max AKT or % max ERK)

Figure 3:
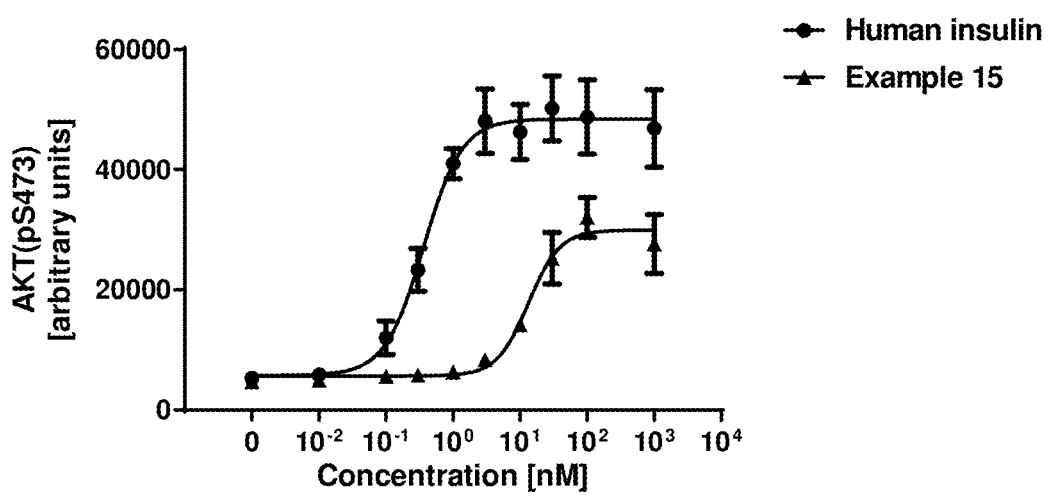
FIG. 3 shows representative dose-response curves for human insulin (●) and compound of example 15 (▲) from an AKT phosphorylation assay (phosphorylation of serine residue number 473) in CHO-hIR cells overexpressing the IR-A.
Figure 4:
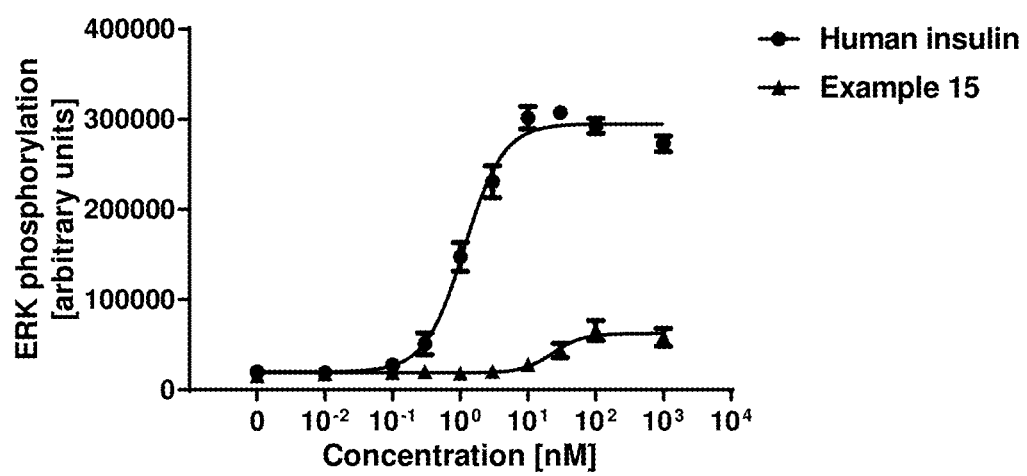
FIG. 4 shows representative dose-response curves for human insulin (●) and compound of example 15 (▲) from an ERK phosphorylation assay in CHO-hIR cells overexpressing the IR-A.

FIGS. 3 and 4 show representative dose-response curves for human insulin and Compound of example 15 from an AKT phosphorylation assay and an ERK phosphorylation assay in CHO-hIR cells overexpressing the IR-A and show how a compound representative of the invention, i.e. Compound of example 15, induces a lower submaximal activation of ERK than of AKT compared to human insulin. Calculated (% max ERK/% max AKT) values of insulin analogues representative for the invention and reference insulin derivatives are listed in Table 1.

The results given in Table 1 show that only the insulin derivatives which induce insulin receptor phosphorylation less than 65% of the maximum response induced by human insulin have a lower submaximal effect on ERK activation (phosphorylation) than on AKT activation (phosphorylation), when compared to the effect of human insulin.

Potency in Rat Free Fat Cell Assay (Lipogenesis)

The metabolic potency of the insulin derivatives of the invention was determined by lipogenesis using isolated rat adipocytes. The assays were carried out largely as described by Moody A J et al; Horm Metab Res 1974 6 12-16 (a modified version of the assay described in Rodbell M; J Biol Chem 1964 239 375-380).

In brief, epididymal fat pads were removed from killed Sprague-Dawley rats and placed in degradation buffer with collagenase (Worthington) in order to degrade the fat pads into a single-cell suspension. The cell suspension was washed with PBS and cells re-suspended in Krebs buffer supplied with 0.1 or 1% HSA (A-1887, Sigma) and HEPES. Cell suspension aliquots were incubated with glucose solution containing D-[3-$^3$H]glucose (PerkinElmer) and increasing concentrations of human insulin standard or insulin derivative. The incubation was stopped by addition of MicroScint-E (PerkinElmer), and the plates counted in a TopCount NXT (PerkinElmer).

The data were analysed according to the four-parameter logistic model (Vølund A; Biometrics 1978 34 357-365) and the metabolic potencies of the analogues were calculated relative to that of the human insulin standard measured within the same plate.

Figure 5:
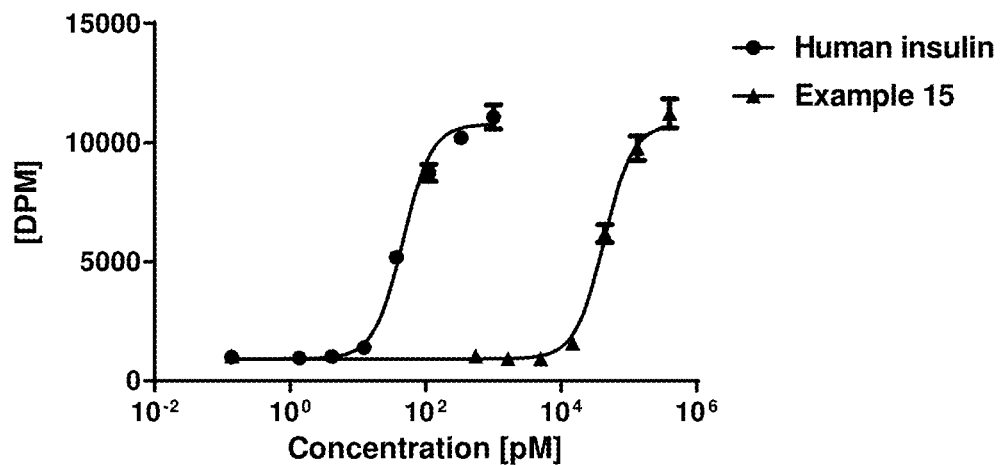
FIG. 5 shows representative dose-response curves for human insulin (●) and compound of example 15 (▲) from a lipogenesis assay in primary rat adipocytes (DPM=disintegrations per minute)

The metabolic potencies of the insulin derivatives representative for the invention are listed in Table 1, below. FIG. 5 shows a compound representative of the invention, i.e. compound of example 15, have the same maximum effect as human insulin on stimulating lipogenesis in primary rat adipocytes.

Isolation of Rat Hepatocytes

Rat hepatocytes were isolated from male Sprague-Dawley rats by retrograde perfusion of the liver with collagenase (Sigma) using a modified version of Berry M N and Friend D S; J Cell Biol 1969 43 506-520.

Hepatocytes were washed in Media 199 (Gibco) supplemented with human insulin, dexamethasone and foetal calf serum (Gibco), seeded on collagen-coated plates (BD Bio-Coat, BD Biosciences) and allowed to attach for 1-4 hours.
Stimulation of Glycogen Synthesis in Primary Rat Hepatocytes The effect of the insulin analogues of this invention on stimulation of glycogen accumulation was determined in primary hepatocytes (see isolation procedure above) using a specific and simple enzymatic method named PAS (Periodic Acid-Schiff) assay adapted from M. Kilcoyne et al., Analytical Biochemistry 416 (2011) 18-26. This method is an adaptation of the PAS reagent staining for a microtiter plate colorimetric assay. Primary rat hepatocytes were cultured in 96-well plates with varying human insulin or insulin derivative concentrations for 18-24 hours. To determine cellular glycogen content, the hepatocytes were lysed in 1% Triton for 30 minutes in a shaker at room temperature. Periodic acid solution (0.1% Periodic Acid+7% acetic acid in MQ water) (Periodic Acid 3951, Sigma) was added to each well and mix with shaker for one min. Plates were then incubated for 90 min. at 37° C. allowing oxidization of the hydroxyl groups of glucose to aldehydes. Then Schiff's solution was added and the plate was protected from the light, shaken for 5 min. before letting them stand for 25 min. at room temperature. Absorbance at 550 nm was then measured using a SpectraMax spectrophotometer. Data were analysed in GraphPad Prism 7 and the relative metabolic potency of the insulin analogue calculated as the ratio between the estimated EC50 values for human insulin and the insulin analogue.

Figure 6:
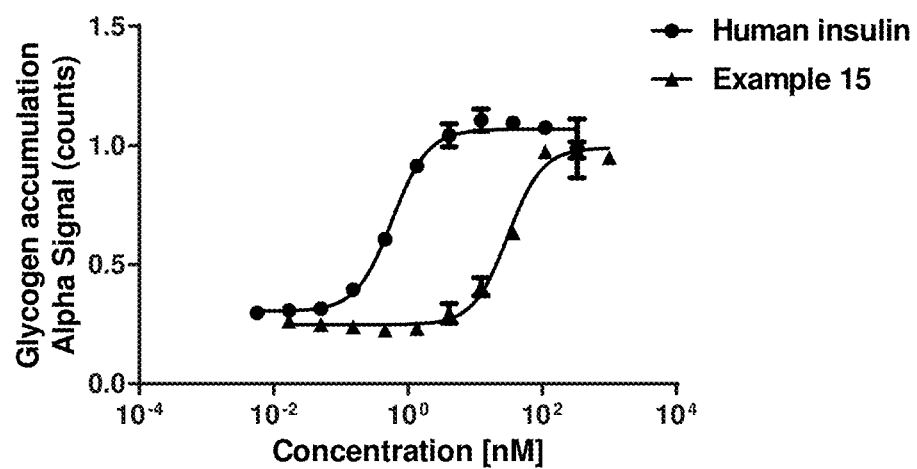
FIG. 6 shows representative dose-response curves for human insulin (●) and compound of example 15 (▲) from a glycogen synthesis assay in primary rat hepatocytes.

The potencies of the insulin derivatives representative for the invention on glycogen accumulation in hepatocytes are listed in Table 1, below. FIG. 6 a compound representative of the invention, i.e. compound of example 15, has the same maximum effect as human insulin on the stimulation of glycogen accumulation in primary rat hepatocytes.
Gene Expression The effect of the insulin derivatives of this invention on gene expression was determined by quantitative real-time polymerase chain reaction (RT-PCR) on cDNA isolated from primary rat hepatocytes (see isolation procedure above).

One day after isolation, hepatocytes were treated with glucagon for two hours in assay Media 199 (Gibco) supplemented with 1 µM dexamethasone and 0.1% HSA (A-1887, Sigma). After pre-incubation, cells were treated with human insulin or insulin derivative in assay media for 16 hours, changing to fresh media after 2, 4 and 6 hours.

RNA was extracted and purified from hepatocytes using RNeasy Mini Kit (Qiagen). cDNA was produced from RNA using iScript cDNA Synthesis Kit (Bio-Rad). Gene expression was determined using TaqMan Fast Advanced Master mix and primer/probe on demand (Applied BioSystems; Ppib #Rn03302274_m1 rFAS #Rn00565347_m1; rG6Pc #Rn00565347_m1). Gene expression was normalised to expression of Ppip (cycB, cyclophilin b) and fitted to a sigmoidal dose-response curve using GraphPad Prism 7 from GraphPad Software Inc.

Figure 7:
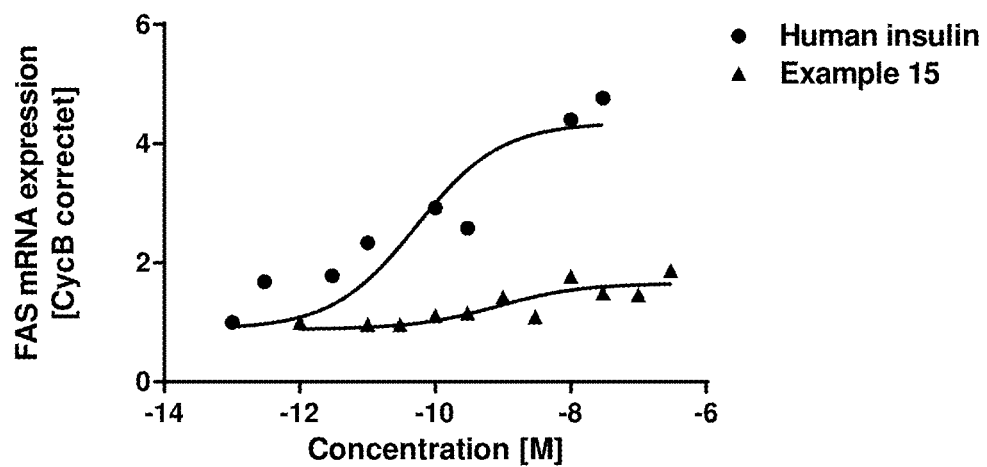
FIG. 7 shows representative dose-response curves for human insulin (●) and compound of example 15 (▲) from a quantitative real-time polymerase chain reaction (RT-PCR) assay for fasn performed on cDNA isolated from primary rat hepatocytes.
Figure 8:
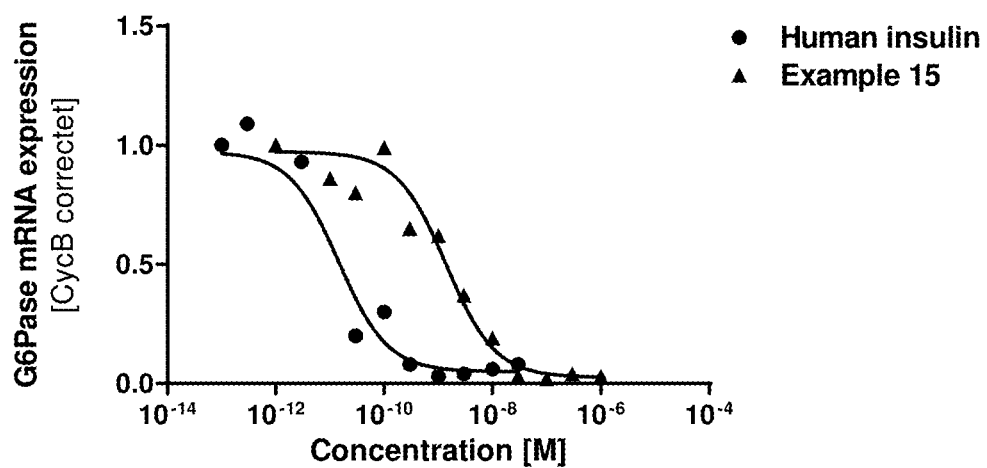
FIG. 8 shows representative dose-response curves for human insulin (●) and compound of example 15 (▲) from a quantitative real-time polymerase chain reaction (RT-PCR) assay for g6pc performed on cDNA isolated from primary rat hepatocytes.

FIGS. 7 and 8 show representative dose-response curves for human insulin and Compound of example 15, from quantitative RT-PCR assays for fasn and g6pc performed on cDNA isolated from primary rat hepatocytes. The results given in FIG. 7 show how a compound representative of the invention, i.e. compound of example 15, induces a submaximal induction of FAS mRNA, when compared to human insulin.

FIG. 8 show a compound representative of the invention, i.e. compound of example 15, inhibits the expression of G6Pc RNA to the same level as human insulin in primary rat hepatocytes.
De Novo Lipogenesis The effect of the insulin derivatives of this invention on de novo synthesis of lipids (DNL) was determined in primary hepatocytes (see isolation procedure above) using labelled acetate.

One day after isolation, hepatocytes were pre-incubated in assay media (Media 199 (Gibco), HSA (Sigma)) supplemented with glucose (Sigma) and human insulin or insulin derivative for 24 hours. After pre-incubation, hepatocytes were treated in assay media with human insulin or insulin derivative and $^{14}C$-labelled acetate (PerkinElmer) for 24h hours. After incubation, cells were washed in PBS and lysed with MicroScint-E (PerkinElmer).

Figure 9:
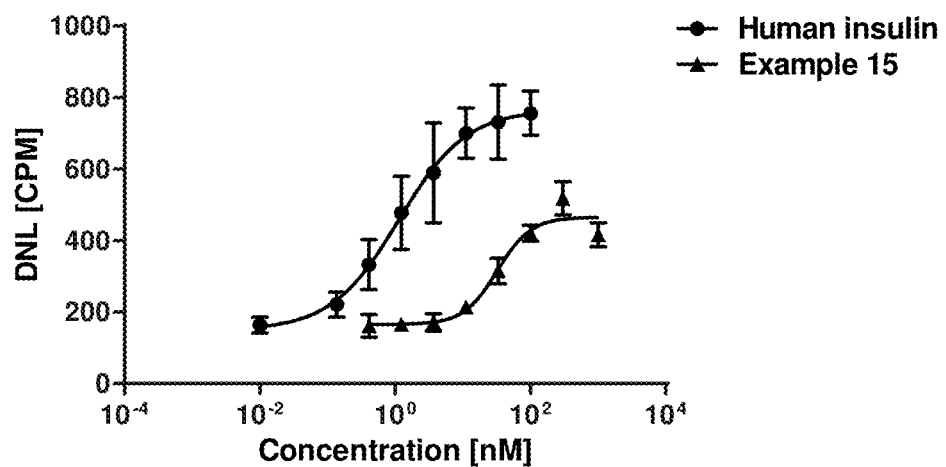
FIG. 9 shows representative dose-response curves for human insulin (●) and compound of example 15 (▲) from a de novo lipogenesis assay in primary rat hepatocytes (CPM=counts per minute)
Figure 10:
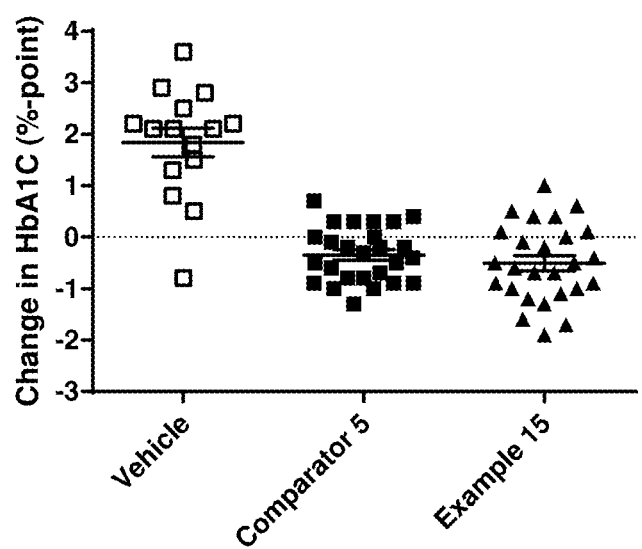
FIG. 10 shows representative curves for HbA1c levels from a sub-chronic in vivo study in diabetic STZ-DIO mice dosed subcutaneously twice daily for six weeks with vehicle, the PK Comparator (comparator no. 5) and compound of example 15.
Figure 11:
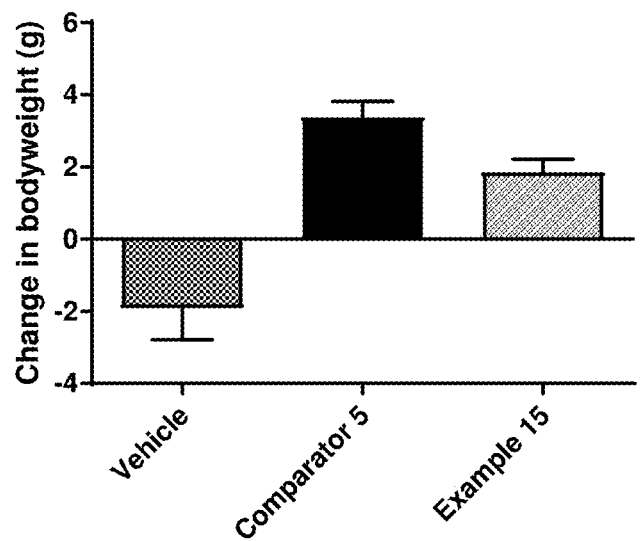
FIG. 11 shows representative curves for body weight from a sub-chronic in vivo study in diabetic STZ-DIO mice dosed subcutaneously twice daily for six weeks with vehicle, the PK Comparator (comparator no. 5) and compound of example 15.
Figure 12:
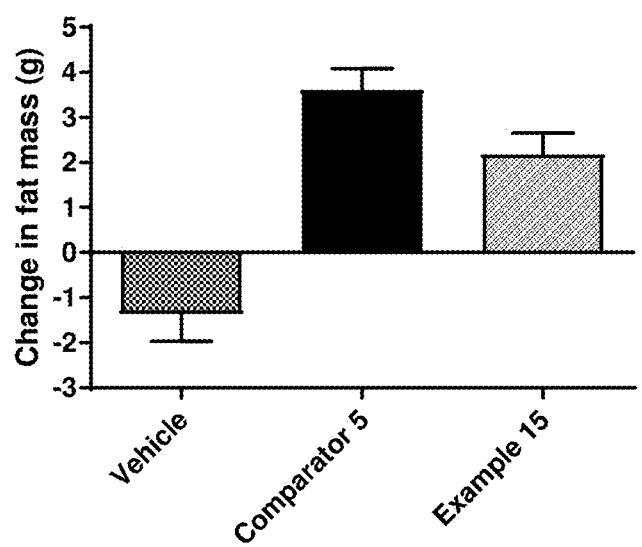
FIG. 12 shows representative curves for body fat mass from a sub-chronic in vivo study in diabetic STZ-DIO mice dosed subcutaneously twice daily for six weeks with vehicle, the PK Comparator (comparator no. 5) and compound of example 15.
Figure 13:
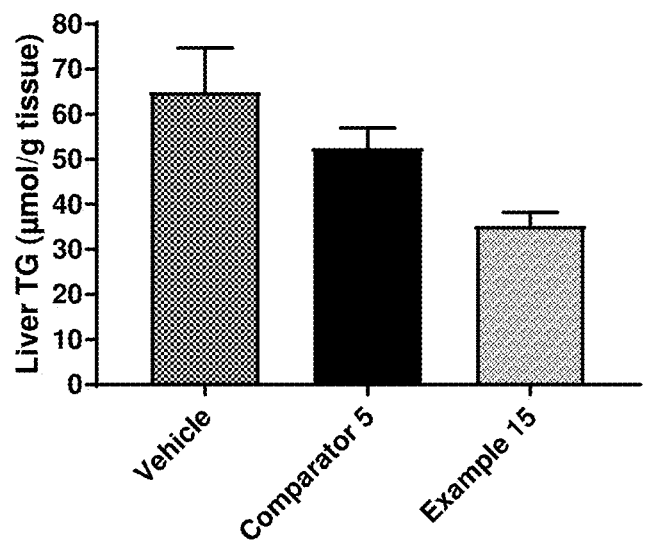
FIG. 13 shows representative curves for liver TG from a sub-chronic in vivo study in diabetic STZ-DIO mice dosed subcutaneously twice daily for six weeks with vehicle, the PK Comparator (comparator no. 5) and compound of example 15.
Figure 14:
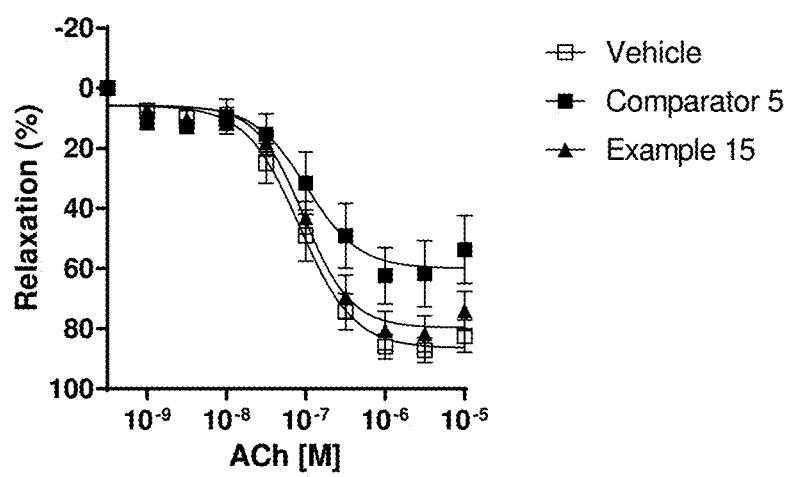
FIG. 14 shows representative curves for ACh-stimulated vasorelaxation of mesenteric arteries from a sub-chronic in vivo study in diabetic STZ-DIO mice dosed subcutaneously twice daily for six weeks with vehicle, the PK Comparator (comparator no. 5) and compound of example 15.

Incorporation of radioactive acetate into lipids (DNL) was determined using a TopCount NXT (PerkinElmer Life Sciences) and the results fitted to a sigmoidal dose-response curve using GraphPad Prism 7 from GraphPad Software Inc. FIG. 9 shows representative dose-response curves for human insulin and compound of example 15 from a de novo lipogenesis assay in primary rat hepatocytes and show how a compound representative of the invention, i.e. compound of example 15, exhibits a submaximal response on the de novo lipogenesis in primary rat hepatocytes.

TABLE 1A

In vitro biological activity

| Compound of Example no. | hIR binding IC50 (% of human insulin) | Lipogenesis 0.1% HSA EC50 (% of human insulin) | Lipogenesis 0.1% HSA EC50 (% of human insulin) | Elisa hIR pY1158 max (% of human insulin) | % maxERK/ % maxAKT |
|---|---|---|---|---|---|
| 1 | 8 | 0.82 | 0.15 | 32 | 0.38 |
| 2 | 10 | 0.86 | 0.21 | 43 | 0.47 |
| 3 | 8 | 0.04 | 0.01 | 17 | 0.35 |
| 4 | 4 | 0.14 | 0.07 | 19 | 0.37 |
| 5 | 8 | 0.14 | 0.07 | 31 | 0.48 |
| 6 | 5 | 0.14 | 0.06 | 36 | 0.45 |
| 7 | 9 | 0.20 | 0.09 | 39 | 0.61 |
| 8 | 10 | 1.76 | 0.72 | 25 | 0.32 |
| 9 | 12 | 0.40 | 0.49 | 14 | 0.29 |
| 10 | 14 | 0.68 | 0.11 | 10 | 0.27 |
| 11 | 10 | 0.05 | 0.02 | 3 | 0.07 |
| 12 | 12 | 0.10 | 0.02 | 10 | 0.25 |
| 13 | 10 | 0.26 | 0.05 | 11 | 0.15 |
| 14 | 10 | 0.26 | 0.05 | 16 | 0.25 |
| 15 | 10 | 0.29 | 0.09 | 16 | 0.25 |
| 16 | 7 | 0.08 | 0.05 | 20 | 0.38 |
| 17 | 7 | 0.18 | 0.16 | 37 | 0.53 |
| 18 | 6 | 0.32 | 0.26 | 14 | 0.35 |
| 19 | 7 | 0.04 | 0.02 | 15 | 0.21 |
| 20 | 20 | 0.34 | 0.14 | 23 | 0.23 |
| 21 | 12 | 0.39 | 0.43 | 37 | 0.54 |
| 22 | 17 | 0.21 | 0.15 | 26 | 0.36 |
| 23 | 23 | 0.29 | 0.17 | 28 | 0.36 |
| 24 | 34 | 0.39 | 0.21 | 30 | 0.42 |
| 25 | 15 | 0.14 | 0.12 | 26 | 0.50 |
| 26 | 14 | 0.50 | 0.24 | 21 | 0.37 |
| 27 | 19 | 0.11 | 0.09 | 35 | 0.47 |
| 28 | 15 | 0.24 | 0.16 | 12 | 0.30 |
| 29 | 16 | 0.37 | 0.17 | 17 | 0.32 |
| 30 | 12 | 0.17 | 0.11 | 14 | 0.25 |
| 31 | 12 | 0.26 | 0.20 | 7 | 0.34 |
| 32 | 4 | 0.12 | 0.05 | 32 | 0.40 |
| 33 | 7 | 0.08 | 0.05 | 6 | 0.20 |
| 34 | 3 | 0.09 | 0.03 | 27 | 0.27 |
| 35 | 4 | 0.02 | 0.01 | 10 | 0.31 |

TABLE 1A-continued

In vitro biological activity

| Compound of Example no. | hIR binding IC50 (% of human insulin) | Lipogenesis 0.1% HSA EC50 (% of human insulin) | Lipogenesis 0.1% HSA EC50 (% of human insulin) | Elisa hIR pY1158 max (% of human insulin) | % maxERK/ % maxAKT |
|---|---|---|---|---|---|
| 36 | 9 | 0.03 | 0.01 | 10 | 0.26 |
| 37 | 6 | 0.01 | 0.01 | 2 | ND |
| 38 | 4 | 0.03 | 0.01 | 6 | 0.33 |
| 39 | 4 | 0.05 | 0.01 | 24 | 0.41 |
| 40 | 11 | 1.42 | 0.16 | 58 | 0.84 |
| 41 | 3 | 0.22 | 0.16 | 40 | 0.66 |
| 42 | 12 | 2.21 | 0.41 | 8 | 0.19 |
| 43 | 7 | 1.08 | 0.32 | 13 | 0.30 |
| 44 | 8 | 0.09 | 0.02 | 7 | 0.36 |
| 45 | 4 | 0.13 | 0.08 | 6 | 0.29 |
| 46 | 3 | ND | 0.03 | 20 | 0.27 |

ND: Not determined

TABLE 1B

In vitro biological activity for comparators

| Comparator compound | hIR binding IC50 (% of human insulin) | Lipogenesis 0.1% HSA EC50 (% of human insulin) | Lipogenesis 1% HSA EC50 (% of human insulin) | Elisa hIR pY1158 max (% of human insulin) | % maxERK/ % maxAKT |
|---|---|---|---|---|---|
| Human insulin | 100 | 100 | 100 | 100 | 1 |
| Comparator no. 1 | 47 | 71 | 56 | 93 | 0.84 |
| Comparator no. 2 | 27 | 44 | 43 | 93 | 0.82 |
| Comparator no. 3 | 54 | 37 | 35 | 132 | 0.85 |
| Comparator no. 4 | 45 | 58 | 39 | 95 | 0.84 |
| Comparator no. 5 PK comparator used in Assay (II) | 13 | ND | 0.7 | 69 | 0.81 |
| Insulin lispro | 119 | ND | ND | 104 | 0.85 |
| Insulin aspart | 83 | ND | ND | 95 | 0.79 |
| Insulin degludec | 20 | 3.8 | 0.8 | 87 | 0.97 |
| Insulin glargine | 79 | ND | 68.9 | 104 | 0.85 |

Assay (II) Subchronic In Vivo Study with Diabetic Mice

Animals and Compounds 12-week old male C57BL/6J-Diet-Induced Obese (D10) mice from Jackson Laboratory, on Research Diet D12492 high-fat chow, were habituated for two weeks in the facilities, and then, under brief isoflurane gas anaesthesia, made diabetic by subcutaneous (s.c.) injection of 150 mg/kg streptozotocin (STZ) (Sigma). The animals were allowed two weeks to develop stable diabetes, before being assigned to treatment groups based on measurements of body weight, blood glucose levels, and blood glycosylated haemoglobin (HbA1c) levels. The animals were housed under standard lighting and temperature conditions, and had ad lib access to the D12492 diet and water at all times.

Animals were assigned to either vehicle treatment (n=16), or to different doses of either the PK Comparator (comparator no. 5) or compound of example 15 (n=26 per dose group).

The test compounds, i.e. the PK Comparator (comparator no. 5) and compound of example 15, were formulated in 5 mM phosphate, 140 mM sodium chloride, and 70 ppm polysorbate-20.

The PK Comparator (comparator no. 5) is an acylated, but non-partial insulin derivative.

Treatment Protocol

The animals were treated for six weeks, with twice-daily s.c. injections with their assigned treatment. Injections were given 12 hours apart, in the time frames 07:30-08:30 and 19:30-20:30 every day. The dosing volume was 2 mL/kg, and the injections were administered with a NovoPen® injection device.

Throughout the study, the animals were regularly measured for body weight and blood glucose levels, and blood HbA1c levels and body composition was measured at start and at completion of the study. Furthermore, the plasma exposure level of the PK Comparator (comparator no. 5) and compound of example 15 was assessed.

Analytical Methods

Blood glucose concentrations were determined by diluting whole blood in EBIO buffer solution, followed by measurement on an EKF Diagnostic Biosen autoanalyser.

Blood HbA1c levels were determined by diluting whole blood in hemolysing buffer, followed by measurement on a Hitachi Cobas 6000 autoanalyser, and by using a Roche Diagnostics HbA1c kit.

Body composition was determined by scanning un-anaesthetised mice for fat mass and lean mass by quantitative magnetic resonance (EchoMRI-100™, Echo Medical Systems).

The liver TG content was determined in samples of liver tissue, collected immediately after euthanasia. After homogenization, saponification and centrifugation of the liver sample, the TG concentration was measured in the supernatant on a Hitachi Cobas 6000 Analyzer (Roche). The TG content was then divided with the mass of the original homogenized liver sample and expressed as pmol TG per mg liver tissue.

Endothelial function was assessed ex vivo in HbA1c matched groups (vehicle n=12, PK Comparator (comparator no. 5) n=15 and compound of example 15 (n=15) using ACh-induced vasorelaxation in mesenteric arteries mounted in a wire myograph. The arteries were pre-constricted to 70% of maximal tone with phenylephrine followed by stimulation with ACh in cumulatively increasing doses.

Plasma exposure levels of the PK Comparator (comparator no. 5) and compound of example 15, were determined by analysis of plasma samples using in-house luminescent oxygen channelling immunoassays (LOCI).

FIG. 10-14 show representative curves for HbA1c levels, body weight, body fat mass, liver TG and ACh-stimulated vasorelaxation of mesenteric arteries from a sub-chronic in vivo study in diabetic STZ-DIO mice dosed subcutaneously twice daily for six weeks with vehicle, the PK Comparator (comparator no. 5), and an insulin analogue representative of the invention, i.e. compound of example 15.

The animal experiments showed that treatment of diabetic high-fat fed mice with insulin derivatives of the invention can lower blood glucose levels similarly to the pharmacokinetics (PK) Comparator (comparator no. 5). The PK Comparator (comparator no. 5) is an acylated insulin analogue that is not a partial agonist on insulin receptor phosphorylation, but with a PK profile in mice similar to that of compound of example 15 of the present invention.

Sub-chronic treatment (6 weeks) of diabetic, high-fat fed mice with an insulin derivative representative of the invention, i.e. compound of example 15, versus a PK Comparator (comparator no. 5) dosed to reach the same level of glycaemic control (measured by HbA1c levels), resulted in significantly less weight gain less increase in body fat mass, increased lowering of liver triglycerides (TG) and improved acetylcholine (ACh) stimulated vasorelaxation ex vivo.

Thus, the present invention provides insulin derivatives, which are capable of reducing blood glucose levels, but have improved effects on processes related to lipid metabolism, such as less weight gain, less increase in body fat mass and increased lowering of liver TG, as well as improved endothelial function relative to a PK-matched comparator.

LIST OF ABBREVIATIONS

ACh—Acetylcholine
AKT—Protein Kinase B (PKB)
BHK—Baby hamster kidney
CHO—Chinese hamster ovarian
CPM—Counts per minute
CVD—Cardiovascular diseases
DIO—Diet-induced obese
DNL—de novo lipogenesis
DPM—Disintegrations per minute
ELISA—Enzyme-linked immunosorbent assay
ERK—Extracellular regulated kinase (also known as MAPK)
FAS—Fatty acid synthase
G6Pc—Glucose-6-phosphatase
HbA1c—glycosylated haemoglobin
HEPES—4-(2-hydroxyethyl)-1-piperazineethanesulfonic acid
HI—Human insulin
HSA—Human serum albumin
IR—Insulin receptor
IR-A—Insulin receptor isoform A
LOCI—luminescent oxygen channelling immunoassays
MAPK—Mitogen-activated protein kinase (also known as ERK)
NAFLD—Non-alcoholic fatty liver diseases
PAS—Periodic acid solution
PBS—Phosphate buffered saline
PK—pharmacokinetics
PKB—Protein kinase B (also known as AKT)
Ppip—Cyclophilin b (cycB)
RT-PCR—real time polymerase chain reaction
SPA—scintillation proximity assay
SREPB1c—Sterol regulatory element-binding transcription factor 1c
STZ—streptozotocin
STZ-DIO—streptozotocin-treated diet-induced obese
TG—Triglycerides Stability The stability of the insulin derivatives of this invention were evaluated using Differential Scanning calorimetry (DSC) and Size Exclusion Chromatography (SEC)

Evaluation of Insulin Derivative Self-Association and Stability by Differential Scanning Calorimetry (DSC)

Formulation

The insulin derivatives were dissolved to about 0.2 mM and pH adjusted to around 7.6 with sodium hydroxide and hydrochloric acid. Concentration was determined by SEC Waters PROTEIN PAK 125 (250*8 mm) with an eluent containing 2.5 M acetic acid, 4 mM L-arginine and 20% (V/V) acetonitrile at a flow rate of 1 ml/min. and ambient temperature. Detection at 280 nm against a human insulin reference using absorption coefficient correction according to Pace.

For a final insulin derivative concentration of 0.1 mM was added, 16 mM phenol, 7 mM phosphate, 10 mM NaCl and 0.1 mM zinc acetate. pH was adjusted to 7.4 with hydrochloric acid and sodium hydroxide.

Data collection was performed using a MicroCal VP-Capillary DSC (Malvern Instruments Ltd). All scans were performed with a vehicle (same composition as the insulin samples but without insulin and zinc acetate) in the reference cell from 20° C. to 110° C. at a scan rate of 4° C./min. Instrument feedback mode set at "low" and data filtering period set at 2 seconds. A buffer-buffer reference scan (performed with the aforementioned vehicle) was subtracted from each sample scan prior to concentration normalization and baseline creation. It should be noted that the insulin zinc complex could be in other association states than hexameric with regards to insulin, but for the sake of simplification the zinc stabilized insulin complex is referred to as hexameric.

The ($T_{onset}$) and the midpoint of the hexamer unfolding peak ($T_{m,hexamer}$) were compared for different insulin derivatives and values of $T_{onset}$ and $T_{m,hexamer}$ are shown in Table 2. The results show how B5Tyr and B5Phe mutations have highly stabilizing effect on the insulin zinc hexamer.

TABLE 2

Stability data

| Compound | Tm, onset (° C.) | Tm, hexamer (° C.) | SEC, % ≥ hexamer 3Zn/6ins | SEC, % ≥ hexamer 6Zn/6ins |
|---|---|---|---|---|
| Compound of Example 1 | 71.3 | 83.8 | 100 | 100 |
| Compound of Example 2 | 77.3 | 92.1 | ND | ND |
| Compound of Example 3 | 73.7 | 88.6 | 100 | 100 |
| Compound of Example 4 | 77.2 | 91.7 | 96.7 | 97.1 |
| Compound of Example 5 | 67.9 | 82.2 | 98.3 | 97.5 |
| Compound of Example 6 | 75.4 | 90.3 | 86.7 | 92.4 |
| Compound of Example 7 | 74.1 | 89 | ND | ND |
| Compound of Example 8 | 59.1 | 85 | 96.1 | 93 |
| Compound of Example 9 | 56.5 | 89.4 | 85.5 | 74.1 |
| Compound of Example 10 | 71.7 | 82.1 | 91.5 | 88.5 |
| Compound of Example 11 | 67 | 79.4 | 95.4 | 93.2 |
| Compound of Example 12 | 66 | 77.3 | 89.4 | 76.3 |
| Compound of Example 13 | 68.5 | 79.4 | 92.8 | 96.5 |
| Compound of Example 14 | 71.5 | 82.3 | 78.5 | 87.3 |
| Compound of Example 15 | 69.9 | 81 | 97.1 | ND |
| Compound of Example 16 | low signal | low signal | 78.7 | 51.4 |
| Compound of Example 17 | low signal | low signal | 21.7 | 71.1 |
| Compound of Example 18 | 64.3 | 76.9 | 90.4 | 90.1 |
| Compound of Example 19 | 60 | 73.6 | 80.7 | 74.2 |
| Compound of Example 20 | low signal | low signal | 88.1 | 76.3 |
| Compound of Example 21 | ND | ND | ND | ND |
| Compound of Example 22 | low signal | low signal | 93 | 68.6 |
| Compound of Example 23 | low signal | low signal | 42.5 | 44.1 |
| Compound of Example 24 | low signal | low signal | 26.8 | 26.9 |
| Compound of Example 25 | low signal | low signal | 52 | 67.1 |
| Compound of Example 26 | low signal | low signal | ND | ND |
| Compound of Example 27 | low signal | low signal | 18 | 42.5 |
| Compound of Example 28 | 67 | 78.5 | ND | ND |
| Compound of Example 29 | low signal | low signal | ND | ND |
| Compound of Example 30 | 68.9 | 79.7 | 95.4 | 98.9 |
| Compound of Example 31 | 67.9 | 97.7 | 91.7 | 86.5 |
| Compound of Example 32 | 67.2 | 78.4 | 76.9 | 89.7 |
| Compound of Example 33 | 67.4 | 98.2 | ND | ND |
| Compound of Example 34 | 67.7 | 78.9 | 84.4 | 89.6 |
| Compound of Example 35 | 67.6 | 91.4 | 91.4 | 91.4 |
| Compound of Example 36 | 68.5 | 80.6 | 95.9 | 92 |
| Compound of Example 37 | 60.8 | 74.1 | 74.2 | 64.7 |
| Compound of Example 38 | 70.1 | 101.8 | ND | ND |
| Compound of Example 39 | 76.3 | 97.3 | ND | ND |
| Compound of Example 40 | 90.7 | 103.1 | ND | ND |
| Compound of Example 41 | 67.8 | 82.6 | ND | ND |

TABLE 2-continued

Stability data

| Compound | Tm, onset (° C.) | Tm, hexamer (° C.) | SEC, % ≥ hexamer 3Zn/6ins | SEC, % ≥ hexamer 6Zn/6ins |
| --- | --- | --- | --- | --- |
| Compound of Example 42 | 71.1 | 84 | 90.2 | 97.4 |
| Compound of Example 43 | 71.8 | 82.7 | 89 | 97 |
| Compound of Example 44 | 71.2 | 82.9 | 89 | 81 |
| Compound of Example 45 | 73.6 | 84.3 | 86.2 | 80.5 |
| Compound of Example 46 | 72 | 102 | 82.7 | 79.9 |
| Insulin aspart | 52 | 72 | ND | ND |
| Comparator 1 | ND | ND | ND | ND |
| Comparator 2 | ND | ND | ND | ND |
| Comparator 3 | ND | ND | ND | ND |
| Comparator 4 | ND | ND | ND | ND |
| Comparator 5 | ND | ND | ND | ND |
| Comparator 6 | 56.6 | 75 | 100 | 78 |
| Comparator 7 | 44.5 | 68.8 | 100 | 90 |
| Comparator 8 | 59.5 | 79 | 100 | 96 |
| Comparator 9 | low signal | low signal | 45.1 | 77.6 |

ND: not determined

Evaluation of Insulin Derivative Self-Association by Size Exclusion Chromatography (SEC)

Size Exclusion Chromatography (SEC) is a common method to evaluate insulin derivative self-association.

Formulation

The insulin analogues were dissolved to about 2 mM and pH adjusted to 7.6 with sodium hydroxide and hydrochloric acid. Concentration was determined by SEC Waters PROTEIN PAK 125 (250*8 mm) with an eluent containing 2.5 M acetic acid, 0.065% L-arginine and 20% (V/V) acetonitrile at a flow rate of 1 ml/min. and ambient temperature. Detection at 280 nm against a human insulin reference using absorption coefficient correction according to Pace C N, [Pace C N, Protein Science (1995) 4, 2411-2433].

For a final insulin derivative concentration of 0.6 mM was added 1.6% glycerol, 30 mM phenol, 7 mM tris(hydroxymethyl)aminomethane and 0.3 mM zinc acetate. pH was adjusted with hydrochloric acid and sodium hydroxide to pH 7.6.

In order to simulate insulin derivative formulation condition the eluent included 16 mM phenol, 20 mM sodium chloride, and 10 mM tris(hydroxymethyl)aminomethane adjusted to pH 7.3 by hydrochloric acid. The column used was ACQUITY UPLC® BEH200 (150*4.6 mm, d=1.7 μm) from Waters Corporation, Milford, Mass., USA. Flow was 0.3 mL/min, injection volume 20 μL and ultraviolet detection at 286 nm. The column temperature was maintained at 23° C.

Figure 15:
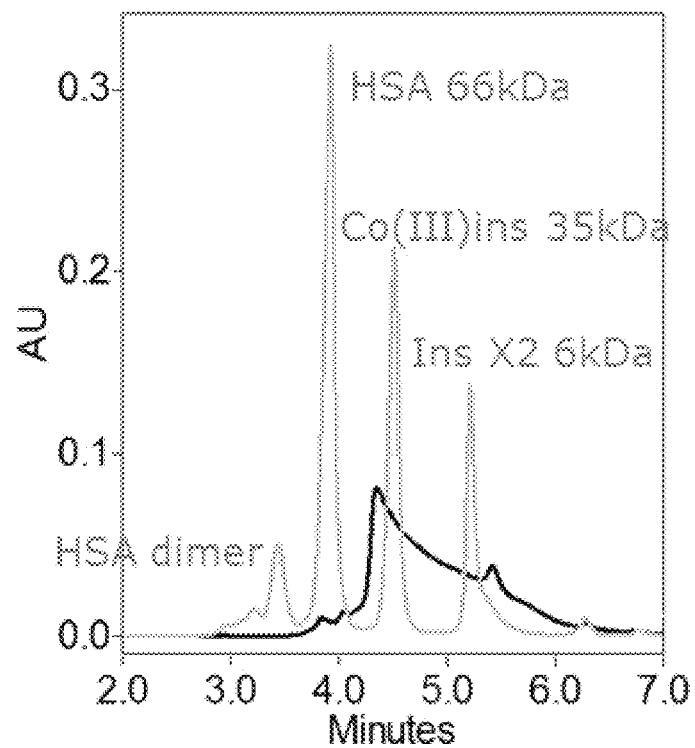
FIG. 15 shows representative SEC data for a formulation of 0.6 mM of a comparator compound i.e. comparator 9 (black line) including 3 Zn/6 ins, 30 mM phenol, 1.6% glycerol and 7 mM tris(hydroxymethyl)aminomethane at pH 7.6. A SEC reference mixture of human albumin, Co(III) insulin hexamer and a monomer insulin analogue (B9Asp, B27Glu) is included (grey line).
Figure 16:
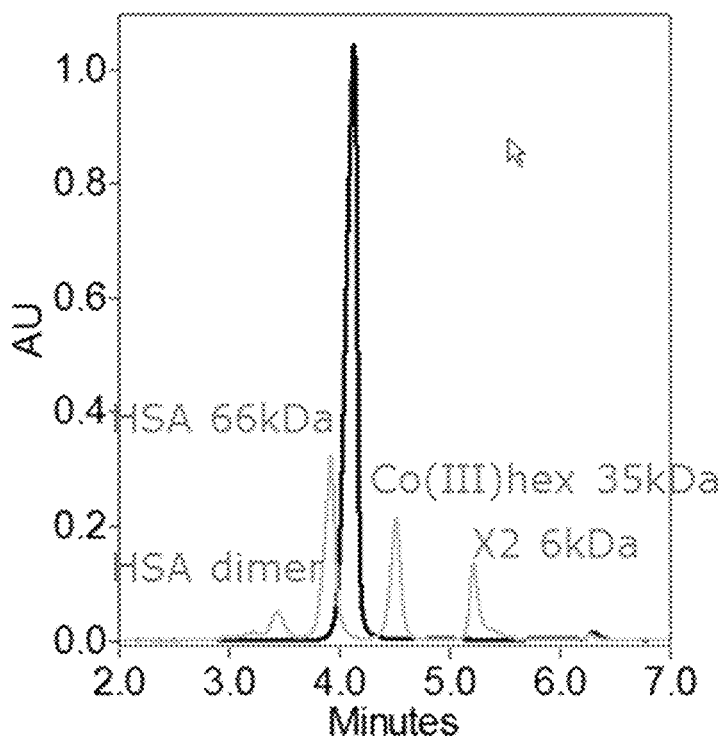
FIG. 16 shows representative SEC data of a similar formulation of compound of example 3 (black line).
Figure 17:
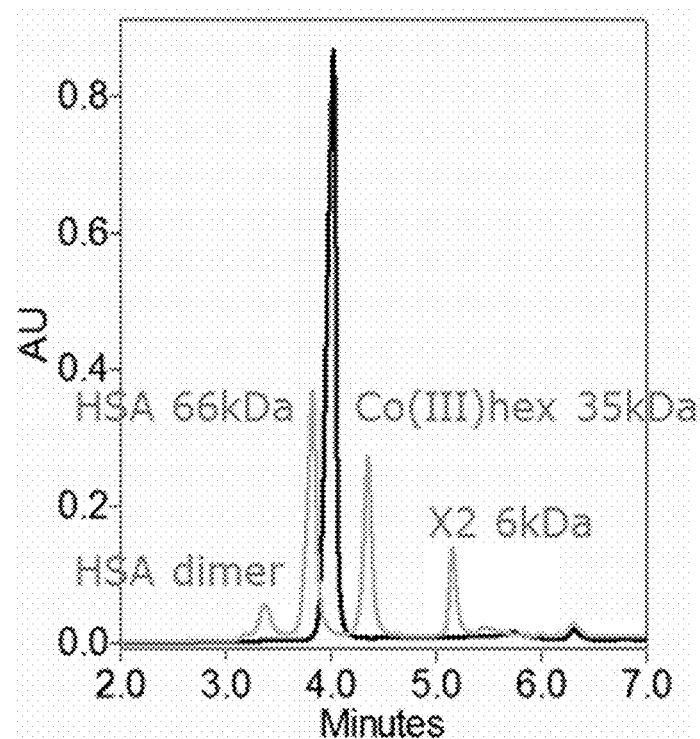
FIG. 17 shows representative SEC data of a similar formulation of compound of example 11 (black line).
Figure 18:
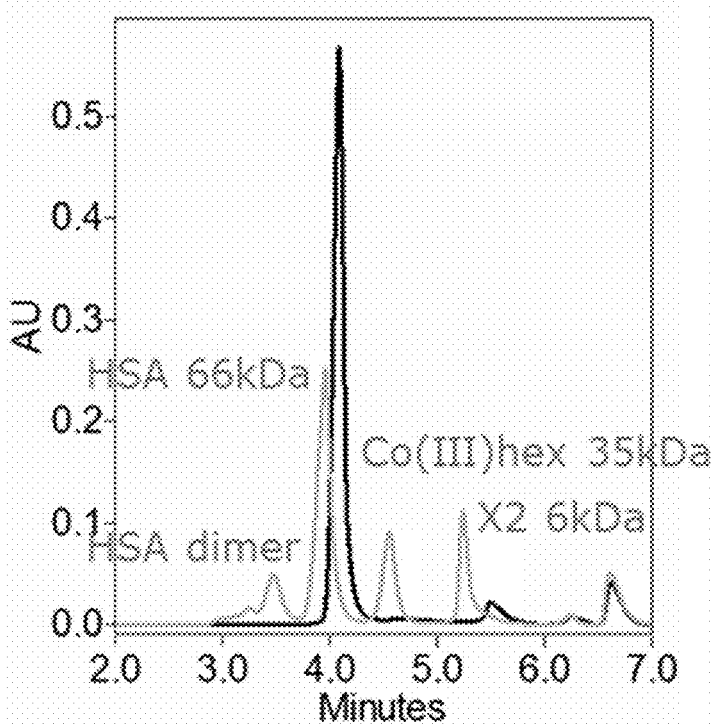
FIG. 18 shows representative SEC data of a similar formulation of compound of example 12 (black line)
Figure 19:
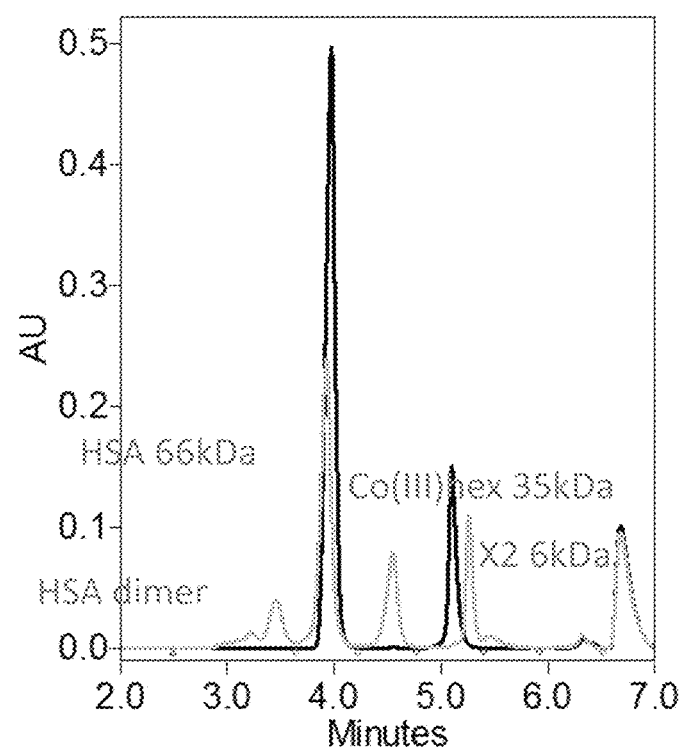
FIG. 19 shows representative SEC data of a similar formulation of compound of example 15 (black line).

FIG. 15-19 show representative chromatograms from SEC experiments. FIG. 15 shows how a comparator compound i.e. Comparator 9 was unstable in formulation since the various peaks are broad and tailing showing several overlapping self-association states. In contrast the results given in FIG. 16-19 show how compounds representative of the invention, i.e. compounds of Examples no. 3, 11, 12 and 15 are stable in formulation as the chromatograms showed a predominant single sharp peak.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

General Methods of Preparation

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention.

Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, i.e. by appropriate protection of interfering groups, by changing to other conventional reagents, or by routine modification of reaction conditions.

Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius, and unless otherwise indicated, all parts and percentages are by weight when referring to solids, and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns, etc. according to personal the preferences. Depending on factors such as impurity profile, solubility of the insulins in question etcetera, these modifications can readily be recognised and made by a person skilled in the art.

(Method 1) Preparative Example—Backbone Expression and Purification Backbone Expression The insulin peptide backbones, i.e. the two-chain nonacylated insulin analogues, for use according to the invention are produced recombinantly by expressing a DNA sequence encoding the insulin backbone in question in a suitable host cell by well-known techniques, e.g. as disclosed in U.S. Pat. No. 6,500,645. The insulin peptide backbone is either expressed directly or as a precursor molecule which may have an N-terminal extension on the B-chain and/or a connecting peptide (C-peptide) between the B-chain and the A-chain. This N-terminal extension and C-peptide are cleaved off in vitro by a suitable protease, e.g. *Achromobactor lyticus* protease (ALP) or trypsin, and will therefore have a cleavage site next to position B1 and A1, respectively. N-terminal extensions and C-peptides of the type suitable for use according to this invention are disclosed in e.g. U.S. Pat. No. 5,395,922, EP 765395 and WO 9828429 A1.

The polynucleotide sequence encoding the insulin analogue peptide backbone precursor for use according to the invention may be prepared synthetically by established methods, e.g. the phosphoamidite method described by Beaucage et al; *Tetrahedron Letters* 1981 22 1859-1869; or the method described by Matthes et al; *EMBO Journal* 1984 3 801-805. According to the phosphoamidite method, oligonucleotides are synthesised in e.g. an automatic DNA synthesiser, purified, duplexed, and ligated to form the synthetic DNA construct. A currently preferred way of preparing the DNA construct is by polymerase chain reaction (PCR).

The recombinant method will typically make use of a vector which is capable of replicating in the selected microorganism or host cell and which carries a polynucleotide sequence encoding the insulin peptide backbone precursor for use according to the present invention. The recombinant vector may be an autonomously replicating vector, i.e., a vector which exists as an extra-chromosomal entity, the replication of which is independent of chromosomal replication, e.g. a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector may be one capable of replicating in yeast. Examples of sequences which enable the vector to replicate in yeast are the yeast plasmid 2 μm replication genes REP 1-3 and origin of replication.

The vector may contain one or more selectable markers, which permit easy selection of trans-formed cells. A selectable marker is a gene the product, which provides for biocide or viral re-sistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (orni-thine carbamoyltransferase), pyrG (orotidine-5'-phosphate decarboxylase) and trpC (anthranilate syn-thase. Suitable markers for yeast host cells are ADE2, HIS3, LEU2, LYS2, MET3, TRP1, and URA3. A well suited selectable marker for yeast is the *Schizosaccharomyces pompe* TPI gene (Russell; *Gene* 1985 40 125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for di-recting the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, TDH3 or PGK promoters.

The polynucleotide sequence encoding the insulin peptide backbone for use according to the invention also will typically be operably connected to a suitable terminator. In yeast, a suitable terminator is the TPI terminator (Alber et al; *J. Mol. Appl. Genet.* 1982 1 419-434).

The procedures used to combine the polynucleotide sequence encoding the insulin peptide backbone for use according to the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin backbones for use according to the invention, and subsequently inserting this fragment into a suitable expression vector, or by sequentially inserting DNA fragments containing genetic information for the individual elements (such as the signal and pro-peptide (N-terminal extension of the B-chain), C-peptide, A- and B-chains), followed by ligation.

The vector comprising the polynucleotide sequence encoding the insulin backbone for use according to the invention is introduced into a host cell, so that the vector is maintained as a chromosomal integrant, or as a self-replicating extra-chromosomal vector. The term "host cell" encompasses any progeny of a parent cell that is not identical to the parent cell due to mutations that occur during replication. The host cell may be a unicellular microorganism, e.g. a prokaryote, or a non-unicellular microorganism, e.g. a eukaryote. Useful unicellular cells are bacterial cells such as gram positive bacteria including, but not limited to, a *Bacillus* cell, a *Streptomyces* cell, or a gram negative bacteria such as *E. coli* and *Pseudomonas* sp. Eukaryote cells may be mammalian, insect, plant, or fungal cells.

The host cell may in particular be a yeast cell. The yeast organism may be any suitable yeast organism which, on cultivation, secretes the insulin peptide backbone or the precursor hereof into the culture medium. Examples of suitable yeast organisms are include strains selected from *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation by known methods. The medium used to cultivate the cells may be any conventional medium suitable for growing yeast organisms.

Backbone Purification

The secreted insulin peptide backbone or precursor hereof may be recovered from the medium by conventional procedures including separating the yeast cells from the medium by centrifugation, by filtration or by catching the insulin peptide backbone or precursor hereof on an ion exchange matrix or on a reverse phase absorption matrix, precipitating the proteinaceous components of the supernatant, or by filtration by means of a salt, e.g. ammonium sulphate, followed by purification by a variety of chromatographic procedures, e.g. ion exchange chromatography, affinity chromatography, etc.

The purification and digestion of the insulin peptide backbones of this invention is carried out as follows:

The single-chain insulin peptide backbone precursor, which may contain an N-terminal extension of the B-chain and a modified C-peptide between the B-chain and the A-chain is purified and concentrated from the yeast culture supernatant by cation exchange (Kjeldsen et al; *Prot. Expr.*

*Pur.* 1998 14 309-316). The single-chain insulin peptide backbone precursor is matured into two-chain insulin peptide backbone by digestion with lysine-specific immobilised ALP (Kristensen et al; *J. Biol. Chem.* 1997 20 12978-12983) or by use of trypsin to cleave off the N-terminal extension of the B-chain, if present, and the C-peptide.

ALP Digestion

The eluate from the cation exchange chromatography step containing the insulin peptide backbone precursor is diluted with water to an ethanol concentration of 15-20%. Sodium glutamate is added to a concentration of 15 mM and pH is adjusted to 9.7 by NaOH. Immobilised ALP (4 gram/L) is added in a proportion of 1:100 (volume:volume) and digestion is allowed to proceed with mild stirring in room temperature overnight.

The digestion reaction is analysed by analytical LC on a Waters Acquity Ultra-Performance Liquid Chromatography system using a C18 column and the molecular weight is confirmed by matrix-assisted laser desorption ionisation time-of-flight (MALDI-TOF) mass spectrometry (MS) (Bruker Daltonics Autoflex II TOF/TOF).

The immobilised ALP is removed by filtration using a 0.2 µm filter. The two-chain insulin peptide backbone is purified by reversed phase HPLC (Waters 600 system) on a C18 column using an acetonitrile gradient. The desired insulin peptide backbone, i.e. B28K desB29-B30 human insulin, is recovered by lyophilisation.

Trypsin Digestion

The eluate from the cation exchange chromatography step containing the insulin peptide backbone precursor is diluted with water to an ethanol concentration of 15-20%. Glycine is added to a concentration of 50 mM and pH is adjusted to 9.0-9.5 by NaOH. Trypsin is added in a proportion of 1:300 (w:w) and digestion is allowed to proceed at 4 degrees. The digestion is analytically monitored every 20 minutes until digestion is completed. The digestion is terminated with addition of 1 M citric acid in a proportion of 3:100 (volume: volume).

The digestion reaction is analysed by analytical LC on a Waters Acquity Ultra-Performance Liquid Chromatography system using a C18 column and the molecular weight is confirmed by MALDI-TOF MS (Bruker Daltonics Autoflex II TOF/TOF).

The two-chain insulin peptide backbone is purified by reversed phase HPLC (Waters 600 system) on a C18 column using an acetonitrile gradient. The desired insulin peptide backbone, is recovered by lyophilisation.

Purity is determined by analytical LC on a Waters Acquity Ultra-Performance Liquid Chromatography system using a C18 column, and the molecular weight is confirmed by MALDI-TOF MS.

(Method 2) Preparative Example—Acylation and Purification Procedures Purification Procedures Purification Method 1
Column: Waters xBridge PrepC18, 30×250 mm
Flow: 20 ml/min
Buffer A: 0.1% TFA in water
Buffer B: 0.1% TFA in acetonitrile
Gradient: 20-45% B or 30-40% B or 20-60% B or 20-40% B or 25-50% B or 20-55% B or 30-45%6 over 40 min
Purification Method 2
Column: Phenomenex, 5u, C18, 110 Å, 30×250 mm
Flow: 20 ml/min
Buffer A: 0.1% TFA in water
Buffer B: 0.1% TFA in acetonitrile
Gradient: 10-60% B over 80 min or 0-60% B over 95 min or 25-55% B over 60 min General Procedure for the Preparation of Acylation Reagents Simple diacids: NHS-activated monoacids were either prepared by activating a diacid-mono-t-butyl ester with TSTU and DIPEA in NMP and used directly or the diacid-mono-NHS ester was prepared and isolated. When a tert-butyl protected acylation reagent was used the resulting insulin derivative was deprotected by treatment with TFA.

Diacids with OEG linkers: The reagent was made by stepwise solid phase synthesis on chlorotrityl resin using Fmoc-chemistry, and cleaved from the resin with HFIP, TFA, a HFIP/DCM mixture, or a TFA/DCM mixture.

Some acylation agents were prepared, isolated and used as NHS-esters without any protecting groups.

General Acylation Procedure 1

100 mg of the appropriate insulin analogue was dissolved in 1.2 ml 0.1 M Na2CO3 and 0.6 ml NMP and pH adjusted to 10.7±0.3. 0.03 mmol acylation reagent in 0.3 ml NMP was added at pH maintained at 10.7±0.3 by addition of 4 M NaOH if necessary. After 30 to 60 minutes the reaction was complete, and the product was precipitated by addition of 40 ml isopropanol, centrifuged, washed with ether and dried. Alternatively the product could be isolated by dilution with 30 ml water and adjustment of pH to 4.5-5.0 which lead to isoelectric precipitation. Alternatively the reaction mixture was acidified with acetic acid or TFA and purified immediately.

Subsequently, the product was purified by reverse phase high-performance liquid chromatography (RP-HPLC) in TFA-acetonitrile as described above and the pure fractions lyophilised. The identity of the product was confirmed by matrix-assisted laser desorption ionisation mass spectrometry (MALDI-MS or ultra-performance liquid chromatography (UPLC)/electrospray-MS.

In some cases the synthesis was scaled to produce larger or smaller amounts. In that case, all amounts of starting materials, reagents and solvents were scaled by the same factor Modification 1

When the acylation reagent contained a tert-butyl protecting group, the product after the isopropanol or isoelectric precipitation was dissolved in 5 ml TFA or TFA:water (95:5) for 5 minutes, precipitated with 35 ml ether, washed twice with ether and dried.

Modification 2

When the acylation reagent contained a tert-butyl protecting group, the crude iso-precipitated product was dissolved in 5 ml of TFA or TFA:water 95:5 or TFA:triisopropylsilane 99:1. The solution was stirred for 20-30 min, then diluted with water, in some cases additionally with either DMSO or NMF, and immediately purified by preparative HPLC.

Modification 3

In some cases where the acylation reagent appears to be poorly soluble in the reaction mixture, more NMP is added (up to 1 ml) and the reaction mixture warmed briefly to 37° C.

General Acylation Procedure 2

100 mg of the appropriate insulin was dissolved in 2 ml DMSO and 40 ul Bartons Base (2-t-butyl-1,1,3,3-tetramethylguanidine) was added. 20 umol of the acylating agent was added, and after one minute the reaction was complete. The reaction mixture was acidified and diluted into water and purified immediately.

(Method 3) Chemical Synthesis of Insulin Derivatives

Insulin A-chain was synthesized by standard Fmoc peptide synthesis, e.g. on a Prelude or Liberty synthesizer. Deprotection was performed with 10% or 20% piperidine in DMF. All protecting groups were standard, except that Cys 6, 11 and 20 had Trt protecting groups and Cys 7 had Acm. If the C-terminal residue was Asn, the peptide was synthesized on a PAL or Rink resin with Fmoc-Asp-OBut as the first amino acid.

After the synthesis, the resin was washed with DCM, treated with 1% iodine in DCM/HFIP (4:1) for 1 minute, and incubated in DCM/HFIP (4:1) for 15 minutes which lead to formation of the A6-A11 disulfide. After washing with DCM and drying, the peptide was cleaved with TFA/water/DPDS (93:5:2) which provided the insulin A-chain with pyridylsulfide on Cys20. Ether precipitation, washing, and drying lead to the crude A-chain which was used in subsequent chain combination.

Insulin B-chain was synthesized by standard Fmoc peptide synthesis, e.g. on a Liberty or Prelude synthesizer. The resin was e.g. a preloaded Wang resin. All protecting groups were standard, except that Cys7 had Acm and Cys19 had Trt.

Cleavage was performed with TFA/water/TIPS (93:4:3). Ether precipitation, washing, and drying lead to crude B-chain which was used in subsequent chain combination.

When an insulin derivative with a side chain modified lysine was desired, the modification was introduced during the peptide synthesis. The lysine to be modified was introduced as Fmoc-Lysine(Mtt)-OH and the N-terminal of the peptide protected with Boc (either by coupling of a Boc-protected amino acid in the last coupling step or by reaction of the resin bound peptide with 5 equivalents of Boc-anhydride in DMF). The Mtt group was removed by treating the resin with DMF/HFIP (1:4) for 30 minutes and the side chain was synthesized by standard Fmoc chemistry as described for the peptide backbone.

Crude A-chain and B-chain (0.14 mmol of each) was dissolved in 40 ml DMSO. 2 ml 2M Tris buffer pH 8.5 was added and the chain combination was complete in about 10 minutes. The solution was diluted with 40 ml DMSO and 200 ml 40% acetonitrile, 1% TFA. N-chlorosuccinimide was added to a final concentration of 5 mM. This formed the third disulfide bridge in less than 10 minutes. The solution was diluted and neutralized with 600 ml 0.2 M Tris pH 7.8 and purified by RP-HPLC on a C18 column running a gradient of acetonitrile in 20 mM phosphate pH 7.2.

Fractions containing the desired compound were combined and repurified on the same column with an acetonitrile gradient in 0.1% TFA. The pure fractions were combined and lyophilized. The yield was usually 20-50 mg of the desired insulin derivative which was subsequently characterized by UPLC and LC-MS.

Examples of Insulin Derivatives of the Invention

Example 1: N{Epsilon-B28}-15-carboxypentadecanoyl-[TyrB5,LysB28],des-(B29-B30)-Insulin]

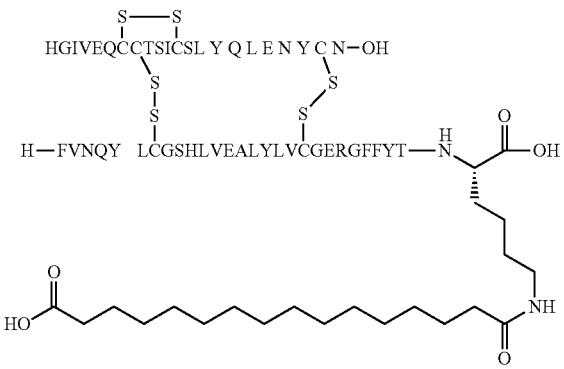

Synthesised by Synthesis Method 3.
Calc. Mass. = 5903.8; Found LC-MS m/4 = 1476.66

Example 2: N{Epsilon-B28}-[(4S)-4-carboxy-4-(15-carboxypentadecanoylamino)butanoyl]-[TyrB5,LysB28],des-(B29-B30)-Insulin Synthesised by Synthesis Method 3.

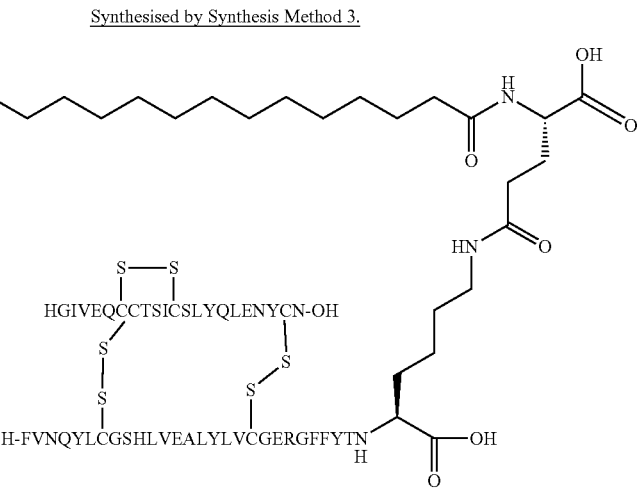

Calc.Mass. = 6032.9; Found LC-MS m/4 = 1509.07

Example 3: N{Epsilon-B28}-17-carboxyheptadecanoyl-[TyrB5,LysB28],des-(B29-B30)-Insulin
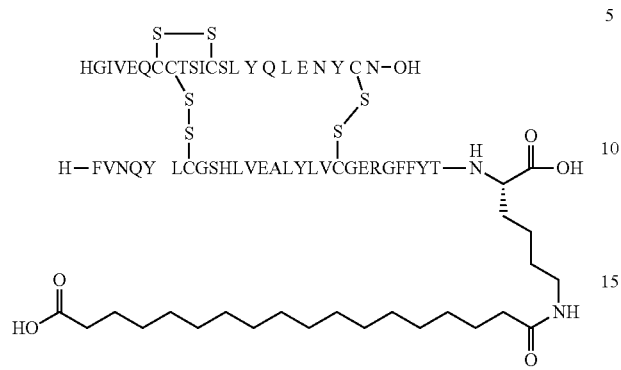
Synthesised by Synthesis Method 3.
Calc. Mass. = 5931.8; Found LC-MS m/4 = 1484
Example 4: N{Epsilon-B28}-[(4S)-4-carboxy-4-(17-carboxyheptadecanoylamino)butanoyl]-[TyrB5, LysB28],des-(B29-B30)-Insulin
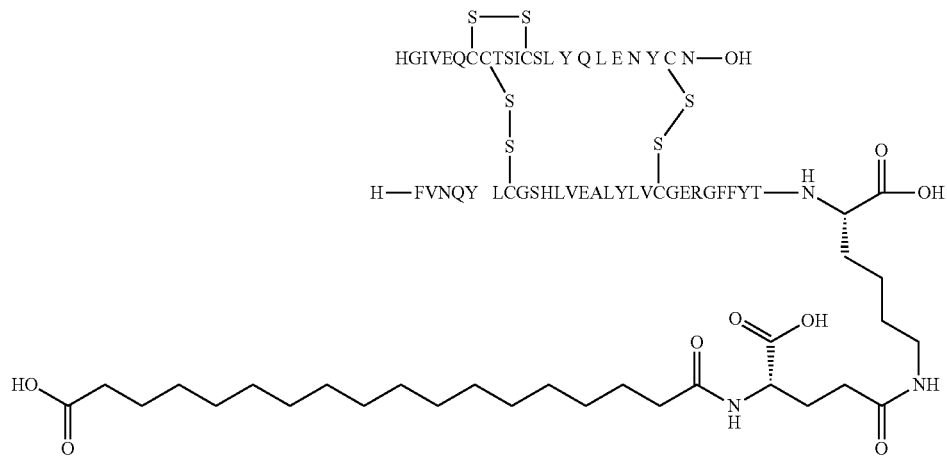
Synthesised by Synthesis Method 3
Calc. Mass. = 6060.9; Found LC-MS m/4 = 1516.73

Example 5: N{Epsilon-B28}-[2-[2-[2-(17-carboxy-heptadecanoylamino)ethoxy]ethoxy]acetyl]-[TyrB5, LysB28],des-(B29-B30)-Insulin
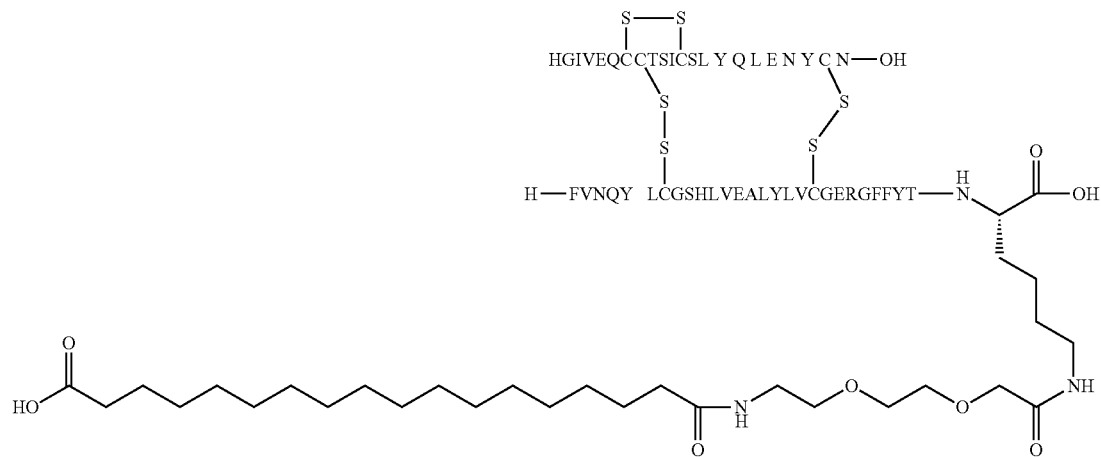
Synthesised by Synthesis Method 3
Calc. Mass. = 6077.0; Found LC-MS m/5 = 1216.34
Example 6: N{Epsilon-B28}-[(4S)-4-carboxy-4-[[(4S)-4-carboxy-4-(17-carboxyheptadecanoylamino)butanoyl]amino]butanoyl]-[TyrB5,LysB28], des-(B29-B30)-Insulin
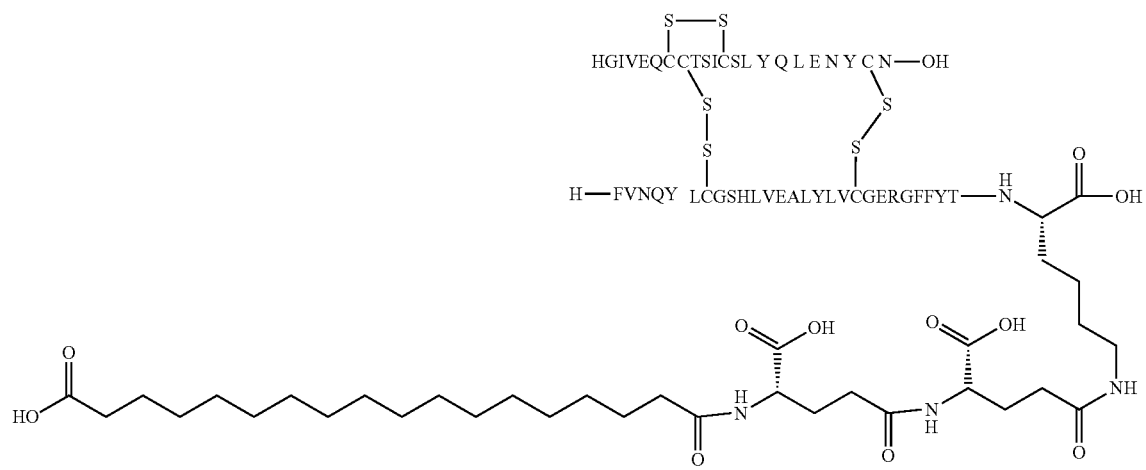
Synthesised by Synthesis Method 3
Calc. Mass. = 6190.0; Found LC-MS m/4 = 1548.37

Example 7: N{Epsilon-B28}-[2-[2-[2-[[(4S)-4-carboxy-4-(17-carboxyheptadecanoylamino)butanoyl]amino]ethoxy]ethoxy]acetyl]-[TyrB5,LysB28],des-(B29-B30)-Insulin

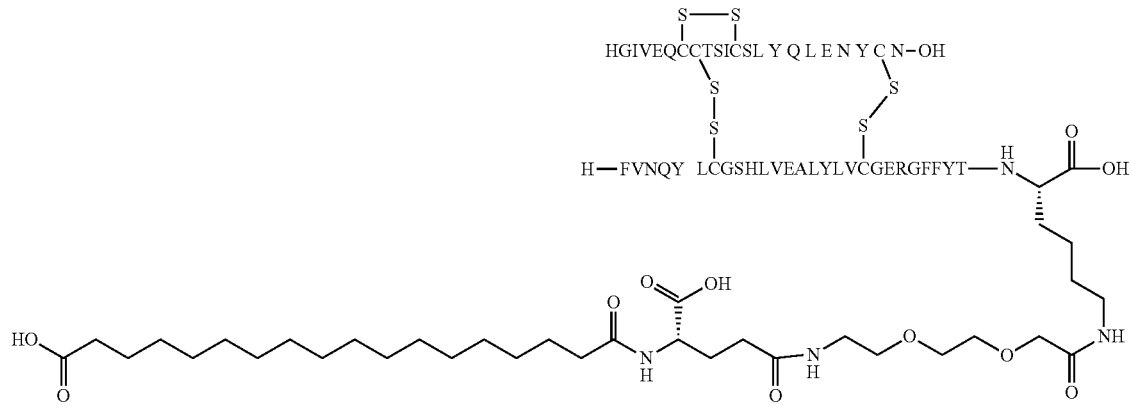

Synthesised by Synthesis Method 3
Calc. Mass. = 6206.1; Found LC-MS m/4 = 1552.37

Example 8: N{Epsilon-B28}-[(4S)-4-carboxy-4-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]butanoyl]-[TyrB5,LysB28],des-(B29-B30)-Insulin

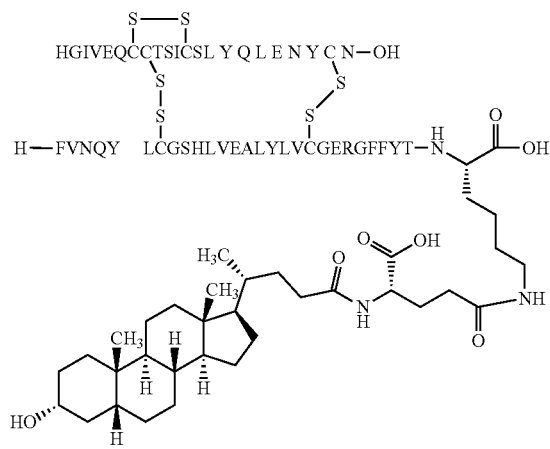

Synthesised by Synthesis Method 3
Calc. Mass. = 6123; Found LC-MS m/4 = 1531.7

Example 9: N{Epsilon-B28}-[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]-[TyrB5,LysB28],des-(B29-B30)-Insulin

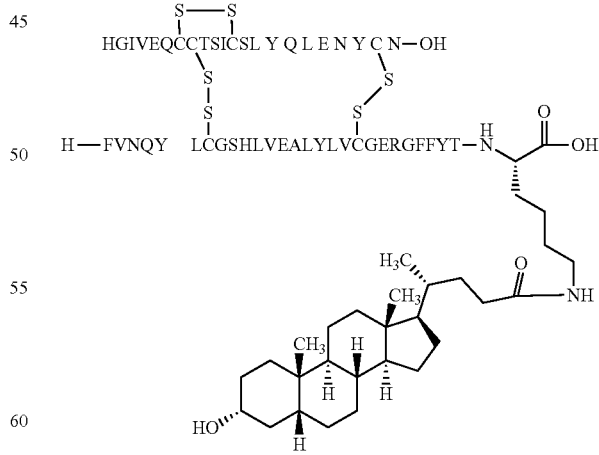

Synthesised by Synthesis Method 3
Calc. Mass. = 5993.9; Found LC-MS m/4 = 1499.16

Example 10: N{Epsilon-B28}-15-carboxypentadecanoyl-[TyrB5,GlyB26,LysB28],des-(B29-B30)-Insulin

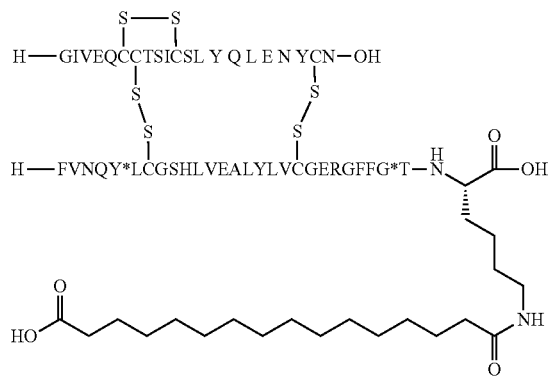

Synthesised by Synthesis Method 3
Calc. Mass. = 5797.7; Found LC-MS m/4 = 1449.93

Example 11: N{Epsilon-B28}-17-carboxyheptadecanoyl-[TyrB5,GlyB26,LysB28],des-(B29-B30)-Insulin

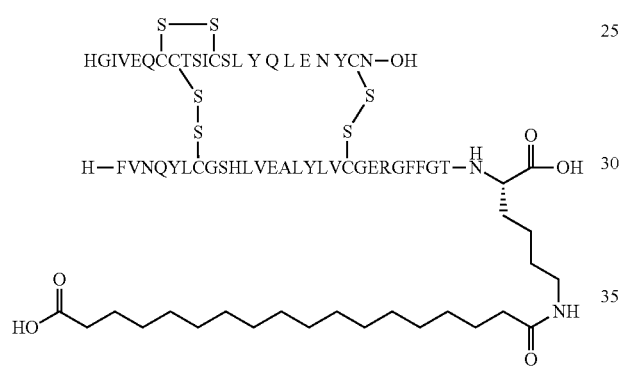

Synthesised by Synthesis Method 3
Calc. mass. = 5825.7; Found MALDI-MS = 5825.7

Example 12: N{Epsilon-B28}-17-carboxyheptadecanoyl-[GluA14,TyrB5,GlyB26,LysB28],des-(B29-B30)-Insulin

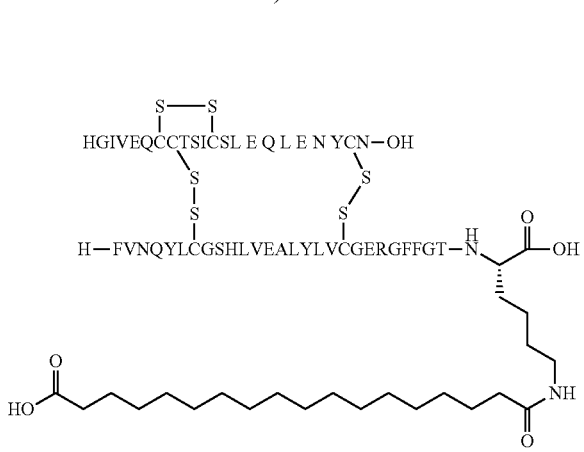

Synthesised by Synthesis Method 3
Calc. mass. = 5791.6; Found LC-MS m/3 = 1931.44

Example 13: N{Epsilon-B28}-[(4S)-4-carboxy-4-(17-carboxyheptadecanoylamino)butanoyl]-[GluA14,TyrB5,GlyB26,LysB28],des-(B29-B30)-Insulin

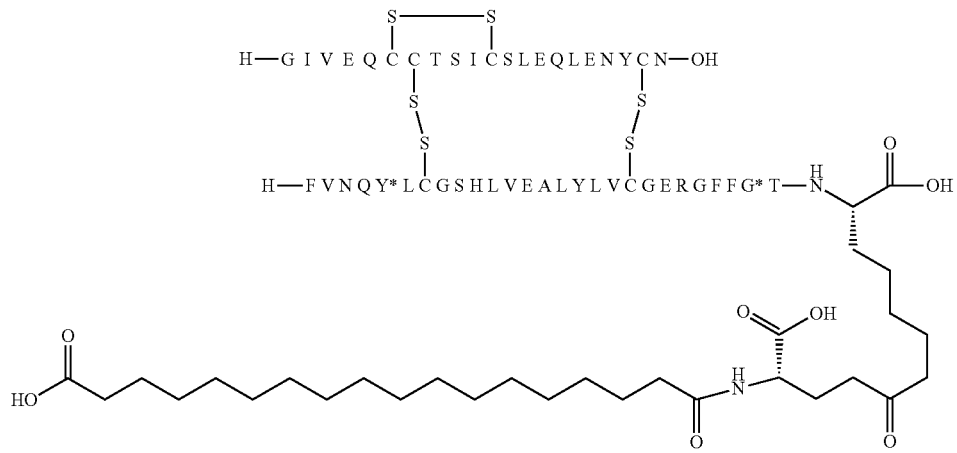

Synthesised by Synthesis Method 3
Calc. mass. = 5920.8; Found LC-MS m/5 = 1185.04

Example 14: N{Epsilon-B28}-[(4S)-4-carboxy-4-[[(4S)-4-carboxy-4-(17-carboxyheptadecanoylamino)butanoyl]amino]butanoyl]-[GluA14,TyrB5, GlyB26,LysB28],des-(B29-B30)-Insulin

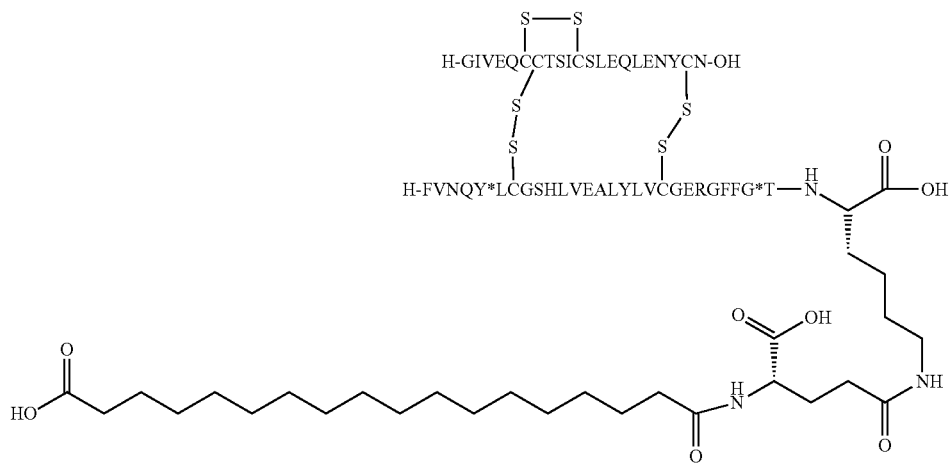

Synthesised by Synthesis Method 3

Calc.Mass. = 6049.9; Found LC-MS m/4 = 1513.32

Example 15: N{Epsilon-B28}-[2-[2-[2-[[(4S)-4-carboxy-4-(17-carboxyheptadecanoylamino)butanoyl]amino]ethoxy]ethoxy]acetyl]-[GluA14, TyrB5,GlyB26,LysB28],des-(B29-B30)-Insulin

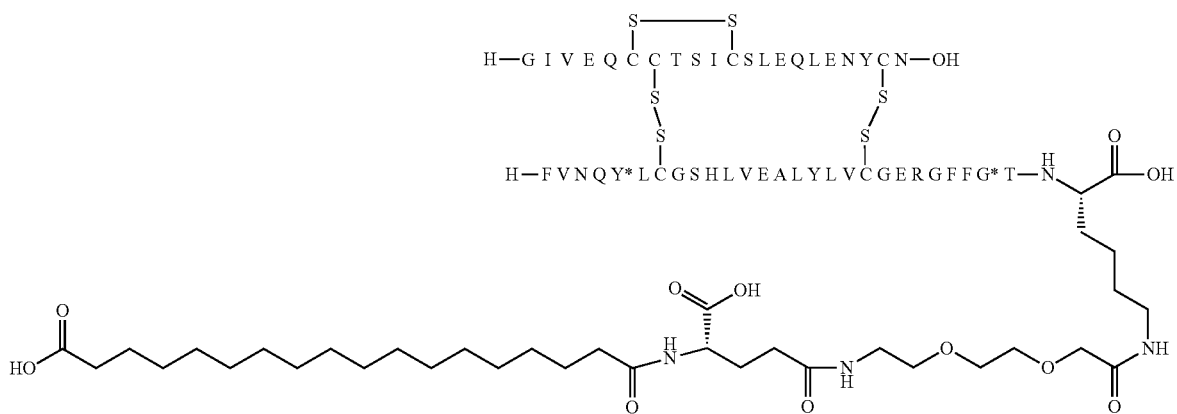

Synthesised by Synthesis Method 3
Calc. mass. = 6065.9; Found LC-MS m/4 = 1517.34

Example 16: N{Epsilon-B28}-[2-[2-[2-[[(4S)-4-carboxy-4-(19-carboxynonadecanoylamino)butanoyl]amino]ethoxy]ethoxy]acetyl]-[GluA14,TyrB5,GlyB26,LysB28],des-(B29-B30)-Insulin
Synthesised by Synthesis Method 3
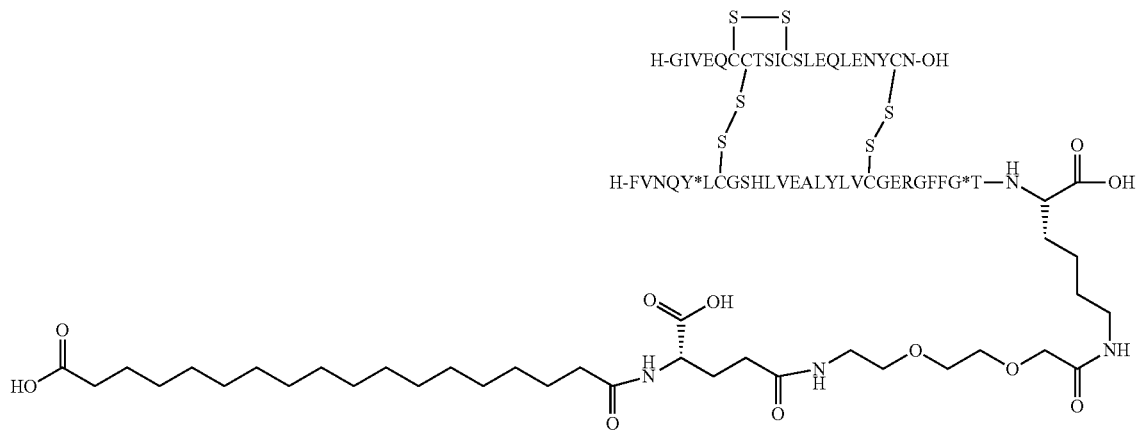
Calc.mass. = 6094.0; Found LC-MS m/4 = 1524.36
Example 17: N{Epsilon-B28}-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[GluA14,TyrB5,GlyB26,LysB28],des-(B29-B30)-Insulin

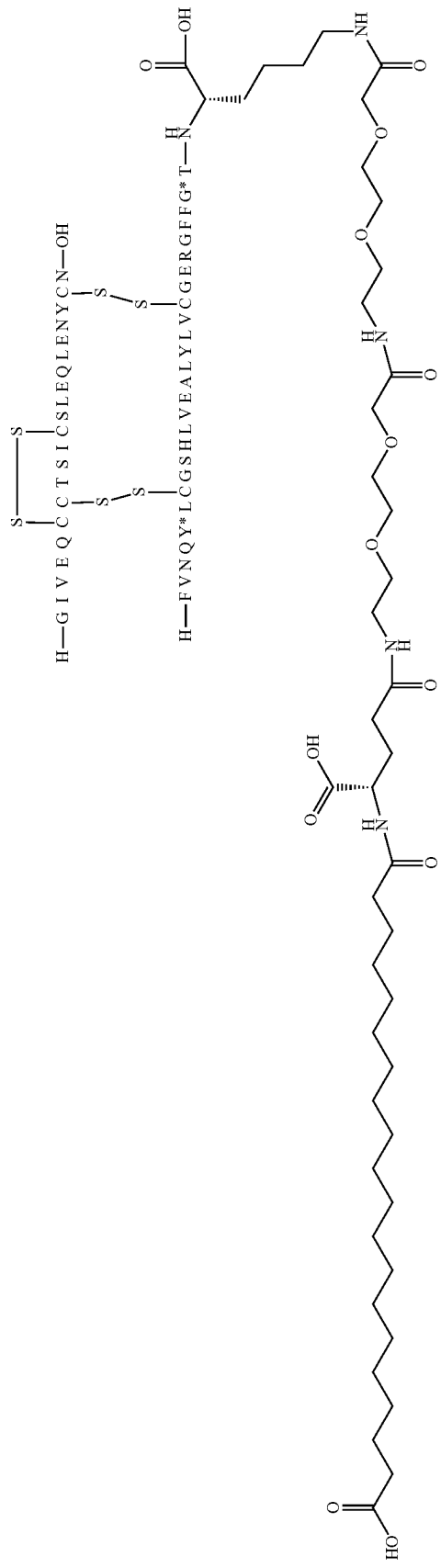

Example 18: N{Epsilon-B28}-[(4S)-4-carboxy-4-(19-carboxynonadecanoylamino)butanoyl]-[GluA14,TyrB5,GlyB26,LysB28],des-(B29-B30)-Insulin
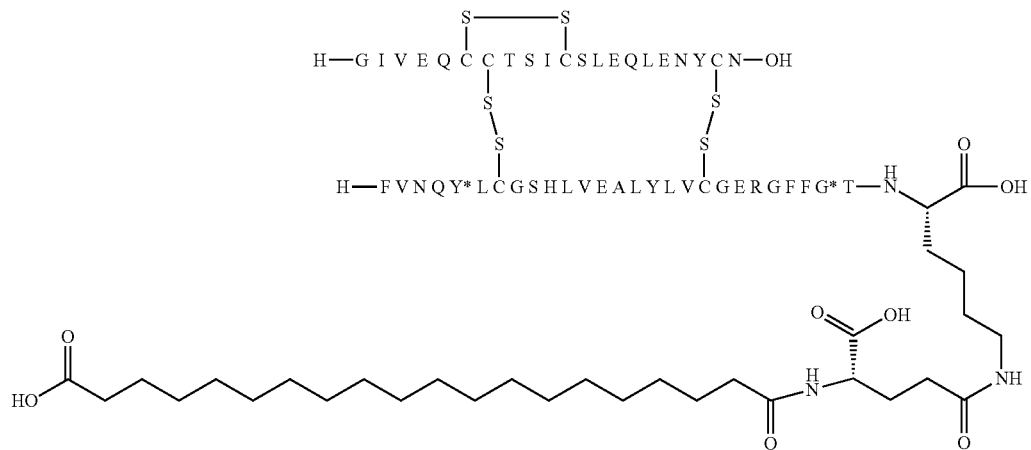
Synthesised by Synthesis Method 3
Calc. mass. = 5948.8; Found LC-MS m/5 = 1190.69
Example 19: N{Epsilon-B28}-19-carboxynonadecanoyl-[GluA14,TyrB5,GlyB26,LysB28],des-(B29-B30)-Insulin
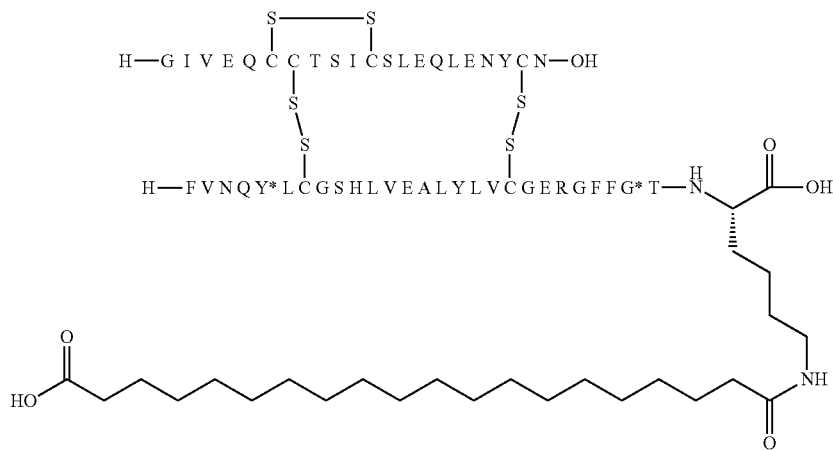
Synthesised by Synthesis Method 3
Calc. mass. = 5819.7; Found LC-MS m/4 = 1455.67

Example 20: N{Epsilon-B28}-15-(1H-tetrazol-5-yl)pentadecanoyl-[GluA14,TyrB5,GlyB26,LysB28], des-(B29-B30)-Insulin Example 22: N{Epsilon-B28}-16-(1H-tetrazol-5-yl)hexadecanoyl-[GluA14,TyrB5,GlyB26,LysB28],des-(B29-B30)-Insulin

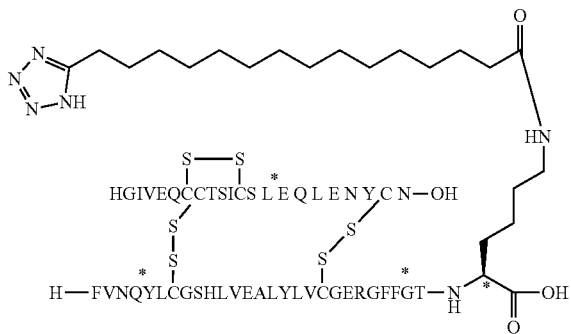

Synthesised by Synthesis Method 2
Calc. mass. = 5787.6; Found LC-MS m/4 = 1448.14

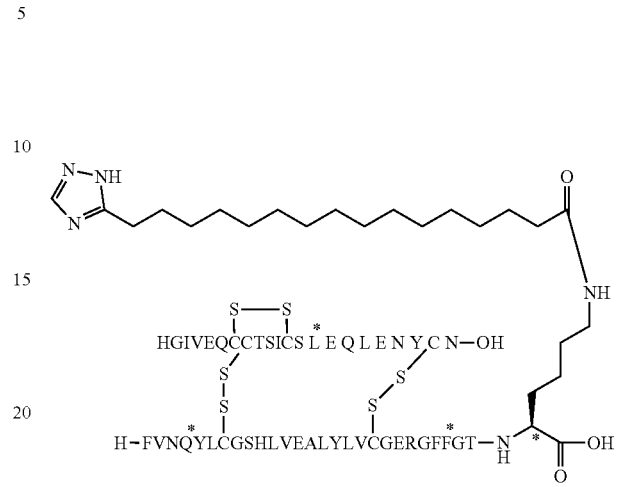

Synthesised by Synthesis Method 2
Calc. mass. = 5801.7; Found LC-MS m/4 = 1451.6

Example 21: N{Epsilon-B28}-17-(1H-tetrazol-5-yl)heptadecanoyl-[GluA14,TyrB5,GlyB26,LysB28], des-(B29-B30)-Insulin Synthesised by Synthesis Method 2

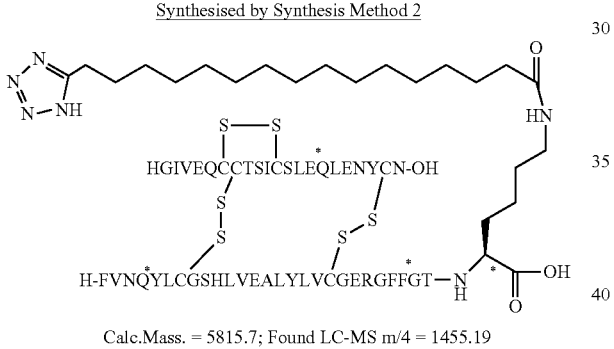

Calc.Mass. = 5815.7; Found LC-MS m/4 = 1455.19

Example 23: N{Epsilon-B28}-4-[16-(1H-tetrazol-5-yl)hexadecanoylsulfamoyl]butanoyl-[GluA14, TyrB5,GlyB26,LysB28],des-(B29-B30)-Insulin Synthesised by Synthesis Method 2

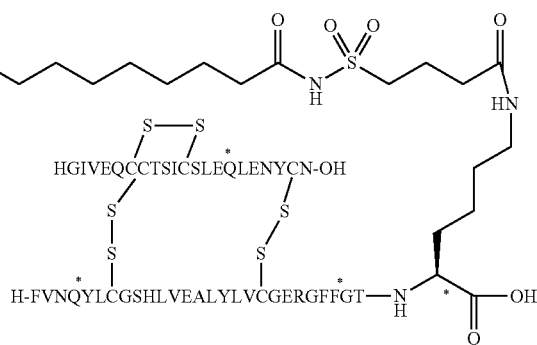

Calc.Mass. = 5950.8; Found LC-MS m/4 = 1488.81

Example 24: N{Epsilon-B28}-4-[4-[15-(1H-tetrazol-5-yl)pentadecanoylsulfamoyl]butanoylsulfamoyl]butanoyl-[GluA14,TyrB5,GlyB26,LysB28], des-(B29-B30)-Insulin
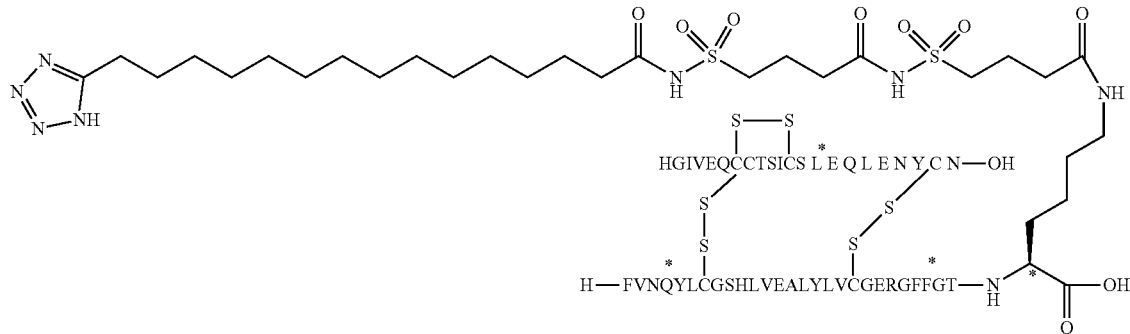
Synthesised by Synthesis Method 2
Calc. mass. = 6086.0; Found LC-MS m/4 = 1522.65
Example 25: N{Epsilon-B28}-4-[17-(1H-tetrazol-5-yl)heptadecanoylsulfamoyl]butanoyl-[GluA14,TyrB5,GlyB26,LysB28],des-(B29-B30)-Insulin
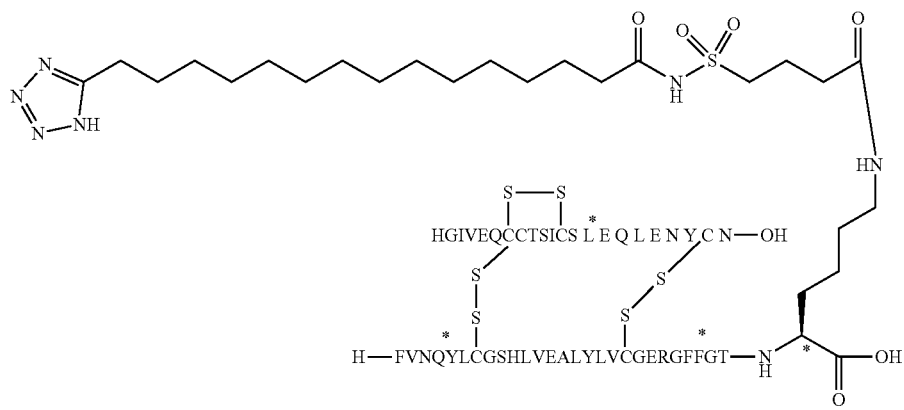
Synthesised by Synthesis Method 2
Calc. mass. = 5964.8; Found LC-MS m/4 = 1492.41

Example 26: N{Epsilon-B28}-[2-[2-[2-[[2-[2-[2-[[(4S)-4-carboxy-4-[15-(1H-tetrazol-5-yl)pentadecanoylamino]butanoyl]amino]ethoxy]ethoxy]acetyl]amino]ethoxy]ethoxy]acetyl]-[GluA14,TyrB5,GlyB26,LysB28],des-(B29-B30)-Insulin

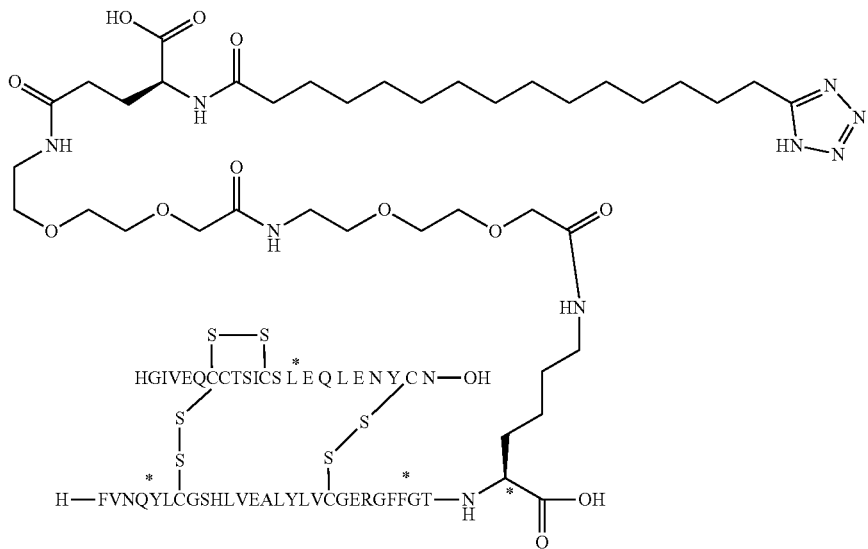

Synthesised by Synthesis Method 2
Calc. mass. = 6207.0; Found LC-MS m/4 = 1552.95

Example 27: N{Epsilon-B28}-4-[4-[17-(1H-tetrazol-5-yl)heptadecanoylsulfamoyl]butanoylsulfamoyl]butanoyl-[GluA14,TyrB5,GlyB26,LysB28],des-(B29-B30)-Insulin Synthesised by Synthesis Method 2

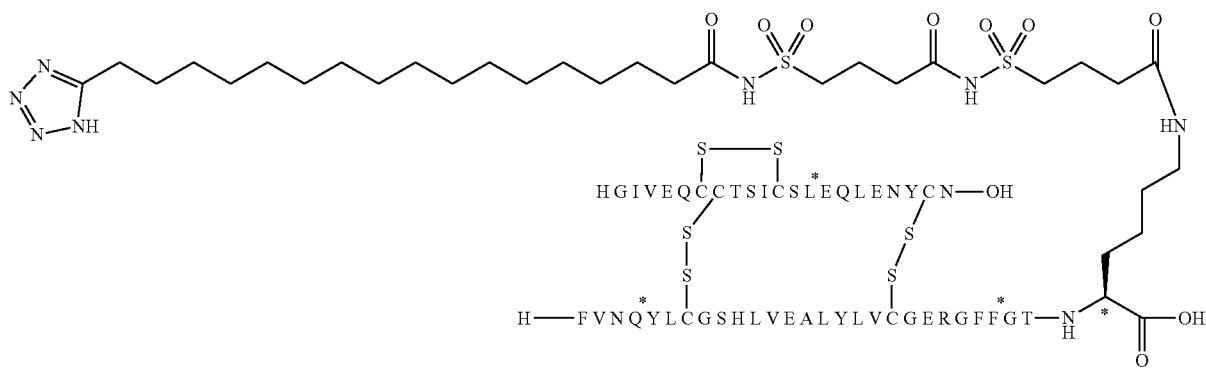

Calc. Mass. = 6114.0; Found LC-MS m/4 = 1529.62

Example 28: N{Epsilon-B28}-4-(17-carboxyhepta-decanoylsulfamoyl)butanoyl-[GluA14,TyrB5, GlyB26,LysB28],des-(B29-B30)-Insulin
Synthesised by Synthesis Method 2
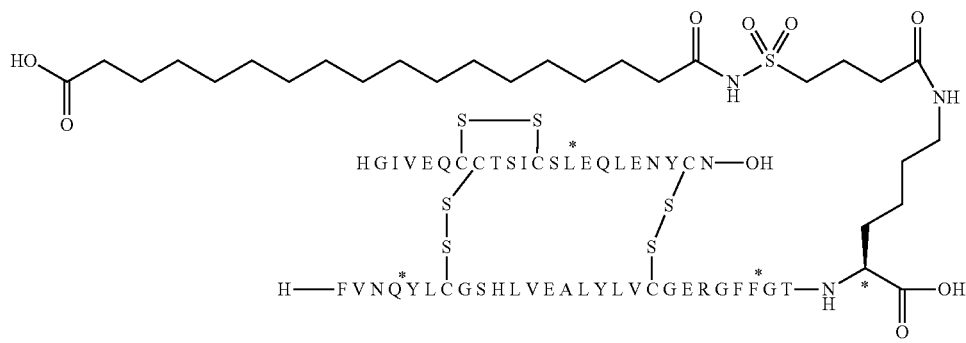
Calc. mass = 5940.8; Found LC-MS m/4 = 1486.34
Example 29: N{Epsilon-B28}-[2-[2-[2-[[(4S)-4-carboxy-4-[15-(1H-tetrazol-5-yl)pentadecanoylamino]butanoyl]amino]ethoxy]ethoxy]acetyl]-[GluA14,TyrB5,GlyB26,LysB28],des-(B29-B30)-Insulin
Synthesised by Synthesis Method 2
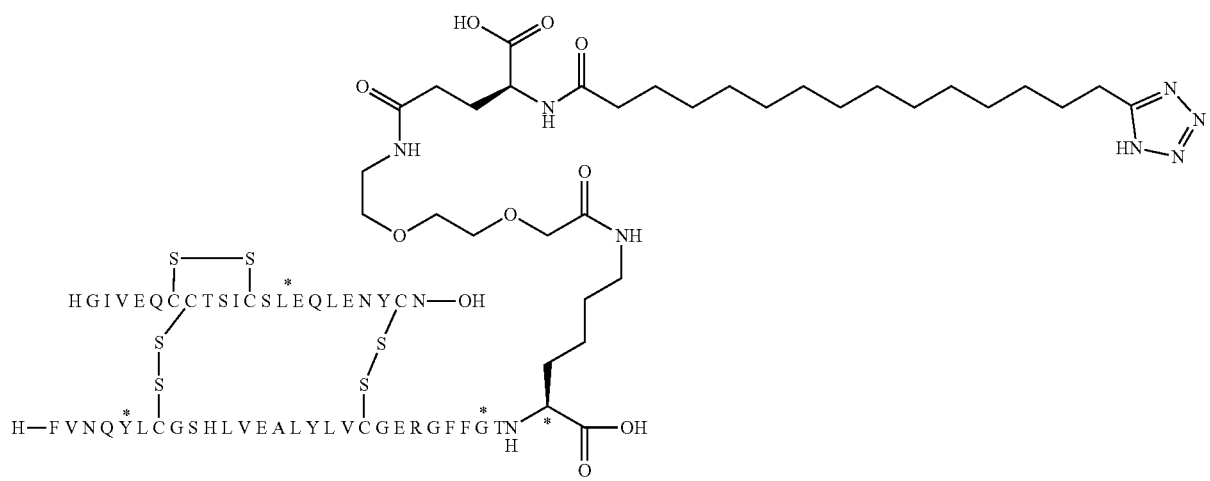
Calc. mass. = 6061.9; Found LC-MS m/4 = 1516.63

Example 30: N{Epsilon-B28}-[(4R)-4-carboxy-4-(17-carboxyheptadecanoylamino)butanoyl]-[GluA14,TyrB5,GlyB26,LysB28],des-(B29-B30)-Insulin
Synthesised by Synthesis Method 2
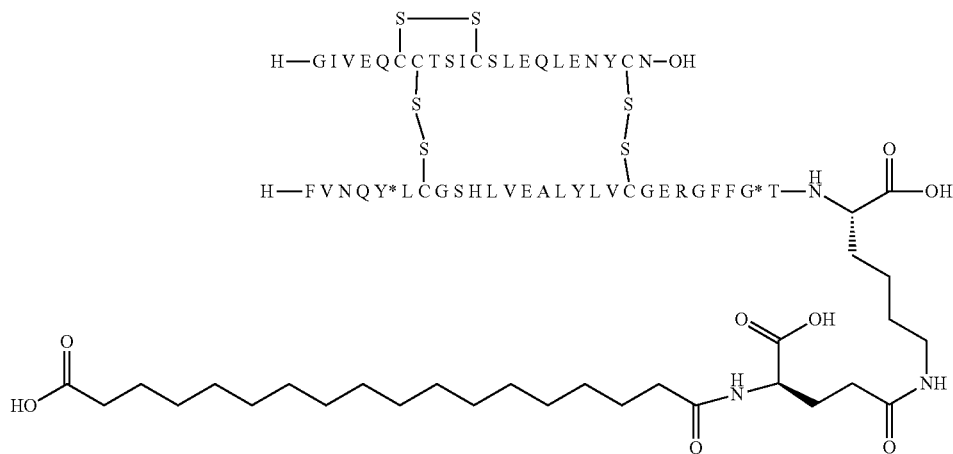
Calc. mass. = 5920.8; Found LC-MS m/4 = 1481.13
Example 31: N{Epsilon-B28}-[2-[2-[2-[[(4S)-4-carboxy-4-(17-carboxyheptadecanoylamino)butanoyl]amino]ethoxy]ethoxy]acetyl]-[TyrB5, GlyB26,LysB28],des-(B29-B30)-Insulin
Synthesised by Synthesis Method 2
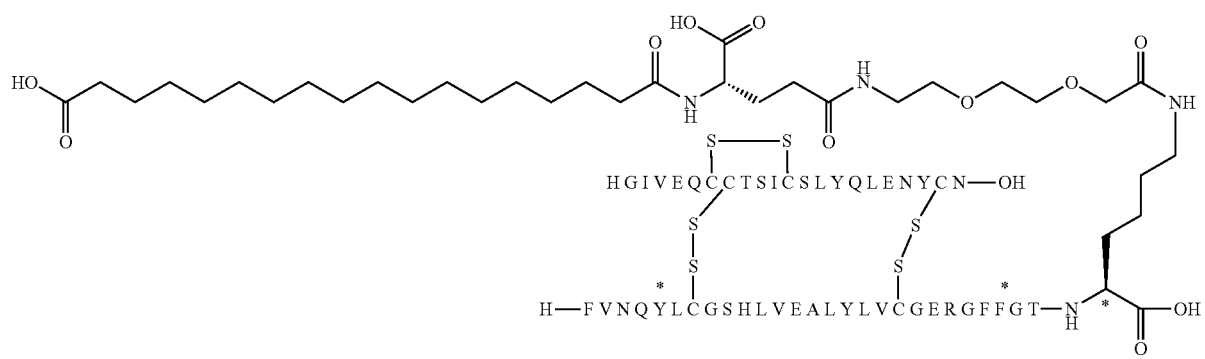
Calc. mass = 6100.0; Found LC-MS m/4 = 1525.8

Example 32: N{Epsilon-B28}-[2-[2-[2-[[(4S)-4-carboxy-4-(17-carboxyheptadecanoylamino)butanoyl]amino]ethoxy]ethoxy]acetyl]-[GluA14, TyrB5,AlaB26,LysB28],des-(B29-B30)-Insulin Synthesised by Synthesis Method 2

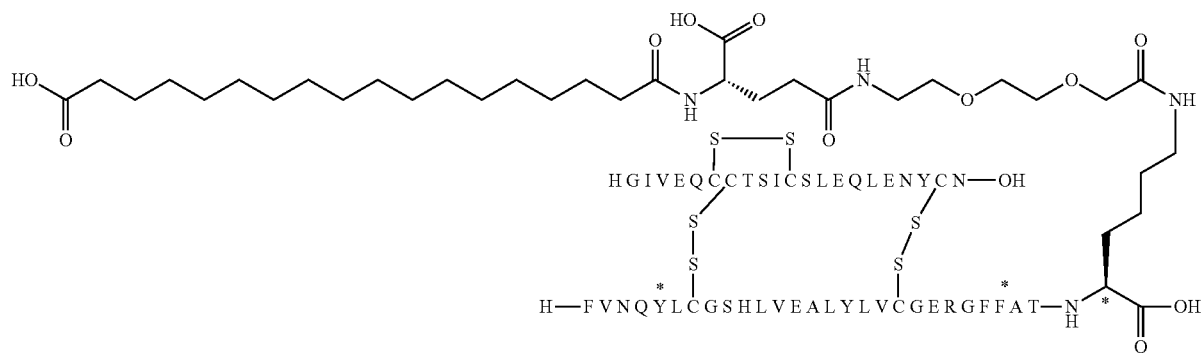

Calc. mass = 6079.9; Found LC-MS m/4 = 1520.77

Example 33: N{Epsilon-B28}-[2-[2-[2-[[(4S)-4-carboxy-4-(17-carboxyheptadecanoylamino)butanoyl]amino]ethoxy]ethoxy]acetyl]-[TyrB5,AlaB26,LysB28],des-(B29-B30)-Insulin Synthesised by Synthesis Method 2

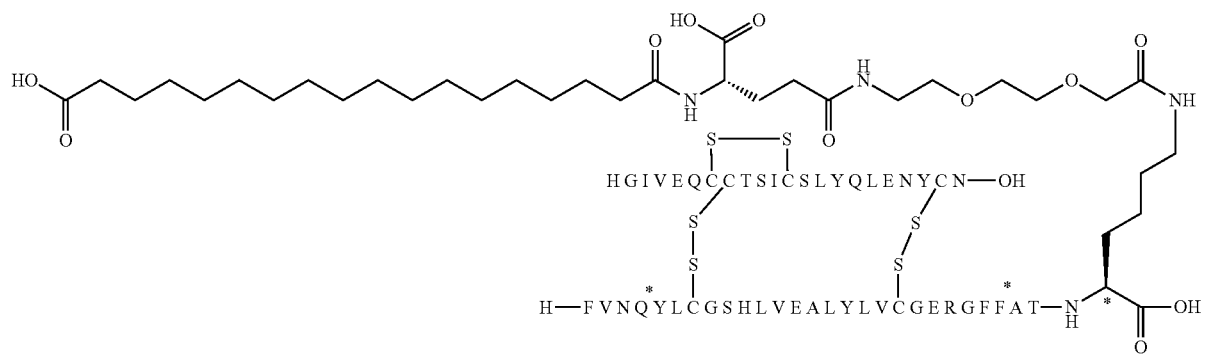

Calc. mass = 6114.0; Found LC-MS m/4 = 1529.2

Example 34: N{Epsilon-B28}-[(4S)-4-carboxy-4-(17-carboxyheptadecanoylamino)butanoyl]-[GluA14,TyrB5,AlaB26,LysB28],des-(B29-B30)-Insulin
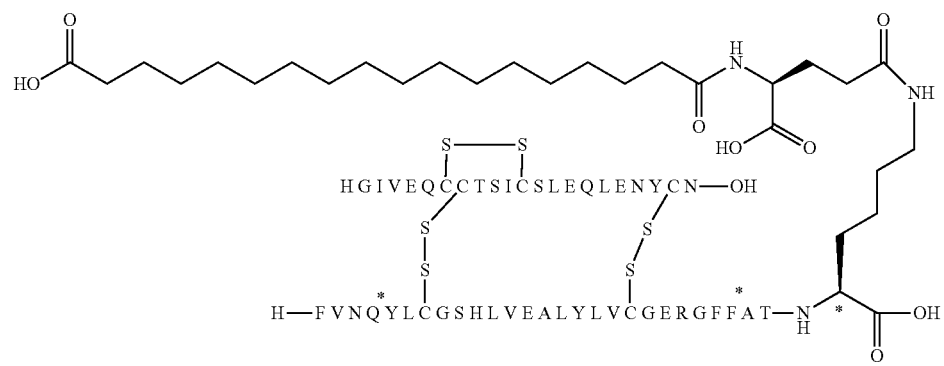
Calc. mass = 5934.8; Found LC-MS m/4 = 1484.5
Example 35: N{Epsilon-B28}-17-carboxyheptadecanoyl-[PheB5,LysB28],des-(B29-B30)-Insulin
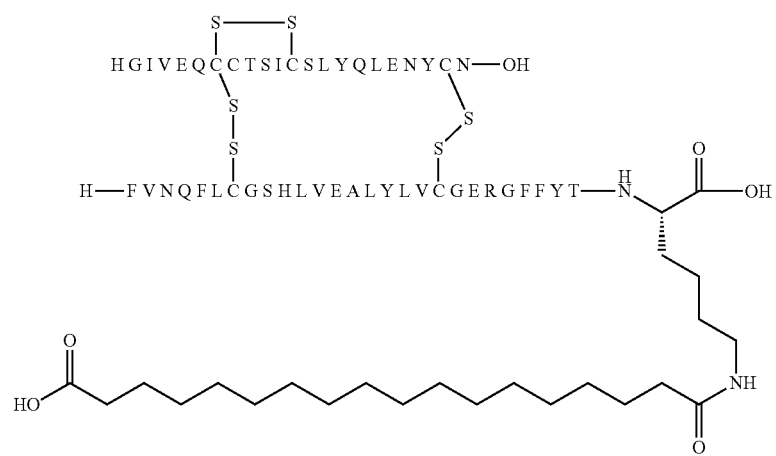
Calc. Mass = 5915.8; Found MALDI-MS = 5916

Example 36: N{Epsilon-B28}-17-carboxyheptadecanoyl-[GluA14,PheB5,GlyB26,LysB28],des-(B29-B30)-Insulin
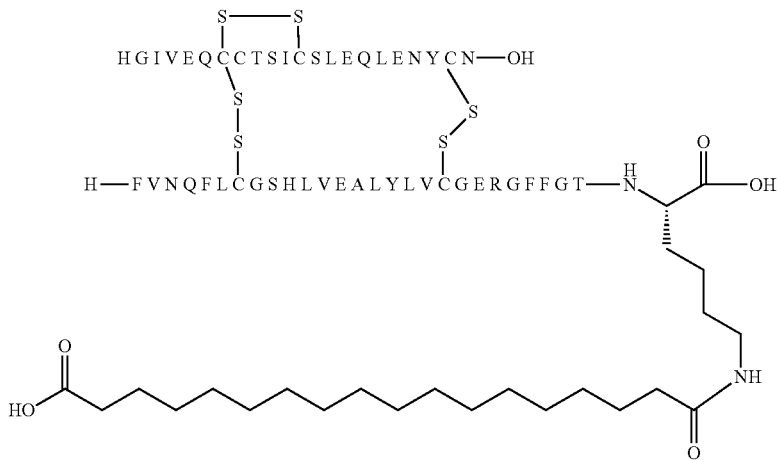
Calc. Mass = 5775.6; Found LC-MS m/4 = 1444.8
Example 37: N{Epsilon-B26}-17-carboxyheptadecanoyl-[TyrB5,LysB26],des-(B27-B30)-Insulin
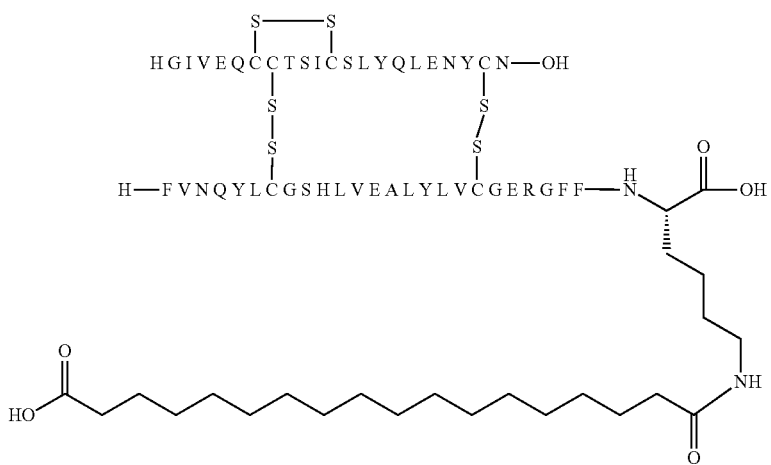
Calc. mass = 5667.6; Found LC-MS m/3 = 1889.9

Example 38: N{Epsilon-B26}-[(4S)-4-carboxy-4-(17-carboxyheptadecanoylamino)butanoyl]-[TyrB5,LysB26],des-(B27-B30)-Insulin
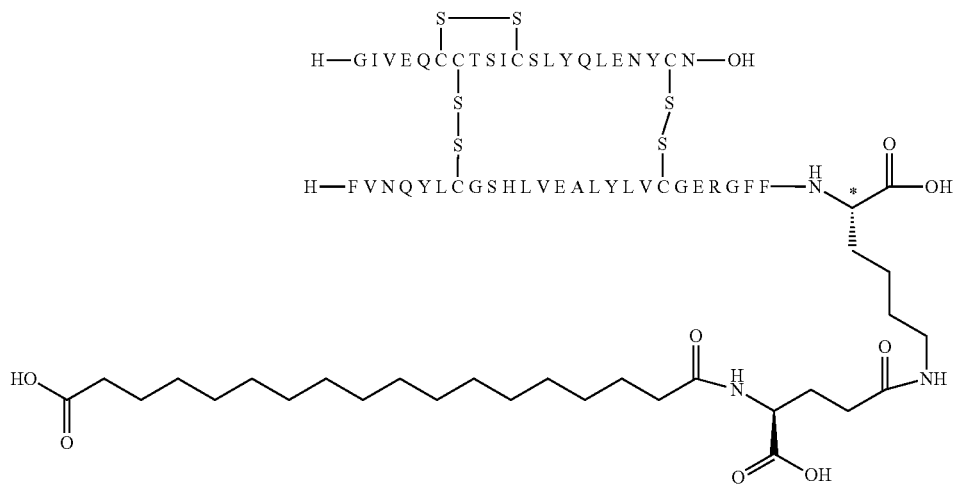
Calc. mass = 5796.7; Found LC-MS m/3 = 1933.1
Example 39: N{Epsilon-B26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[TyrB5,LysB26],des-(B27-B30)-Insulin
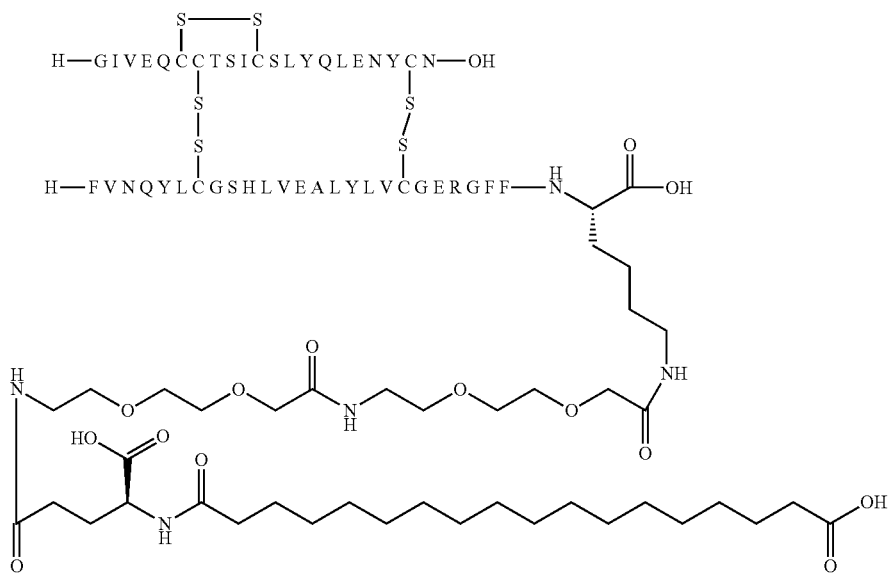
Calc. mass = 6087.0; Found LC-MS m/4 = 1522.5

Example 40: N{Epsilon-B29}-[(4S)-4-carboxy-4-(15-carboxypentadecanoylamino)butanoyl]-[TyrB5], des-ThrB30-Insulin
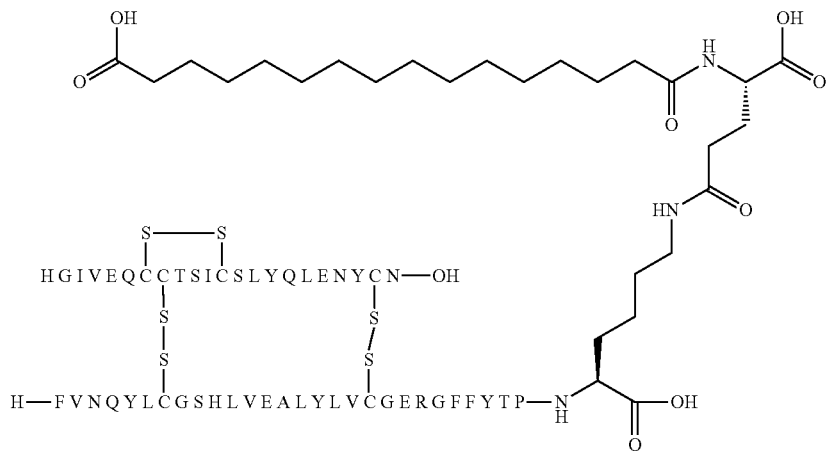
Calc. mass = 6130.0; Found LC-MS m/3 = 2044.3
Example 41: N{Epsilon-B29}-tetradecanoyl-[TyrB5],des-ThrB30-Insulin
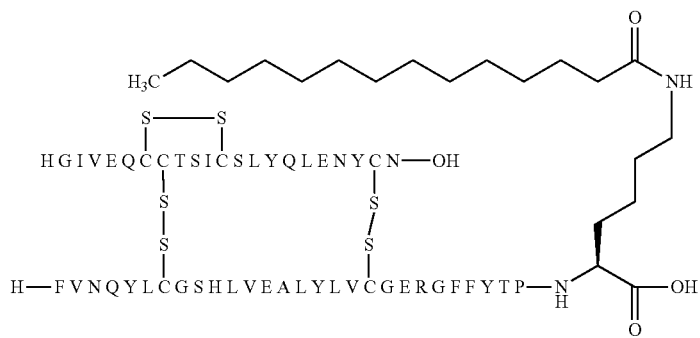
Calc. mass = 5942.9; Found LC-MS m/3 = 1982

Example 42: N{Epsilon-B29}-[(4S)-4-carboxy-4-(15-carboxypentadecanoylamino)butanoyl]-[TyrB5, GlyB26],des-ThrB30-Insulin
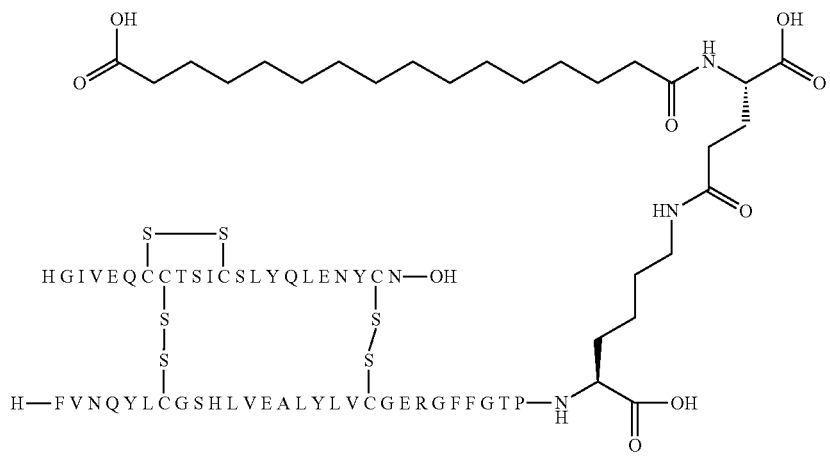
Calc. mass = 6023.9; Found MALDI-MS = 6026
Example 43: N{Epsilon-B29}-[(4S)-4-carboxy-4-(15-carboxypentadecanoylamino)butanoyl]-[TyrB5, AlaB26],des-ThrB30-Insulin
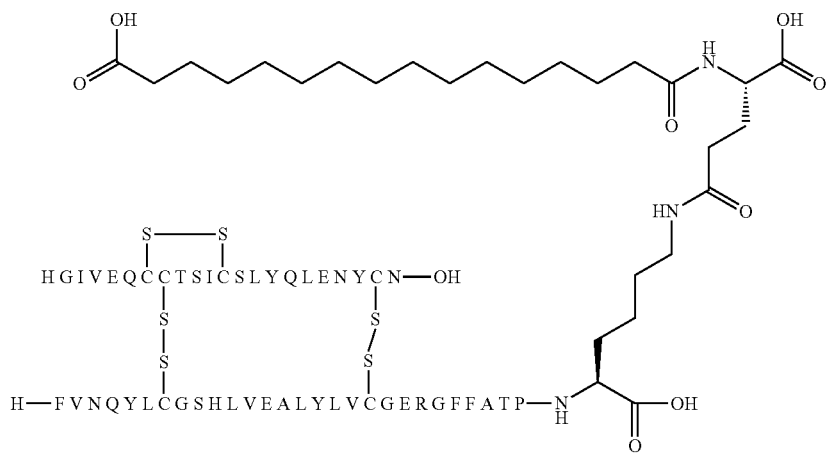
Calc. mass = 6037.9; Found LC-MS m/4 = 1510.5

Example 44: N{Epsilon-B29}-[(4S)-4-carboxy-4-(17-carboxyheptadecanoylamino)butanoyl]-[TyrB5, GlyB26],des-ThrB30-Insulin
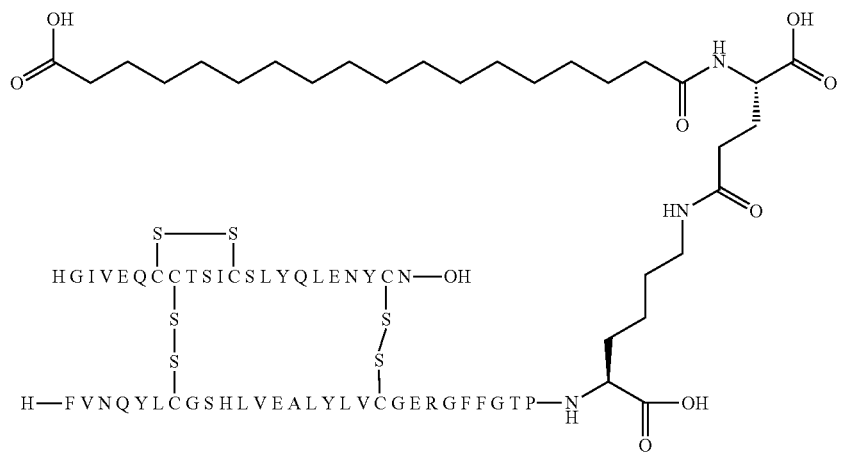
Calc. mass = 6051.9; Found MALDI-MS = 6052
Example 45: N{Epsilon-B29}-[(4S)-4-carboxy-4-(17-carboxyheptadecanoylamino)butanoyl]-[TyrB5, AlaB26],des-ThrB30-Insulin
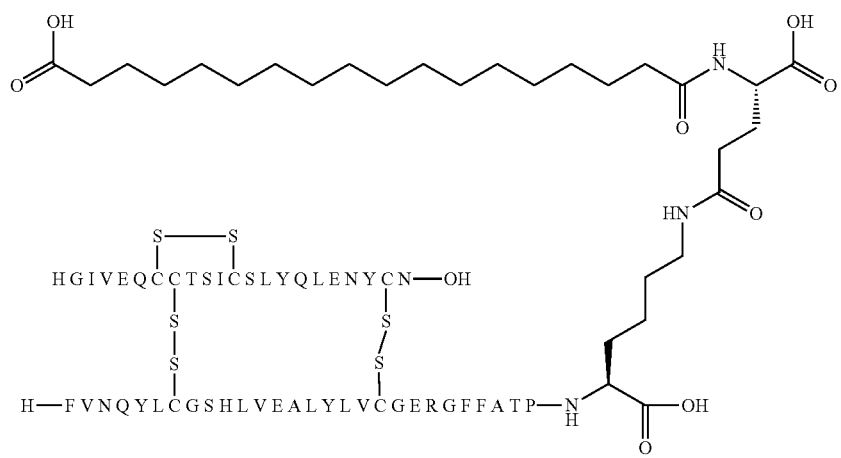
Calc. mass = 6066.0; Found MALDI-MS = 6065

Example 46: N{Epsilon-B26}-[2-[2-[2-[[(4S)-4-carboxy-4-(17-carboxyheptadecanoylamino)butanoyl]amino]ethoxy]ethoxy]acetyl]-[TyrB5,LysB26],des-(B27-B30)-Insulin

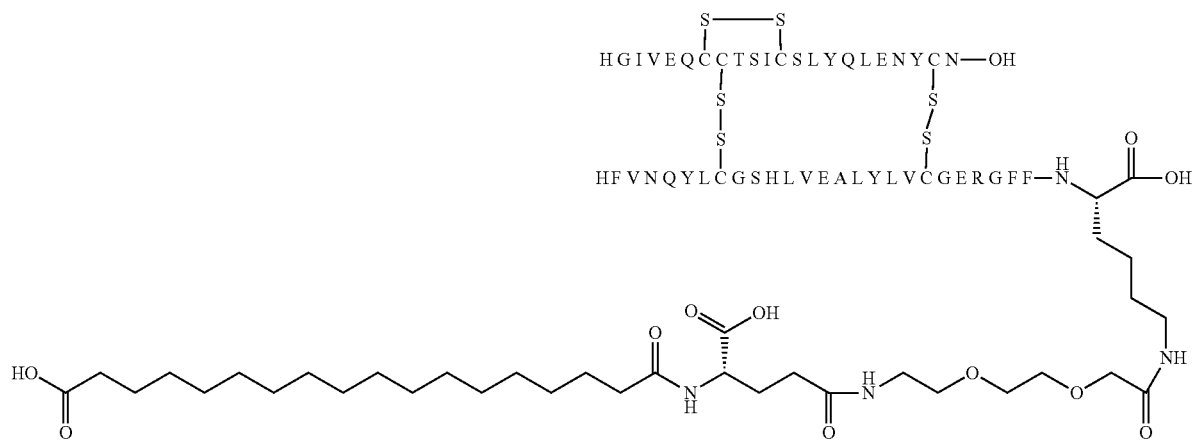

Calc. Mass = 5941.8; Found LC-MS m/4 = 1486

Comparators
Comparator 1: [TyrB5,LysB28],des-(B29-B30)-Insulin

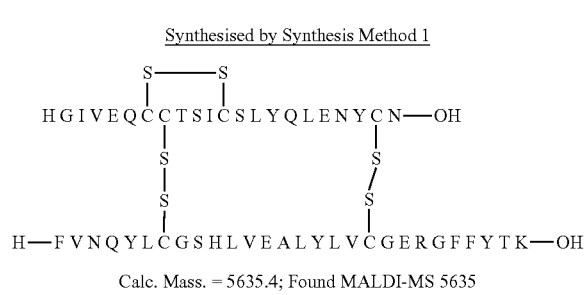

Calc. Mass. = 5635.4; Found MALDI-MS 5635

Comparator 2: [TyrB5,GlyB26],des-ThrB30-Insulin

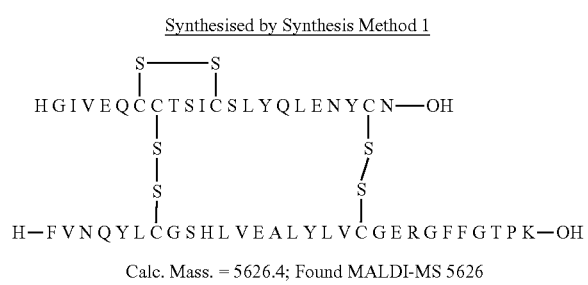

Calc. Mass. = 5626.4; Found MALDI-MS 5626

Comparator 3: [TyrB5,AlaB26],des-ThrB30-Insulin

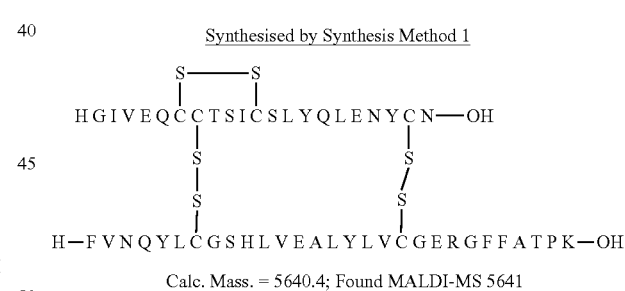

Calc. Mass. = 5640.4; Found MALDI-MS 5641

Comparator 4: [GluA14,TyrB5,GlyB26,LysB28],des-(B29-B30)-Insulin

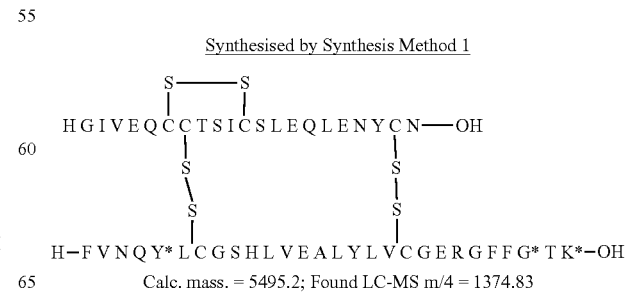

Calc. mass. = 5495.2; Found LC-MS m/4 = 1374.83

Comparator 5: N{Epsilon-B29}-[(4S)-4-carboxy-4-(15-carboxypentadecanoylamino)butanoyl]-Insulin
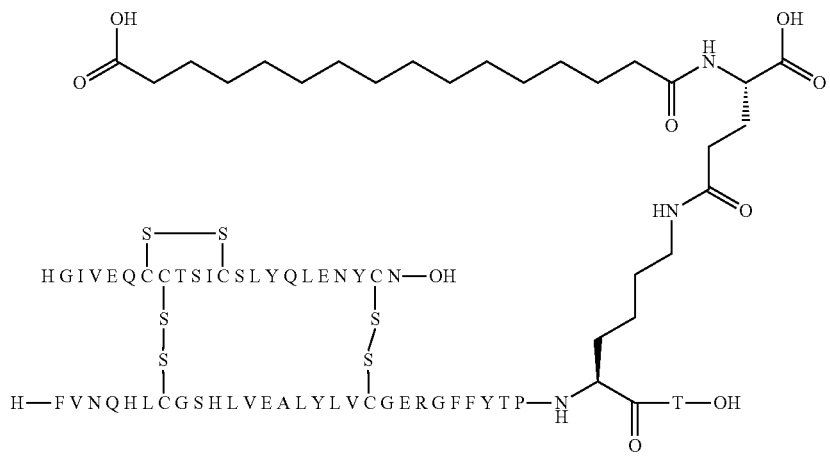
Comparator 6: N{Epsilon-B28}-17-carboxyheptadecanoyl-[LeuB5,LysB28],des-(B29-B30)-Insulin
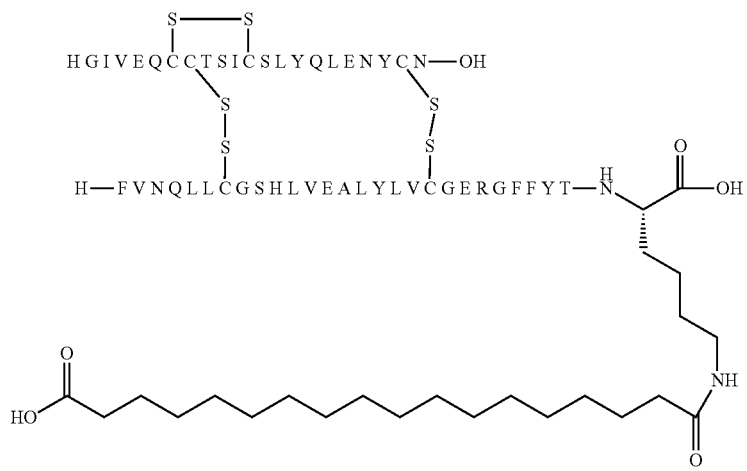
Calc. Mass = 5881.8; Found MALDI-MS = 5882

Comparator 7: N{Epsilon-B28}-17-carboxyheptadecanoyl-[SerB5,LysB28],des-(B29-B30)-Insulin
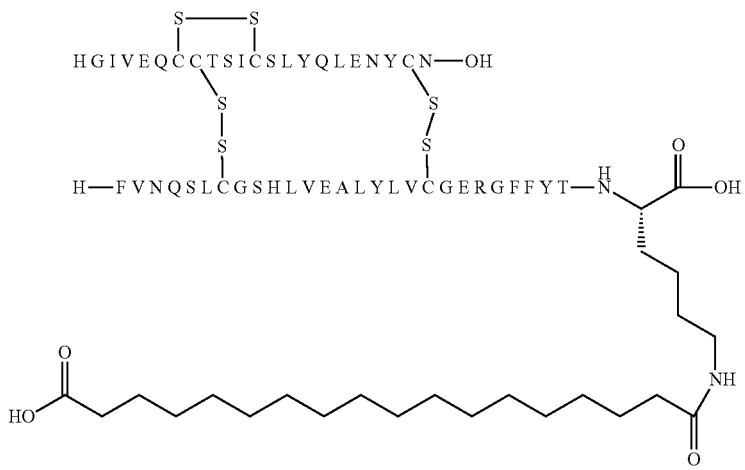
Calc. Mass = 5875.7; Found MALDI-MS = 5876
Comparator 8: N{Epsilon-B28}-17-carboxyheptadecanoyl-[AlaB5,LysB28],des-(B29-B30)-Insulin
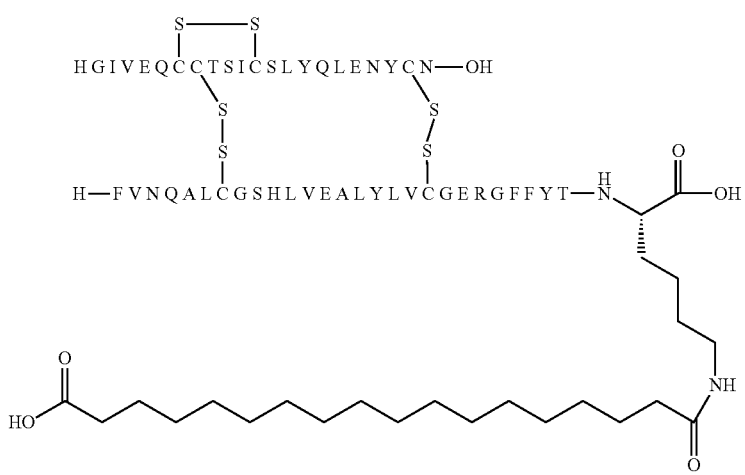
Calc. Mass = 5839.7; Found MALDI-MS = 5840

Comparator 9: N{Epsilon-B28}-17-carboxyheptadecanoyl-[GlyB26,LysB28],des-(B29-B30)-Insulin

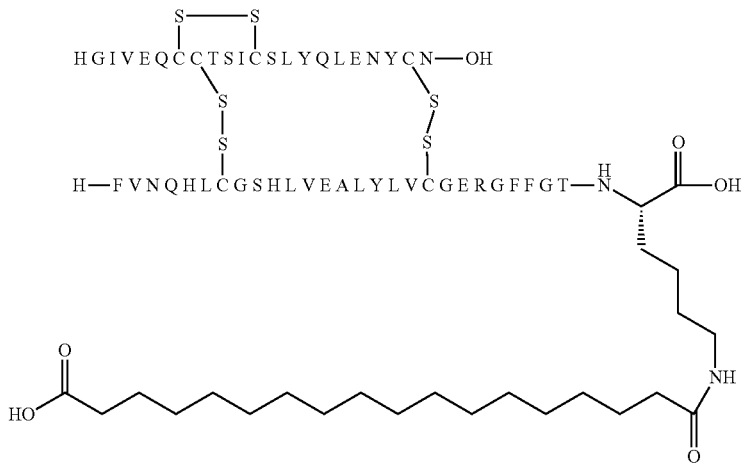

Calc. Mass = 5799.7; Found MALDI-MS = 5800

The invention claimed is:

1. An insulin derivative, comprising an insulin analogue comprising B5Y or B5F and a substituent comprising an acyl group, or a pharmaceutically acceptable salt, amide or ester thereof, wherein said insulin analogue further comprises B28K or B26K and said acyl group is attached to B28K or B26K.

2. The insulin derivative according to claim 1, wherein said substituent has the following formula (I):

Acy-L1-L2-L3 wherein:
   Acy is an acyl group and is represented by lithocholic acid or comprises at least one functional group of formulae:

—CO—(CH$_2$)$_x$—COOH; or      Chem. 1:

—CO—(CH$_2$)$_x$-tetrazolyl;      Chem. 2:

wherein x represents an integer in the range of from 12 to 20; and the tetrazolyl group is 1H-tetrazol-5-yl, or is a fatty acid of formula:

—CO—(CH$_2$)$_x$—CH$_3$,      Chem. 3:

wherein x represents an integer in the range from 8 to 16,
   L1 is absent and represents a covalent bond or represents OEG, gGlu, DgGlu or sulfonimide C-4,
   L2 is absent and represents a covalent bond or represents OEG, gGlu, DgGlu or sulfonimide C-4,
   L3 is absent and represents a covalent bond or represents OEG, gGlu, DgGlu or sulfonimide C-4,
   wherein gGlu represents a gamma glutamic acid residue and OEG represents [2-(2-aminoethoxy)ethoxy]acetyl.

3. The insulin derivative according to claim 2, wherein said insulin analogue comprises
   i. A14E, B5Y, B26A, B28K, desB29-30;
   ii. A14E, B5Y, B26G, B28K, desB29-30;
   iii. B5Y, B26A, B28K, desB29-30;
   iv. B5Y, B26G, B28K, desB29-30;
   v. B5Y, B28K, desB29-30;
   vi. A14E, B5F, B26G, B28K, desB29-30;
   vii. B5F, B28K, desB29-30;
   viii. B5Y, B26K, desB27-desB30;
   xii. B5F, B26A, B28K, desB29-30;
   xiii. B5Y, B26A, B28K, desB29-30;
   xiv. B5Y, B26G, B28K, desB29-30;
   xv. B5F, B26G, B28K, desB29-30;
   xvi. A14E, B5F, B26A, B28K, desB29-30;
   xvii. A14E, B5Y, B26A, B28K, desB29-30;
   xviii. A14E, B5Y, B26G, B28K, desB29-30;

xix. A14E, B5Y, B28K, desB29-30;
xx. A14E, B5F, B28K, desB29-30; or
xxi. A14E, B5Y, B26K, desB27-desB30.

4. The insulin derivative according to claim 3, wherein -L1-L2-L3 represents a divalent linking group selected from group consisting of: DgGlu, gGlu, gGlu-gGlu, gGlu-OEG, gGlu-OEG-OEG, OEG, sulfonimide-C4, and sulfonimide-C4-sulfonimide-C4.

5. A method of treating diabetes, cardiovascular disease, atherosclerosis, or endothelial dysfunction, or reducing liver triglyceride content or reducing body weight gain, comprising administering to a subject in need thereof a therapeutically effective amount of an insulin derivative according to claim 3.

6. A method for treating diabetes, diabetes of Type 1, diabetes of Type 2, impaired glucose tolerance, hyperglycemia, dyslipidemia, obesity, metabolic syndrome X, insulin resistance syndrome, hypertension, cognitive disorders, atherosclerosis, myocardial infarction, stroke, cardiovascular disorders, coronary heart disease, stroke, inflammatory bowel syndrome, dyspepsia, hypotension or gastric ulcers, comprising administrating to a subject in need thereof a therapeutically effective amount of an insulin derivative according to claim 3.

7. An insulin derivative according to claim 2, wherein said insulin analogue comprising an amino acid sequence of SEQ ID NO: 3 and an amino acid sequence of SEQ ID NO: 5.

8. The insulin derivative according to claim 1, wherein said insulin analogue further comprises A14E and/or desB30 and/or desB29-30 and/or desB27-30.

9. The insulin derivative according to claim 1, wherein said insulin analogue comprises
i. A14E, B5Y, B26A, B28K, desB29-30;
ii. A14E, B5Y, B26G, B28K, desB29-30;
iii. B5Y, B26A, B28K, desB29-30;
iv. B5Y, B26G, B28K, desB29-30;
v. B5Y, B28K, desB29-30;
vi. A14E, B5F, B26G, B28K, desB29-30;
vii. B5F, B28K, desB29-30;

viii. B5Y, B26K, desB27-desB30;
xii. B5F, B26A, B28K, desB29-30;
xiii. B5Y, B26A, B28K, desB29-30;
xiv. B5Y, B26G, B28K, desB29-30;
xv. B5F, B26G, B28K, desB29-30;
xvi. A14E, B5F, B26A, B28K, desB29-30;
xvii. A14E, B5Y, B26A, B28K, desB29-30;
xviii. A14E, B5Y, B26G, B28K, desB29-30;
xix. A14E, B5Y, B28K, desB29-30;
xx. A14E, B5F, B28K, desB29-30; or
xxi. A14E, B5Y, B26K, desB27-desB30.

10. The insulin derivative according to claim 9, wherein Acy is selected from the group consisting of: lithocholic acid, 1,16-hexadecanedioic acid, 1,18-octadecanedioic acid, 1,20-eicosanedioic acid, tetrazole-C16, tetrazole-C17, tetrazole C18 and tetradecanoic acid.

11. An insulin derivative according to claim 1, wherein said insulin analogue comprising an amino acid sequence of SEQ ID NO: 3 and an amino acid sequence of SEQ ID NO: 5.

12. A method of treating diabetes, cardiovascular disease, atherosclerosis, or endothelial dysfunction, or reducing liver triglyceride content or reducing body weight gain, comprising administering to a subject in need thereof a therapeutically effective amount of an insulin derivative according to claim 1.

13. A method for treating diabetes, diabetes of Type 1, diabetes of Type 2, impaired glucose tolerance, hyperglycemia, dyslipidemia, obesity, metabolic syndrome X, insulin resistance syndrome, hypertension, cognitive disorders, atherosclerosis, myocardial infarction, stroke, cardiovascular disorders, coronary heart disease, stroke, inflammatory bowel syndrome, dyspepsia, hypotension or gastric ulcers, comprising administrating to a subject in need thereof a therapeutically effective amount of an insulin derivative according to claim 1.

14. An insulin derivative, comprising an insulin analogue comprising B5Y or B5F, and B26G or B26A, and a substituent comprising an acyl group, or a pharmaceutically acceptable salt, amide or ester thereof, wherein said insulin analogue further comprises B28K and said acyl group is attached to B28K.

15. An insulin derivative of N{Epsilon-B28}-[2-[2-[2-[[(4S)-4-carboxy-4-(17-carboxyheptadecanoylamino)butanoyl]amino]ethoxy]ethoxy]acetyl]-[GluA14,TyrB5,GlyB26,LysB28],des-(B29-B30)-Insulin

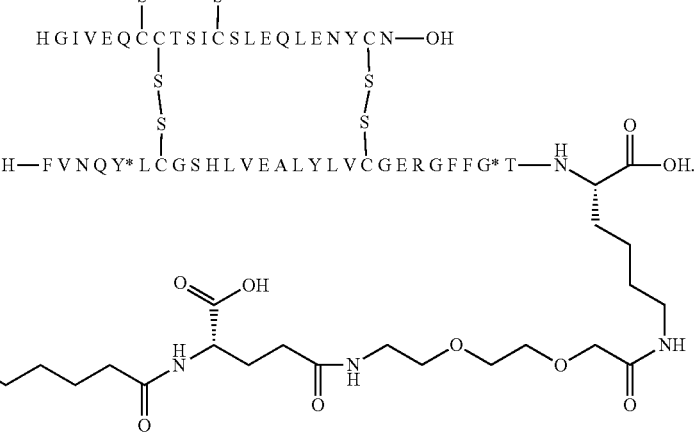

16. A method for treating diabetes, diabetes of Type 1, diabetes of Type 2, impaired glucose tolerance, hyperglycemia, dyslipidemia, obesity, metabolic syndrome X, insulin resistance syndrome, hypertension, cognitive disorders, atherosclerosis, myocardial infarction, stroke, cardiovascular disorders, coronary heart disease, stroke, inflammatory bowel syndrome, dyspepsia, hypotension or gastric ulcers, comprising administrating to a subject in need thereof a therapeutically effective amount of the insulin derivative according to claim 15.

17. A method of treating diabetes, cardiovascular disease, atherosclerosis, or endothelial dysfunction, or reducing liver triglyceride content or reducing body weight gain, comprising administering to a subject in need thereof a therapeutically effective amount of the insulin derivative according to claim 15.

18. A method of claim 17, wherein diabetes is Type 1 diabetes or Type 2 diabetes.

* * * * *